(12) United States Patent
Herr et al.

(10) Patent No.: US 11,707,364 B2
(45) Date of Patent: Jul. 25, 2023

(54) PROSTHETIC, ORTHOTIC OR EXOSKELETON DEVICE

(71) Applicant: Otto Bock Healthcare LP, Austin, TX (US)

(72) Inventors: Hugh Miller Herr, Somerville, MA (US); Zhixiu Han, Acton, MA (US); Christopher Eric Barnhart, Carlisle, MA (US); Richard J. Casler, Jr., Lowell, MA (US)

(73) Assignee: Otto Bock Healthcare LP, Austin, TX (US)

( * ) Notice: Subject to any disclaimer, the term of this patent is extended or adjusted under 35 U.S.C. 154(b) by 477 days.

(21) Appl. No.: 16/740,876

(22) Filed: Jan. 13, 2020

(65) Prior Publication Data

US 2020/0146847 A1    May 14, 2020

Related U.S. Application Data

(63) Continuation of application No. 14/407,656, filed as application No. PCT/US2013/045356 on Jun. 12, 2013, now Pat. No. 10,531,965.

(Continued)

(51) Int. Cl.
*A61F 2/60* (2006.01)
*A61F 2/68* (2006.01)
(Continued)

(52) U.S. Cl.
CPC .............. *A61F 2/60* (2013.01); *A61B 5/112* (2013.01); *A61B 5/4851* (2013.01); *A61F 2/68* (2013.01);
(Continued)

(58) Field of Classification Search
CPC ...... A61F 2/60; A61F 2/68; A61F 2/70; A61F 2/64; A61F 2/6607; A61F 2002/5003;
(Continued)

(56) References Cited

U.S. PATENT DOCUMENTS 5,549,700 A * 8/1996 Graham ................ A61F 2/3609
623/22.14
5,611,030 A * 3/1997 Stokes .................. G06T 11/001
345/590

(Continued)

*Primary Examiner* — Jerrah Edwards
*Assistant Examiner* — Melissa A Hoban
(74) *Attorney, Agent, or Firm* — Goodwin Procter LLP

(57) ABSTRACT

A time-dependent decay behavior is incorporated into one or more joint actuator control parameters during operation of a lower-extremity, prosthetic, orthotic or exoskeleton device. These parameters may include joint equilibrium, joint impedance (e.g., stiffness, damping) and/or joint torque components (e.g., gain, exponent). The decay behavior may be exponential, linear, piecewise, or may conform to any other suitable function. Embodiments presented herein are used in a control system that emulates biological muscle-tendon reflex response providing for Reflex Parameter Modulation a natural walking experience. Further, joint impedance may depend on an angular rate of the joint. Such a relationship between angular rate and joint impedance may assist a wearer in carrying out certain activities, such as standing up and ascending a ladder.

30 Claims, 33 Drawing Sheets

Related U.S. Application Data

(60) Provisional application No. 61/679,194, filed on Aug. 3, 2012, provisional application No. 61/662,104, filed on Jun. 20, 2012, provisional application No. 61/658,568, filed on Jun. 12, 2012.

(51) Int. Cl.

| | | |
|---|---|---|
| *A61B 5/11* | (2006.01) | |
| *A61B 5/00* | (2006.01) | |
| *A61F 2/70* | (2006.01) | |
| *A61F 2/64* | (2006.01) | |
| *A61F 2/66* | (2006.01) | |
| *A61F 2/50* | (2006.01) | |
| *A61F 2/76* | (2006.01) | |

(52) U.S. Cl.
CPC ...... *A61F 2/70* (2013.01); *A61F 2/64* (2013.01); *A61F 2/6607* (2013.01); *A61F 2002/5003* (2013.01); *A61F 2002/503* (2013.01); *A61F 2002/5033* (2013.01); *A61F 2002/607* (2013.01); *A61F 2002/701* (2013.01); *A61F 2002/704* (2013.01); *A61F 2002/764* (2013.01); *A61F 2002/765* (2013.01); *A61F 2002/7625* (2013.01); *A61F 2002/7635* (2013.01); *A61F 2002/7645* (2013.01)

(58) Field of Classification Search
CPC ........ A61F 2002/503; A61F 2002/5033; A61F 2002/607; A61F 2002/701; A61F 2002/704; A61F 2002/7625; A61F 2002/7635; A61F 2002/764; A61F 2002/7645; A61F 2002/765; A61F 2002/6827; A61B 5/112; A61B 5/4851
See application file for complete search history.

(56) References Cited

U.S. PATENT DOCUMENTS

| | | | | |
|---|---|---|---|---|
| 5,766,256 A * | 6/1998 | Oudard | ............... | A61F 2/389 623/20.32 |
| 5,809,213 A * | 9/1998 | Bhattacharjya | ...... | H04N 1/6033 358/1.6 |
| 5,916,269 A * | 6/1999 | Serbousek | ............... | A61F 2/34 623/22.24 |
| 5,954,621 A * | 9/1999 | Joutras | ............... | A63B 21/157 482/114 |
| 6,113,642 A * | 9/2000 | Petrofsky | ............... | F16F 9/464 623/24 |
| 6,191,788 B1 * | 2/2001 | Fuller | ............... | G06T 15/10 345/419 |
| 6,549,871 B1 * | 4/2003 | Mir | ............... | B62D 5/046 702/145 |
| 6,558,430 B1 * | 5/2003 | Nakaya | ............... | A61F 2/64 623/44 |
| 7,124,067 B2 * | 10/2006 | Ascenzi | ............... | B33Y 50/00 703/11 |
| 7,396,505 B2 * | 7/2008 | Pope | ............... | B22F 7/062 419/9 |
| 8,350,186 B2 * | 1/2013 | Jones | ............... | B22F 10/20 219/121.66 |
| 8,979,938 B2 * | 3/2015 | Linares | ............... | A61F 2/38 623/22.15 |
| 2002/0052663 A1 * | 5/2002 | Herr | ............... | F16F 9/535 623/24 |
| 2003/0014122 A1 * | 1/2003 | Whiteside | ............... | A61F 2/389 623/20.32 |
| 2003/0114936 A1 * | 6/2003 | Sherwood | ............... | A61F 2/30942 623/23.58 |
| 2004/0049290 A1 * | 3/2004 | Bedard | ............... | A61F 2/644 623/24 |
| 2004/0062786 A1 * | 4/2004 | Ascenzi | ............... | G09B 23/30 424/423 |
| 2005/0112397 A1 * | 5/2005 | Rolfe | ............... | A61F 2/0811 428/593 |
| 2006/0041609 A1 * | 2/2006 | Pellar | ............... | H04N 1/6019 708/290 |
| 2006/0241767 A1 * | 10/2006 | Doty | ............... | A61F 2/4425 623/17.12 |
| 2007/0100450 A1 * | 5/2007 | Hodorek | ............... | A61L 27/52 623/14.12 |
| 2007/0179613 A1 * | 8/2007 | Heinz | ............... | A61F 2/4425 623/17.12 |
| 2008/0046155 A1 * | 2/2008 | Holthaus | ............ | F02D 41/1497 701/51 |
| 2010/0331998 A1 * | 12/2010 | Ringeisen | ............... | A61L 27/50 623/23.61 |
| 2013/0150977 A1 * | 6/2013 | Gabriel | ............... | A61F 2/389 623/20.32 |
| 2013/0261766 A1 * | 10/2013 | Langlois | ............... | A61F 2/70 623/33 |
| 2015/0127118 A1 * | 5/2015 | Herr | ............... | A61F 2/60 623/24 |
| 2015/0238317 A1 * | 8/2015 | Bonutti | ............... | A61F 2/0077 623/17.11 |
| 2016/0074180 A1 * | 3/2016 | Lenzi | ............... | A61F 2/70 623/24 |
| 2017/0061926 A1 * | 3/2017 | Bhattacharjee | .......... | G09G 5/06 |
| 2018/0289493 A1 * | 10/2018 | Mansmann | ......... | A61F 2/30756 |
| 2018/0318106 A1 * | 11/2018 | Ball | ............... | A61B 17/8047 |
| 2019/0053915 A1 * | 2/2019 | Macke | ............... | A61F 2/34 |
| 2020/0179215 A1 * | 6/2020 | Lerner | ............... | A61H 1/0266 |
| 2021/0069409 A1 * | 3/2021 | Castleberry | ....... | A61M 5/14212 |
| 2021/0122040 A1 * | 4/2021 | Lefeber | ............... | A61F 5/0123 |
| 2021/0338440 A1 * | 11/2021 | White | ............... | A61F 2/389 |
| 2021/0353423 A1 * | 11/2021 | Zhang | ............... | A61F 2/30771 |

\* cited by examiner

PROSTHETIC, ORTHOTIC OR EXOSKELETON DEVICE

CROSS REFERENCE TO RELATED APPLICATIONS

This Application is a continuation of U.S. patent application Ser. No. 14/407,656, filed Dec. 12, 20014; which is a 371 application of PCT/US2013/045356, filed Jun. 12, 2013; which claims the benefit of U.S. Provisional Applications 61/662,104 filed Jun. 20, 2012 and 61/658,568 filed Jun. 12, 2012, each of which is incorporated herein by reference

BACKGROUND

1. Field of the Invention

Devices and control systems for biologically-inspired artificial limbs are generally disclosed.

2. Related Art

Existing prosthetic leg devices include a series-elastic actuator which functions as a biologically-inspired muscle-tendon unit to modulate, during a gait cycle, joint impedance, joint equilibrium and torque, in accordance with walking speed and terrain modality (e.g., sloping ground, stairs, etc.). It is desired for prosthetic leg devices to function in a way that matches the human ankle response as captured, in part, by FIG. 1, which illustrates human biomechanical function in a gait cycle, on level-ground. In the schematic of FIG. 1, the gait cycle on level-ground is initiated by a heel-strike event. Other types of gait cycles, such as toe-strike initiated cycles as might occur in steep ramp or stair ascent, are not expressly shown.

Prosthetic leg devices have been designed so as to exhibit response behavior captured by a "dashboard" of biomechanical characteristics, shown in FIG. 2a. These biomechanical characteristics are based on body-mass normalized and walking-speed reference measures from an intact ankle population, including Net Non-Conservative Work, Peak Power, Toe-off Angle and Peak Power Timing. As depicted in FIG. 2a, dashed lines denote +/−sigma error bounds for the normative data, solid lines denote average values for the normative data, and circles represent individual step data wirelessly acquired from an ankle device wearer.

The ankle device depicted in FIG. 2b employs a state machine, implemented in the intrinsic control firmware of the device to modulate the actuator response. The actuator response is programmed to define a joint impedance, joint equilibrium and torque, so as to emulate human function in each gait cycle state. Depending on the phase of gait, the device will enter into an appropriate state. At times, the transition(s) between states for an artificial leg device may be abrupt, or might not accommodate for changes in wearer intent.

SUMMARY

The inventors have recognized and appreciated there to be advantages in employing time-dependent decay behavior in one or more control parameters when the actuator torque of an artificial leg device is modulated during use. While not meant to be limiting, such parameters may include joint equilibrium, joint impedance (e.g., stiffness, damping) and/or joint torque components (e.g,. gain, exponent) of the programmable state (e.g., powered reflex response). The decay behavior may conform to any suitable mathematical relationship, such as an exponential decay, linear drop, quadratic function, piecewise relation, dynamic behavior model that might arise from the output of a linear or non-linear differential equation, or other suitable function. Such behavior, when used in a positive force feedback system, may provide for a smooth experience that emulates biological kinetics (torque, power) and kinematics. For example, this type of control may ease the transition(s) between states of the device (e.g., so that they are generally unnoticeable to the wearer) and may allow for the wearer to alter his/her course during gait in a natural manner.

In an illustrative embodiment, a prosthesis, orthosis or exoskeleton apparatus is provided. The apparatus includes a proximal member; a distal member; a joint connecting the proximal and distal members, the joint adapted to permit flexion and extension between the proximal and distal members; a motorized actuator configured to apply at least one of a joint impedance and a joint torque, the joint impedance including at least one of a stiffness and damping, wherein the stiffness is referenced to a joint equilibrium; a sensor configured to detect at least one of a phase and a change in a phase of joint motion in a repetitive cycle; and a controller configured to modulate at least one of the joint equilibrium, the joint impedance and the joint torque, the modulation employing a decaying time response as a function of at least one of the phase and the detected change in phase of joint motion.

In another illustrative embodiment, a method of controlling a joint impedance and a joint equilibrium of a prosthesis, orthosis or exoskeleton apparatus is provided. The method includes actuating a joint of the apparatus; tracking a current joint position of the apparatus; and controlling a value of the joint equilibrium of the apparatus so as to converge to a value of the current joint position.

In yet another illustrative embodiment, a prosthesis, orthosis or exoskeleton device is provided. The device includes a joint constructed and arranged to permit flexion and extension between a proximal member and a distal member; a motorized actuator configured to apply at least one of a joint impedance and a joint torque, the joint impedance referenced to a joint equilibrium; a sensor configured to detect a characteristic of the device; and a controller configured to modulate at least one of the joint equilibrium, the joint impedance and the joint torque according to the detected characteristic, the modulation exhibiting time-dependent decay behavior.

In a further illustrative embodiment, a prosthesis, orthosis or exoskeleton device is provided. The device includes a joint constructed and arranged to permit flexion and extension between a proximal member and a distal member; a motorized actuator configured to apply at least one of a joint impedance and a joint torque, the joint impedance referenced to a joint equilibrium; a sensor configured to detect an angular rate of at least one of the proximal member, the distal member and a joint connecting the proximal and distal members; and a controller configured to modulate a parameter comprising at least one of the joint equilibrium, the joint impedance and the joint torque according to the detected angular rate to include at least one of a rate dependent stiffness response and a decaying response.

In yet another illustrative embodiment, a prosthesis, orthosis or exoskeleton apparatus is provided. The apparatus includes a proximal member; a distal member; a joint connecting the proximal and distal members, the joint adapted to permit flexion and extension between the proximal and distal members; a motorized actuator configured to apply torque at the joint; a sensor configured to detect at least one of a phase and a change in a phase of joint motion in a repetitive cycle; a battery to store electrical energy and to power the apparatus, a controller configured to short the leads of the motor where the controller recovers electrical energy from the apparatus during at least part of the repetitive cycle.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the present disclosure are described with reference to the following drawings in which numerals reference like elements, and wherein.

DETAILED DESCRIPTION

Figure 1:
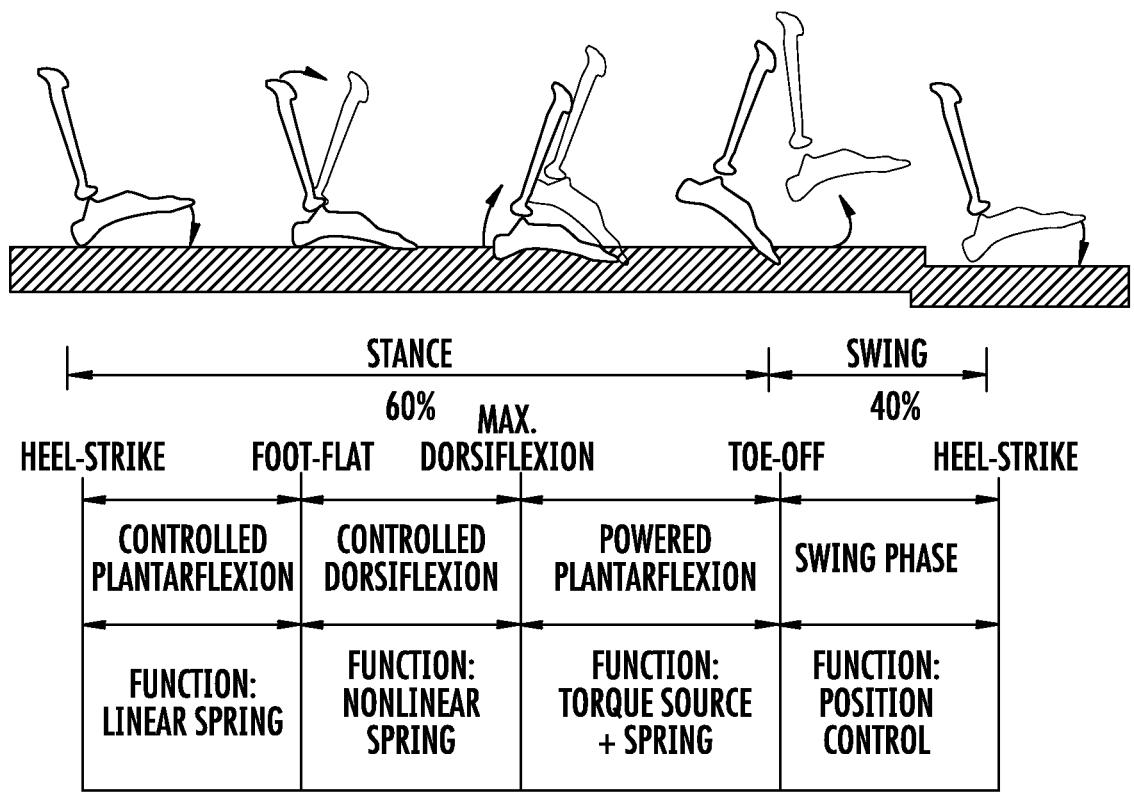
FIG. 1 illustrates a schematic of a human biomechanical gait cycle on level-ground.
Figure 2A:
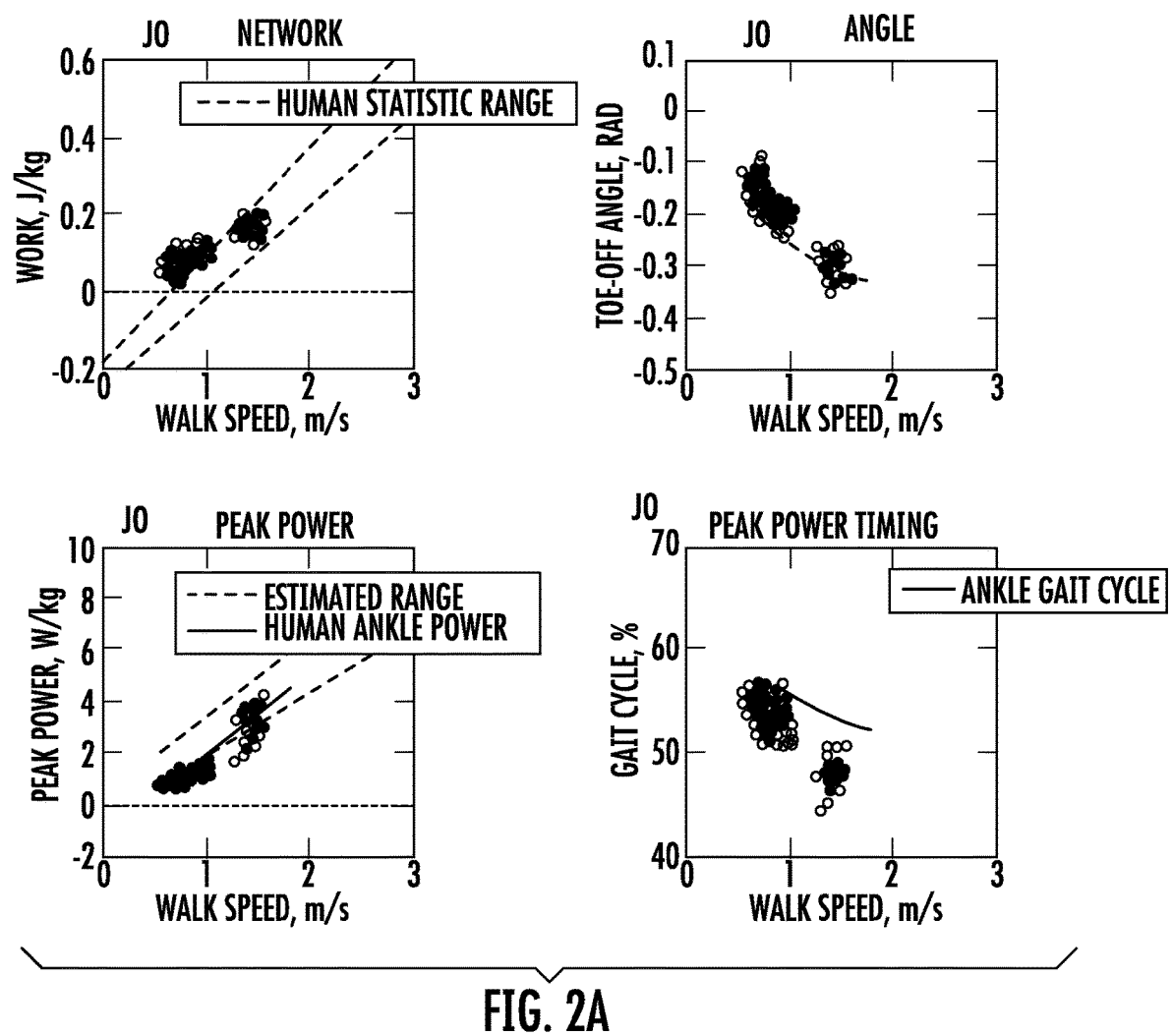
FIG. 2a depicts graphs of walking speed-referenced measures compared to normative measures from an intact ankle population.
Figure 2B:
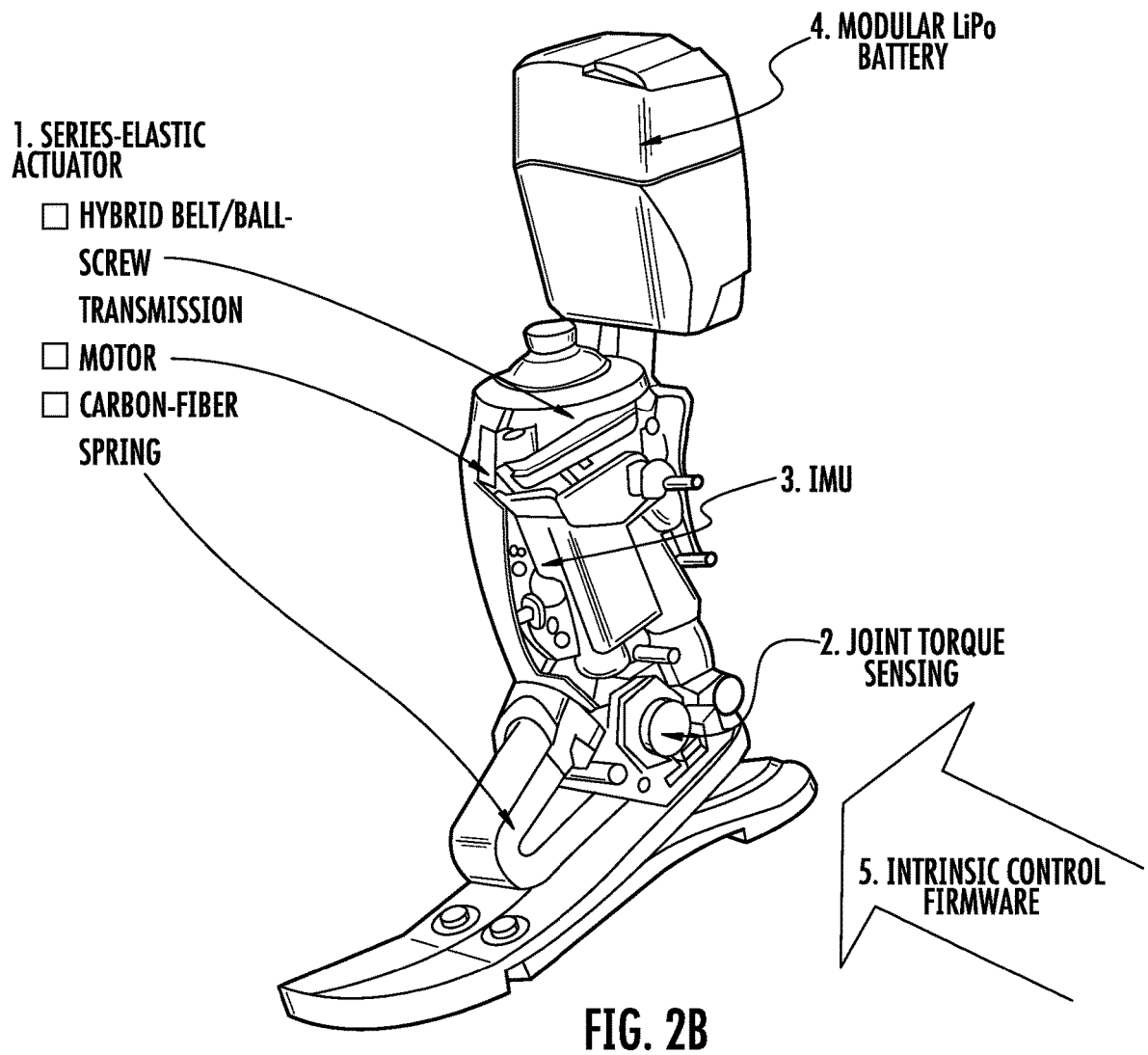
FIG. 2b shows a perspective view of an artificial ankle device.

Various embodiments of the present disclosure relate to a biologically-inspired, sensing and control architecture for bionic leg actuation (e.g., knee joint actuation, ankle joint actuation). As described herein, a bionic device may function to restore or replace anatomical structure(s) and/or exhibit physiological process(es), with one or more electromechanical components. For instance, bionic devices of the present disclosure may emulate stance-phase kinetics (e.g., torque and power) that may occur naturally in intact limbs. Bionic leg joints described herein may employ a series-elastic actuator (SEA) to amplify mechanical power, to enable closed-loop torque control and to enable sensing of actuator torque through a model of the torque-displacement characteristics. In some embodiments, an ankle device may employ a hardstop with known flexion characteristics that limits dorsiflexion travel of the joint. A control system modulates joint impedance (e.g., stiffness, damping), joint equilibrium (e.g., equilibrium location) and joint torque (e.g., motor reflex gain, motor reflex exponent) in accordance with gait cycle state and walking speed, a surrogate for walking speed, or the rate of change of a state variable or sensor in the actuator control system. In some embodiments, the rate of change of the state variable may include an inertial pitch rate (e.g., of a tibial component) and/or an actuator torque rate (e.g., of an ankle or knee joint), shortly after foot strike.

In some embodiments, one or more parameters controlled by the system may exhibit time-dependent behavior. For example, the joint impedance, joint stiffness, joint damping, joint equilibrium, reflex torque gain, reflex torque exponent, or another suitable parameter(s) may employ a time decay (e.g., value of the parameter diminishes over time) during an appropriate phase of gait. Such a decay may exhibit any suitable functional behavior, such as exponential, linear, piecewise, etc. This type of behavior, in some cases, may also provide for a natural experience to the wearer, for example, without producing a feeling of abruptness upon changes in the phase of gait. For instance, a gradual lessening of ankle stiffness upon entry into an Early Stance mode may allow for a wearer to rollover smoothly in a natural manner such that mode changes (i.e., state transitions) of the device are transparent (e.g., almost unnoticeable).

As used herein, a phase of gait may describe a particular state of the device, which may be triggered by a gait event (e.g., heel-strike, toe-off). For example, a phase of gait may refer to: a state transition in a leg prosthesis control system, such as in a joint actuator controller; the inertial state of proximal and distal members of the device; and/or changes in one or more components of the inertial state of the proximal and distal members of the device.

As used herein, a motorized actuator or motorized actuation system may include any suitable motor. For example, motorized actuators may incorporate one or more electric motors, hydraulic motors, pneumatic motors, piezo-actuated motors, shape-memory motors, electro-polymer motors, or any other appropriate motorized device.

As used herein, a characteristic of motion of a device may include one or more of the following: an inertial pose of distal and proximal members of the device; changes in the inertial pose of the distal and proximal members of the device; translational velocity or angular rate of one or more points on the distal and proximal members; kinetics, including force, torque and power, and the derivatives thereof at the joints and at the interface between the device and ground; kinematics, including joint angles, and derivatives thereof; dynamic actuator state(s), including force, torque, displacement in the motor drive and transmission, including the elastic elements embodied within the transmission; and other appropriate characteristics.

While neuroscientists identify increasingly complex neural circuits that control animal and human gait, biomechanists have found that locomotion requires little outside control if principles of legged mechanics are heeded that shape and exploit the dynamics of legged systems. Embodiments according to the present disclosure may include muscle reflex response(s) that encode principles of legged mechanics, and provide a link to the above observations surrounding the behavior of natural limbs. Equipped with reflex control, various embodiments of bionic devices presented herein reproduce human walking dynamics and leg kinetics and kinematics; tolerate ground disturbances; and adapt to slopes without outside parameter intervention(s), such as might otherwise be informed by inertial sensor inputs, neural or cognitive functions. Accordingly, aspects/parameters of the bionic response may be appropriately encoded to adaptively modulate one or more parameters based upon intrinsic kinematic and kinetic measures (e.g., angle and torque including their derivatives) or extrinsic interventions arising from measures of walking speed and terrain (as might be supplied by an inertial measurement unit, for instance), so as to suitably emulate the muscle-tendon reflex. Aspects described herein may employ principles described in the article by Geyer, H. and Herr, H., entitled "A Muscle-Reflex Model that Encodes Principles of Legged Mechanics Produces Human Walking Dynamics and Muscle Activities," submitted to IEEE Transactions on Neural Systems and Rehabilitation Engineering and accepted in 2010, the disclosure of which is hereby incorporated herein by reference in its entirety.

It can be appreciated that embodiments of the present disclosure are not required to incorporate a state machine that transitions from one discrete state to another in a gait cycle. For instance, a mere change in inertial state across a gait cycle (e.g., based on the use of a rate gyroscope to measure a rate of tibial pitch) may be a part of a gait cycle phase.

Systems described herein may be incorporated in devices made by iWalk, Inc., such as in the BiOM$^{T2}$. In some cases, the BiOM$^{T2}$ device employs a series-elastic actuator (SEA) that incorporates a biophysically-based, reflexive control system. This system emulates dominant muscle-tendon behavior, during walking, of the ankle plantar flexors, the Soleus and Gastrocnemius calf muscles, as well as the dominant dorsiflexor, the Tibialis Anterior. The SEA may control ankle joint impedance (e.g., stiffness, damping), virtual spring equilibrium and/or reflexive torque. The SEA system may enable sensing of actuator torque ($\Gamma_{SEA}$) through measurements of series-spring deformation. Additionally, the ankle joint may include a hardstop, which limits the ability for the ankle to move to a position of increased dorsiflexion, after a certain point. In addition to measuring actuator torque, the system may also monitor hardstop torque ($\Gamma_{hs}$) through the measurement of hardstop spring deformation.

A finite state machine may be employed in a State Control Processor to control transitions of the device through different states. The gait cycle states in the State Machine may include early stance, late stance, late stance power, early swing and late swing, which are aligned with the conventional names employed in human biomechanics, namely, controlled plantar flexion, controlled dorsiflexion, powered plantar flexion, early swing and late swing, respectively. The transitions between these walking gait phases may be determined by a system clock (time) and/or the SEA torque ($\Gamma_{SEA}$), hardstop torque ($\Gamma_{hs}$), and their time derivatives.

In some embodiments, the device includes a single finite state machine for walking. As a result, when a single finite state machine is employed, the control system does not revert to a non-walking state machine based on biomechanical change(s) made by the human wearer. Accordingly, the device is less cumbersome than would otherwise be the case if multiple state machines are incorporated.

The system may make some or all motor control actuation decisions based upon kinetic sensory information of the device (e.g., force/torque information), without requiring kinematic sensory information of the device (e.g., positions, velocities, accelerations). For example, the system is not required to employ reflex response parameter interventions as these might be informed by accelerometers or rate gyros or any other sensor for the measurement of overall device positions, velocities or accelerations relative to horizontal or vertical reference planes to adapt to walking speed and terrain modality. As a result, the position of the ankle joint may be controlled based on the interaction forces experienced between the human wearer, the device, and the ground surface. Therefore, contrary to conventional robotic systems, it is not necessary for the device to directly control the position of the ankle joint, whether in stance or swing phases, as systems described herein are controlled based on reflex response(s). Though, it can be appreciated that, in some cases, the system may employ position sensors, accelerometers, rate gyros and/or any other sensor, as suitably desired.

Non-linear, positive force feedback control is applied in powered plantar flexion to emulate human muscle-tendon reflex dynamics. Devices described herein employ positive force feedback with intent to emulate a natural, uncontrolled (e.g., automatic) reflex response. This reflex is implemented by a motor torque control that behaves according to a positive force feedback mathematical relationship involving parameters that include torque gain and torque exponent, each modulated according to the stimulation of certain parameters, for example, the torque rate measured by a series elastic actuator and/or the torque measured at a hardstop.

The system control architecture employs motor and joint angle sensing to compute, via calibrated models, instantaneous SEA and hardstop torque. Instead of using inertial information, the system architecture employs intrinsic measures of torque, torque rate of change and time duration within a gait cycle state to inform transitions in the State Machine that directs the response modulation in a Motor Processor and, in some embodiments, may rely exclusively on torque and time within a state to inform the transitions. That is, measurements of inertial information, such as position, velocity and acceleration are not used to inform parameter interventions that modulate the actuator response. Rather, force measurements, such as force and torque measured over time, may be used as input to direct the response modulation of the joint actuator.

The device may exhibit reflexive behavior, without any system memory. That is, the system may monitor device torque(s) and reflexively respond to such torque(s) with little delay between sensing and actuation. As a result, the monitoring of torque throughout or during a portion of a gait cycle may be the basis for modulation of control actions during a current gait cycle, without any consequence to control actions that affect a subsequent gait cycle.

In some embodiments, the control system does not require detection of particular gait patterns or events, and in response, the control system is not required to modulate either the control algorithm, or its system parameters. The control algorithm and its parameters are not necessarily adjusted in any manner in response to a user transitioning from a walk to a run, nor while ambulating from a level-ground surface to an incline, nor from level-ground to steps, nor while moving to standing, nor from a standing position to a sitting position, nor from a standing position to a leaning position, nor from a sitting position to a lying down position, nor while putting on pants. That is, despite the type of action the wearer may currently be performing, the control system may function according to a single state machine control, without regard to the type of user action currently performed.

The control system may be configured to detect a foot strike with the ground surface based on torque/force information. Independently of how the device has struck the ground, whether it is a heel strike, a toe strike, or a foot-flat strike, the system may run the same algorithm with the same control parameters.

Further, walking speed may be estimated from a known linearly correlated relationship with normalized, peak derivative of SEA torque in late stance. That is, torque rate may be used as an estimate (or surrogate) of a current walking speed so as to inform the reflex parameter modulation. In particular, the gain and exponent parameters of a reflex relationship may be modulated based on a rate of change of a parameter (e.g., pitch rate, torque rate). For example, a rate-based blending (interpolation) of the parameters may be employed.

In addition, to achieve a smooth and natural response, in some embodiments, the stiffness and/or damping of the joint in Early Stance may be designed to decay exponentially, for example, smoothly reducing stiffness/damping so as to increase joint compliance. Such exponential decay behavior, for impedance, may be particularly beneficial for a wearer of an artificial leg device when walking slowly on uneven terrain or descending down a steep slope, allowing for seamless, hi-fidelity device control.

In some embodiments, artificial leg devices are constructed according to a biologically-inspired approach where an IMU is not required for their use. A number of design principles are considered in constructing the artificial leg device.

For example, the time duration in a state, torque and torque derivative (torque rate) may guide the device in transitioning from one state to another, as well as to modulate the reflex parameters, which may or may not correlate with a current walking speed. In some cases, a single measured parameter may be sufficient as a signal for transitioning the device between states and/or estimate walking speed. As discussed, time duration within a state, SEA torque ($\Gamma_{SEA}$) and hardstop torque ($\Gamma_{hs}$)—and the time derivatives of these may be used as parameters that the system uses to inform state transitions and, in some cases, may be used independently and/or exclusively from other parameters. Peak SEA torque rate as sampled during late stance may be employed in the adjustment of the late stance power reflex, which may occur independently of an estimation (or correlation) of walking speed. As such, it may be a useful observation, yet not necessary for embodiments of the present disclosure, that the above-mentioned rate(s) may correlate with walking speed, for a broad range of wearers. As such, it is not necessary in the preferred embodiment to explicitly estimate the walking speed and to use that estimate to inform the reflex response modulation. So, the intrinsic inertial, kinematic or kinetic may be used directly to inform that modulation.

As muscle-tendon units of an intact limb do not employ inertial sensing to modulate their response, such intrinsic measures may enable the device to behave and respond as a more natural muscle-tendon unit. Instead, in an intact ankle, muscle and tendon stretch (torque) and their various rates of change are key inputs to the spinal reflex arc connecting the tendon and the muscle. As a result, transitions are more natural and consistent even when the wearer walks softly or runs and jumps in place.

Further, the system may employ a uniformly-applied stiffness/impedance that decays smoothly after foot strike. When the impedance after foot strike is set to decay, "impedance switching" between states, and the abrupt nature that often accompanies such a switch, may be eliminated. Early Stance impedance—generally defined by stiffness ($k_{es}$) and damping ($b_{es}$)—may be used by all states, except, in some cases, it might not be used during late stance power and early swing. Impedance may be set in late-swing to a programmable (tuned) value. In some embodiments, $k_{es}$ decays exponentially to a programmable value, $k_{es_\infty}$, which is typically a small fraction of the initial value, $k_{es_0}$.

Exponential decay of impedance, or one or more other appropriate parameters, may begin at entry into Early Stance. In some cases, the time constant for decay may be set so that the stiffness is substantially maintained (e.g., does not drop quickly) during controlled plantar flexion (CP) (e.g., a time duration between 0.05-0.2 seconds), such as when walking at a brisk walking speed. When walking more slowly, e.g., down a steep hill, the stiffness may be set to drop smoothly, or more quickly, so as to enable the foot to find an equilibrium state at foot-flat with a diminished spring restoring torque—thereby reducing socket stress. The exponential decay behavior (e.g., for joint impedance, joint equilibrium, torque, or others) may continue for a portion of or for the entire gait cycle. For instance, in some cases, exponential decay may continue until it is reset at entry into Early Stance. Such transitions may occur without the wearer even noticing the occurrence of a state transition—thereby eliminating confusion and irritation.

A single walking state machine may deliver a biomimetic response either while walking or not walking, without need for a secondary non-walking state machine. Instead of discretely switching between a non-walking state machine and a walking state machine, state machines of the present disclosure may use the Early Stance state to uniformly deliver a biomimetic response without having to reconfigure the joint impedance and/or joint equilibrium when in a non-walking state. To accomplish this, the walking state machine may cause transition(s) to Early Stance if the time duration within any of the other walking machine states exceeds a programmable limit for that state, typically about two seconds. The stiffness, $k_{es}$, may continue to decay to deliver a smoothly varying impedance that, in the limit, devolves to a substantially lightly damped response that responds naturally for non-directed activities that do not involve locomotion. As discussed above, for some embodiments, only torque and torque derivatives are used to inform the logic transition between states, for example, from early stance to late stance and late stance power where locomotion may then be initiated.

In some embodiments, spring impedance (e.g., stiffness, damping) may be dependent on angular rate in, for example, an ankle or a knee. For instance, an artificial joint device may employ a bionic control system that modulates the impedance of the joint so as to assist the wearer during stair ascent, steep ramp ascent or during the transition from sitting to standing. In some cases, when flexed past a certain threshold angle, the spring stiffness of the joint may be rate dependent, applying positive feedback in response to increases in the joint angular rate or the absolute value of joint angular rate. As an example, the spring stiffness of an artificial knee joint may be modulated such that when a wearer is standing up and the angular rate is increased, the joint becomes stiffer so as to provide increased support during the standing motion. Such support is effective to assist the wearer in standing up.

The present disclosure relates to U.S. Pat. No. 8,075,633 entitled "Active Ankle Foot Orthosis"; U.S. patent application Ser. No. 13/349,216, entitled "Controlling Powered Human Augmentation Devices"; U.S. patent applications entitled "Hybrid Terrain Adaptive Lower-Extremity Systems" corresponding to Ser. Nos. 61/231,754; 12/552,013; 12/552,021; 12/552,028; 12/552,036; and 12/551,845; U.S. patent application entitled "Biomimetic Transfemoral Prosthesis" corresponding to Ser. No. 61/554,921; U.S. patent application entitled "Powered Ankle Device" corresponding to Ser. No. 61/595,453; U.S. patent application entitled "Under-Actuated Exoskeleton" corresponding to Ser. No. 61/659,723; U.S. patent application entitled "Walking State Machine for Control of a Bionic Ankle Joint" corresponding to Ser. No. 61/658,568; U.S. patent application entitled "Bionic Control System for an Artificial Ankle Joint" corresponding to Ser. No. 61/662,104; U.S. patent application entitled "Biomimetic Ankle and Knee Actuator Designs" corresponding to Ser. No. 61/451,887; U.S. patent application entitled "Terrain Adaptive Powered Joint Orthosis" corresponding to Ser. No. 13/417,949; U.S. patent application entitled "Powered Joint Orthosis" corresponding to Ser. No. 13/347,443; U.S. patent application entitled "Using Knee Trajectory as a Discriminator in a Prosthesis or Orthosis" corresponding to Ser. No. 61/435,045; U.S. patent application entitled "Terrain Adaptive Powered Joint Orthosis" corresponding to Ser. No. 13/356,230; U.S. patent applications entitled "Controlling Power in a Prosthesis or Orthosis Based on Predicted Walking Speed or Surrogate for Same" corresponding to Ser. Nos. 61/432,083; 13/079,564; 13/079,571; U.S. patent application entitled "Estimated Hardstop Ankle Torque Contribution Using Measurements of Bumper/Ankle Shell Deflection" corresponding to Ser. No. 61/422,873; U.S. patent application entitled "Implementing a Stand-up Sequence Using a Lower Extremity Prosthesis or Orthosis" corresponding to Ser. No. 12/872,425, International Patent Application Nos. PCT/US2011/031105; PCT/US2012/020775; PCT/US2012/021084; and U.S. Provisional Patent Application No. 61/649,640, the disclosures of each of which are hereby incorporated herein by reference in their entirety.

In particular, concepts described herein may be guided by design principles that motivate use of positive force feedback, use of intrinsic, motor damping behavior to implement dynamic clutches, and catapult behaviors, such as those described in U.S. patent applications entitled "Variable-Mechanical-Impedance Artificial Legs" corresponding to Ser. Nos. 60/395,938; 10/613,499; 13/363,820, the disclosures of each of which are also hereby incorporated herein by reference in their entirety.

It should be understood that for those skilled in the art, the control architecture described herein may be extended to bionic ankles that employ physical and/or SEA-applied virtual, unidirectional and bi-directional parallel elastic elements where torque-displacement characteristics of these systems may be calibrated before use. Further, while such control architecture(s) may be applied to a bionic ankle prosthesis, these principles may be readily extended to orthotic, exoskeletal or humanoid applications in lower-extremity augmentation of ankle, knee and hip.

Figure 3:
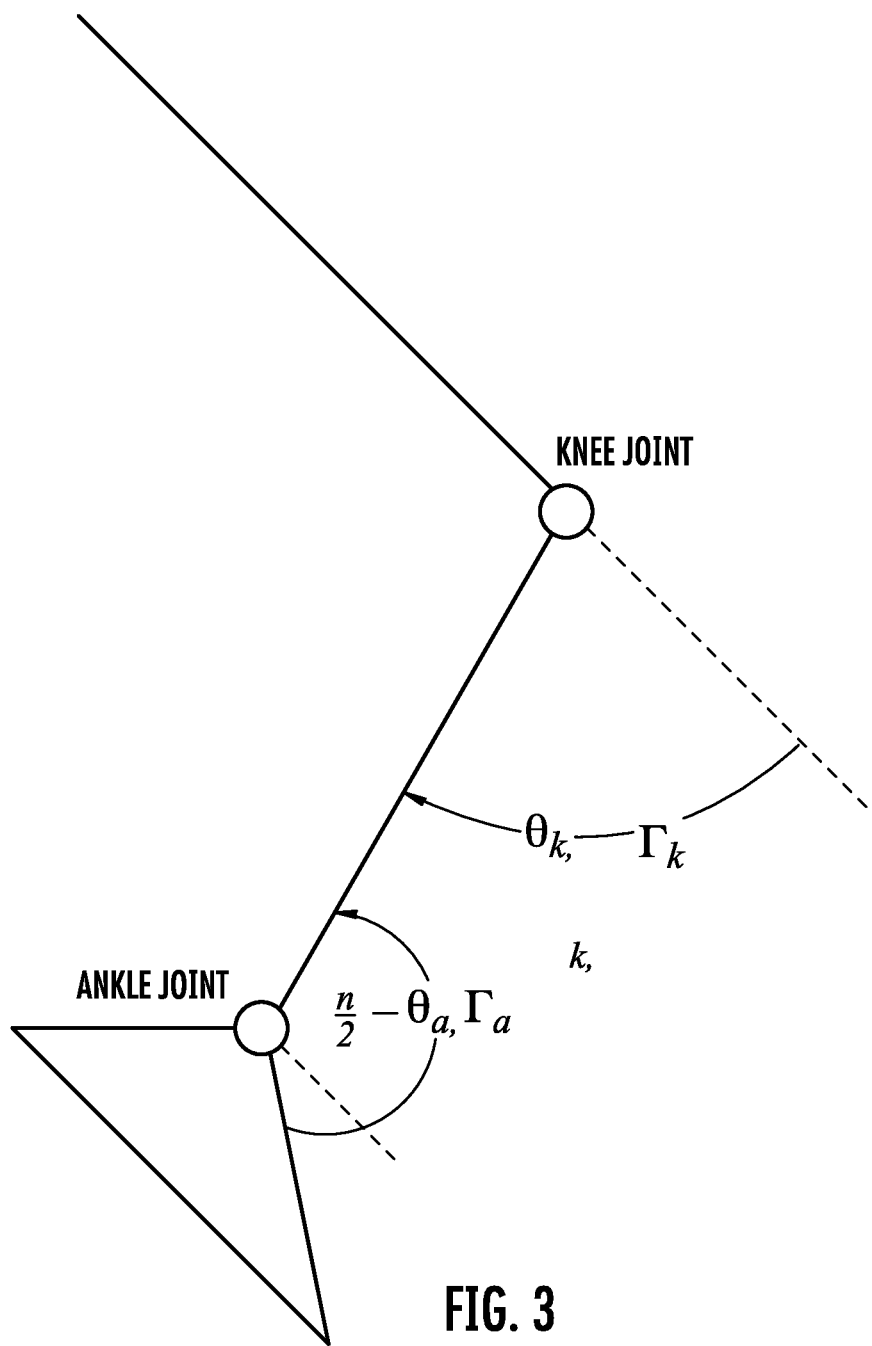
FIG. 3 illustrates a schematic of an artificial ankle device.

While systems in accordance with the present disclosure do not require inertial measurements as input for actuator modulation, it can be appreciated that systems described herein may be used in place of or in combination with inertial measurement systems. For instance, an actuator response may be accomplished by controlling motor torque, $\tau_m$, in a closed-loop or open-loop manner, to match a desired response. In such an architecture, joint angle, motor angle and 6-DOF inertial state (orthogonally-opposed measures of local angular rate and acceleration as sampled by an Inertial Measurement Unit (IMU)) may be used to compute SEA and hardstop torque via calibrated models, to inform state machine transitions, to estimate walking speed and/or to adapt to changes in walking speed or terrain modality. As discussed above, SEA torque and hardstop torque may be used as input to modulate reflex parameters employed in powered plantar flexion. Table 1 provides a summarized mapping of the intrinsic firmware states to the level-ground, gait cycle states as implemented in an artificial ankle device. FIG. 3 shows a schematic of an artificial ankle device that illustrates various parameters that may be referenced in the present disclosure.

TABLE 1

Alignment of level-ground gait cycle states with intrinsic firmware states for an embodiment.

| Level-Ground Gait Cycle State | Intrinsic Firmware State | Actuator Response[1] |
|---|---|---|
| Controlled Plantar Flexion (CP) | State 4: Early Stance (ES) | $\tau_m = -k_{es}(\theta - \theta_{es}) - b_{es}\dot{\beta}$ |
| Controlled Dorsiflexion (CD) | State 5: Late Stance (LS) | $\tau_m = -k_{ls}(\theta - \theta_{es}) - b_{ls}\dot{\beta}$ |
| Powered Plantar Flexion (PP) | State 6: Late Stance Power (LSP) | $\tau_m = -k_{lsp}(\theta - \theta_{pp}) - b_{lsp}\dot{\beta} + p_{ff}(\hat{s})\tilde{\Gamma}_{ankle}^{N(\hat{s})}$ Where $\tilde{\Gamma}_{ankle} = \dfrac{\Gamma_{SRA} + \Gamma_{hs}}{\Gamma_0}$, and $\Gamma_{SEA}$ = Ankle torque supplied by the SEA, $\Gamma_{hs}$ = Ankle torque supplied by the flexion of the hardstop, $\Gamma_0$ = A normative peak dorsiflexion torque approximated by 1.7 Nm per kg of wearer body mass established by an intact ankle population, $\hat{s}$ is the estimated instantaneous walking speed, $p_{ff}(\hat{s})$ is the positive force feedback reflex gain, $N(\hat{s})$ is the reflex exponent, $\hat{s} = \hat{s}(\Psi_{ls})$ where $\Psi_{ls}$ is the tibia pitch rate in late stance and $\theta_{pp}$ is the tail-spring equilibrium |
| Swing (SW) | State 2: Early Swing (ESW) | A biologically-derived second-order response that returns the ankle joint angle, $\theta(t)$, to a position, $\theta_{es}$, where $\tau_m = -k_{esw}(\theta(t) - \theta_0(t)) - b_{esw}(\dot{\beta} - \dot{\theta}_0)$ and $\tau_{esw}^2 \ddot{\theta}_0 + 2\tau_{esw}\dot{\theta}_0 + \theta_0 = \theta_{esw}$ where $\tau_{esw}$ is the time constant of the second-order response. |
| | State 3: Late Swing (LSW) | $\tau_m = -k_{es}(\theta - \theta_{es}) - b_{es}\dot{\beta}$ |
| Not Walking | Non-walking State Machine | $\tau_m = -b_{nw_1}\dot{\beta}$ (shorted leads damping for two seconds) $\tau_m = -b_{nw_2}\dot{\beta}$, programmable light damping |

In systems that operate under the firmware states summarized by Table 1, the State Machine employs state transitions that are informed by time duration within the state, actuator torque, hardstop torque, and inputs from the Inertial Measurement Unit (IMU). Complex measures of "jerk" and vibration applied to the z-component of the local or world-referenced acceleration are employed to detect heel or toe strike transition from late swing (LSW) to early stance (ES). Logic employing pitch velocity (tibia rotation in the sagittal plane) is used as a "guard" (qualifying) condition prior to applying the accelerometer-based foot strike logic. Pitch velocity, as measured at or near the entry into late stance (LS) may be used (as a surrogate) to estimate walking speed and as input for determining resulting reflex response parameters ($p_{ff}(\hat{s})$ and $N(\hat{s})$) in late stance power (LSP).

Further, pitch rate or velocity may be used to inform state transitions from a non-walking state machine into a walking state machine. While such an IMU-based approach may work well for normal gait cycles involving locomotion (e.g., walking), such an approach might not be optimized for non-walking type sequences, for example, those that may occur when the wearer is moving slowly in a confined space, moving between standing and sitting positions, or ascending/descending a ladder. In a small percentage of such cases, a completely IMU-based actuator may have a tendency to respond more vigorously than desired. Conversely, in situations where the wearer is running or jumping in place, the state machine might miss an occasional transition, thereby causing the actuator response to be, in some cases, inconsistent.

The impedance response when the system is set to a non-walking state may, at times, be constrained to be a viscous damper (e.g., have a high damping coefficient resulting from shorting of the motor leads) for a discrete period of time (e.g., approximately two seconds) followed by a more lightly-damped response, which is a less than natural response for the wearer. In cases where transitions between non-walking and walking occur over short time intervals, the step response in viscosity may become less than desirable.

Figure 4:
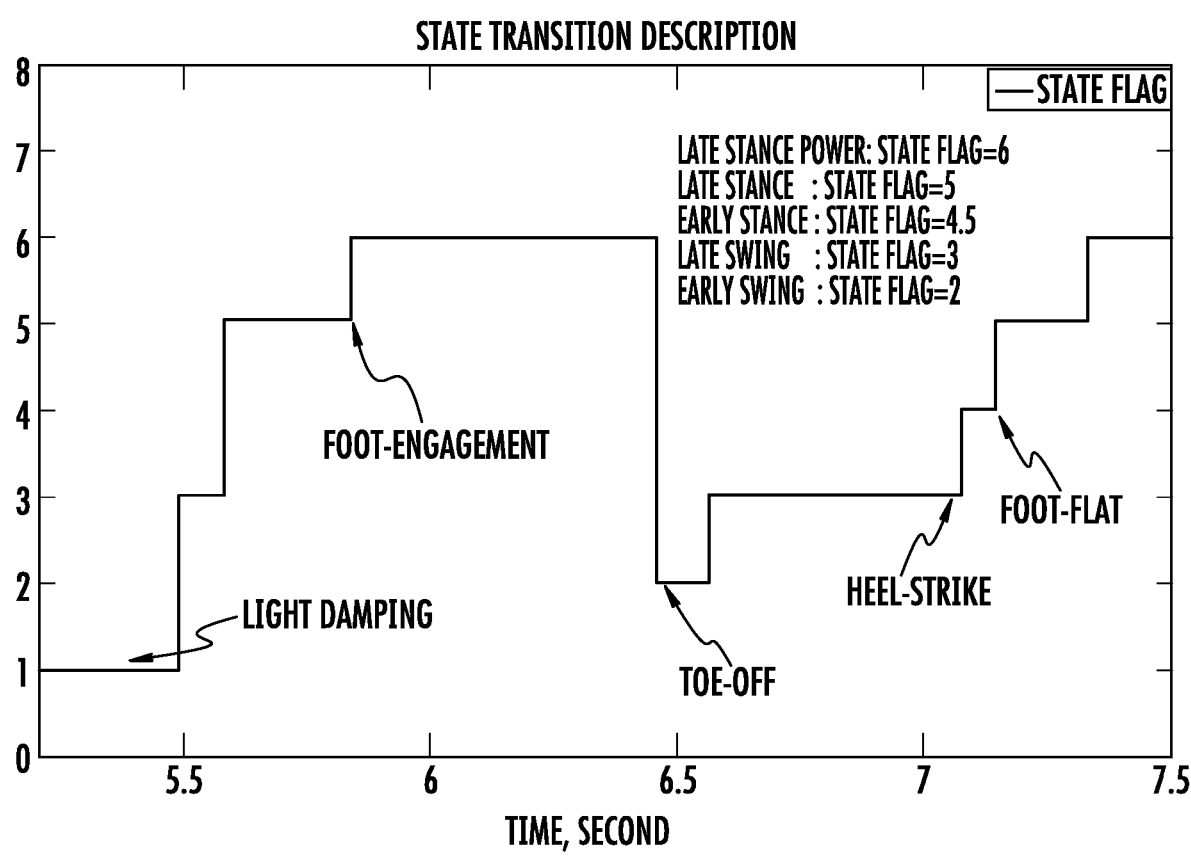
FIG. 4 shows a state transition graph of two gait cycles of an artificial leg device in accordance with some embodiments.

Considering again artificial leg devices that are programmed in a biologically-inspired manner where an IMU is not required, Table 2 provides a summary for such a device. Such devices may be constructed and programmed to capture the reliance on torque-time and the use of an exponential decay so as to eliminate or reduce the abruptness that may result due to transition from one state to another.

be computed as a function directly of the SEA torque rate without loss of generality in another preferred embodiment. FIG. 4 illustrates various state transitions that may occur throughout two typical gait cycles—first exiting from Early Stance into two successive heel-strike first gait cycles. Note that for convenience, virtual state 1 is used as a representation of Early Stance at $t=\infty$. As described earlier, the early stance stiffness, $k_{es}$, decays exponentially leaving the damping, $b_{es}$, as the dominant impedance component.

Early Swing (ESW) to Late Swing (LSW) Transition

As shown in FIG. 4, the ESW-LSW (2-3) transition may occur at a fixed time (e.g., approximately 100 msec, between about 10 msec and about 200 msec) after entry into ESW.

TABLE 2

Alignment of level-ground gait cycle states with intrinsic firmware states for an embodiment.

| Level-Ground State | Intrinsic Firmware State | Actuator Response[2] |
|---|---|---|
| Controlled Plantar Flexion (CP) Controlled Dorsiflexion (CD) | State 4: Early Stance (ES) State 5: Late Stance (LS) | $\tau_m = -k_{es}(t)(\theta - \theta_{es})(1 - u_1(\theta - \theta_{es})) - b_{es}\dot{\beta}^3$ Where $\tau_{es}\dot{k}_{es}(t) + k_{es} = k_{es\infty}$; $\theta_{es} - \theta(t-0)$; $k_{es}(0) = k_{es_0}$; $b_{es} = b_{es_0}$ for $\theta \le \theta_{es}$ and $b_{es} = b_{es_{large}}$ for $\theta > \theta_{es}$ and $u_1(x)$ is a unit step function of $x$[4] |
| Powered Plantar Flexion (PP) | State 6: Late Stance Power (LSP) | $\tau_m = -k_{lsp}(t)(\theta - \theta_{pp})(1 - u_1(\theta)) - b_{lsp}\dot{\beta} + p_{ff}(\hat{s})\tilde{\Gamma}_{ankle}^{N(\hat{s})}$ Where $$\tilde{\Gamma}_{ankle} = \frac{\Gamma_{SEA} + \Gamma_{hs}}{\Gamma_0}, \text{ and}$$ $\Gamma_{SEA}$ = Ankle torque supplied by the SEA, $\Gamma_{hs}$ = Ankle torque supplied by the flexion of the hardstop, $\Gamma_0$ = A normative peak dorsiflexion torque approximated by 1.7 Nm per kg of wearer body mass established by an intact ankle population, $\hat{s}$ is the estimated instantaneous walking speed, $p_{ff}(\hat{s})$ is the positive force feedback reflex gain, $N(\hat{s})$ is the reflex exponent, $\hat{s} = \hat{s}(\Gamma_{SEA_{ls}})$, where $\Gamma_{SEA_{ls}}$ is the peak time-derivative of the SEA torque, $\Gamma_{SEA}$, in late stance and $\theta_{pp}$ is the tail-spring equilibrium, $k_{lsp}(t)$ is defined as $\max\left(\frac{\Gamma_{SEA}}{\theta(t) - \theta_{pp}}\right)$ |
| Swing (SW) | State 2: Early Swing (ESW) | A biologically-derived second-order response that returns the ankle joint angle, $\theta(t)$, to a poisition, $\theta_{esw}$, where $\tau_m = -k_{esw}(\theta(t) - \theta_0(t)) - b_{esw}(\dot{\beta} - \dot{\theta}_0(t))$ and $\tau_{esw}^2\ddot{\theta}_0 + 2\tau_{esw}\dot{\theta}_0 + \theta_0 = \theta_{esw}$ Where $\tau_{esw}$ is the time constant of the second-order response. |
| | State 3: Late Swing (LSW) | $\tau_m = -k_{es_0}(\theta - \theta_{es_0}) - b_{es_0}\dot{\beta}$ Where $\theta_{es_0} = \theta(t)$ on every time step to track the instantaneous joint angle. |

To those skilled in the art it should be readily apparent that the computation and prediction of walking speed is not necessary. In some embodiments, the reflex parameters can During ESW, an overdamped, second-order, joint equilibrium trajectory is launched, that returns the ankle angle, $\theta$, back to $\theta_{es}$—a position at or near the neutral position so as to avoid a tripping hazard. In some embodiments, the time constant, $\tau_{esw}$ applied in this trajectory is between about 10 msec and about 150 msec (e.g., approximately 50 msec), so as to correspond with that of an intact human ankle.

Late Swing (LSW) to Early Stance (ES) Transition

Figure 5:
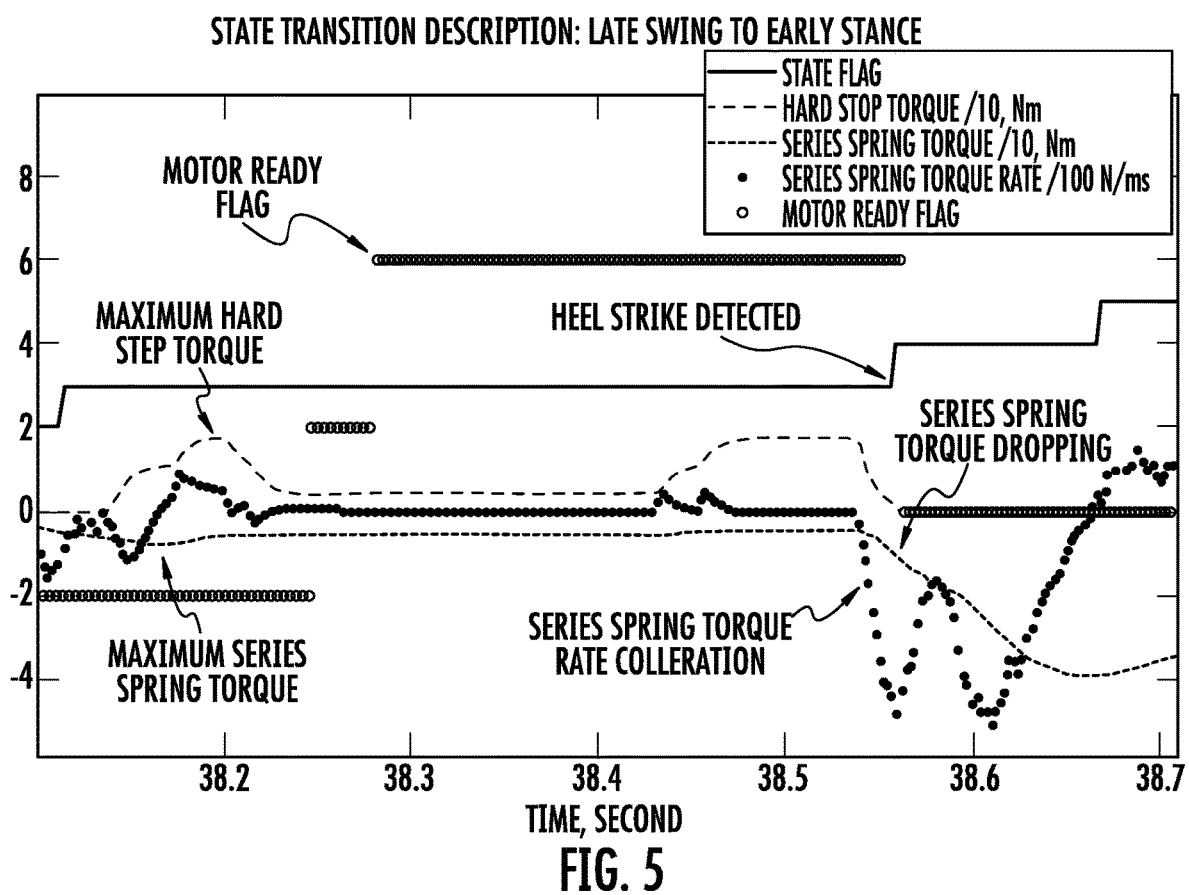
FIG. 5 depicts a state transition graph of a heel-strike-first late swing to an early stance transition in accordance with some embodiments.

FIG. 5 illustrates an embodiment of a state transition from Late Swing to Early Stance (3-4). The embodiment shows the hardstop ($\Gamma_{hs}$) and SEA (torque $\Gamma_{SEA}$, torque rate $\dot{\Gamma}_{SEA}$) torque component response for a heel-strike, first transition. The state and motor ready flags are also shown. In this example, the motor ready flag denotes the motor controller state. As shown in this figure, a value of −2 denotes that an ankle trajectory is running and has not yet finished. A value of +2 denotes that the ankle trajectory has completed and that a motor coil resistance measurement is being acquired. A value of 6 denotes that the motor controller is ready to apply animpedance or respond to a new trajectory or function command.

Figure 6:
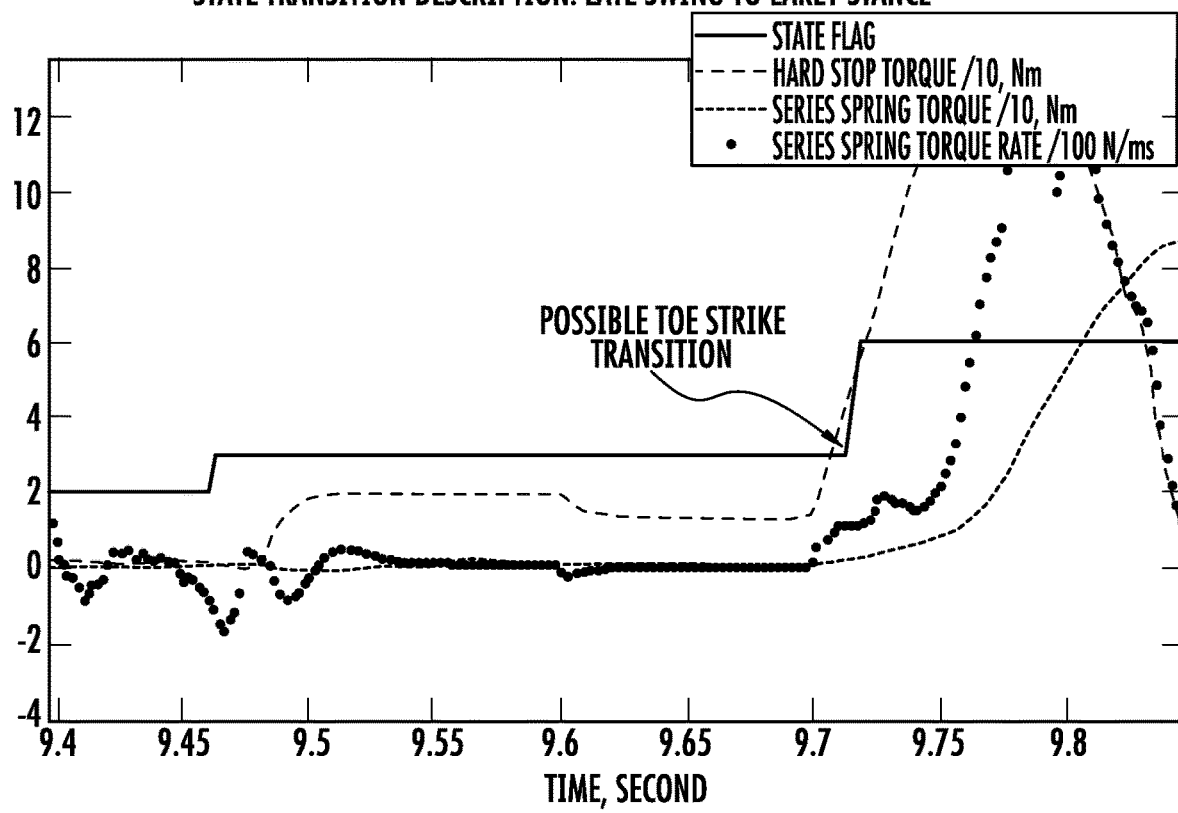
FIG. 6 illustrates a state transition graph of a toe-strike-first late swing to an early stance transition in accordance with some embodiments.
Figure 7:
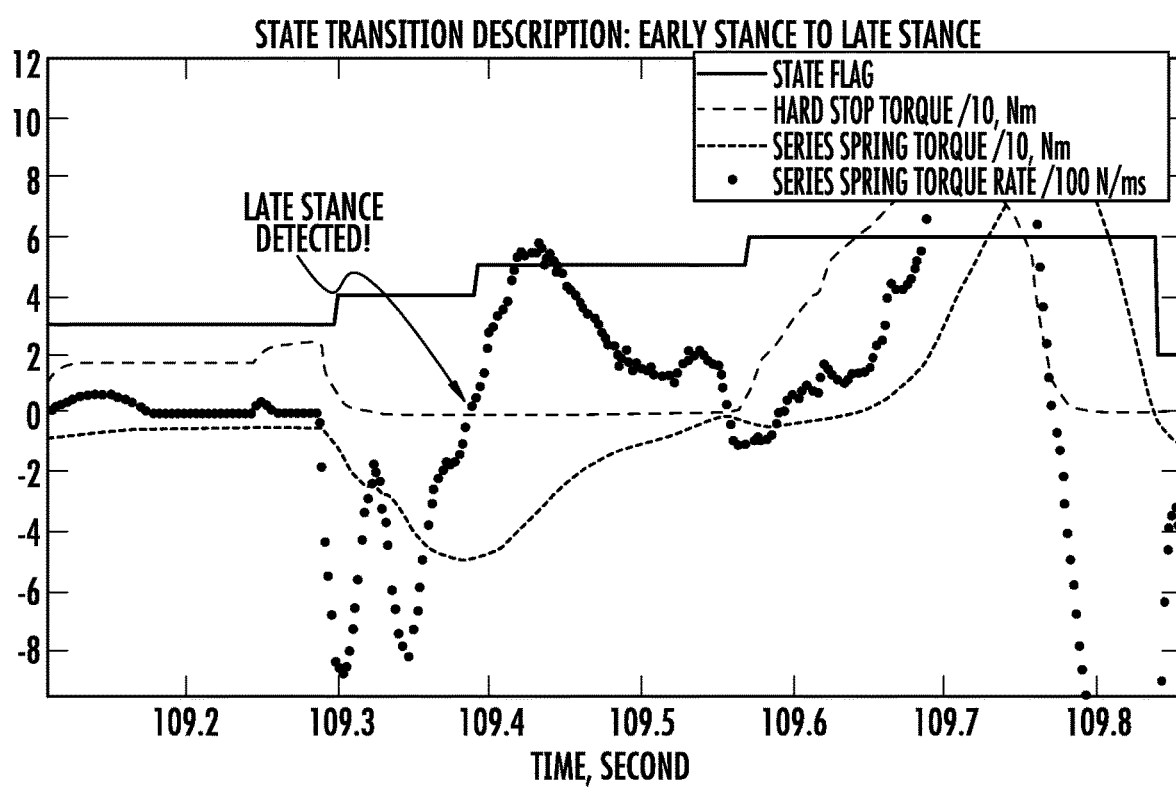
FIG. 7 shows a state transition graph of a heel-strike initiated early stance to a late stance transition in accordance with some embodiments.
Figure 8:
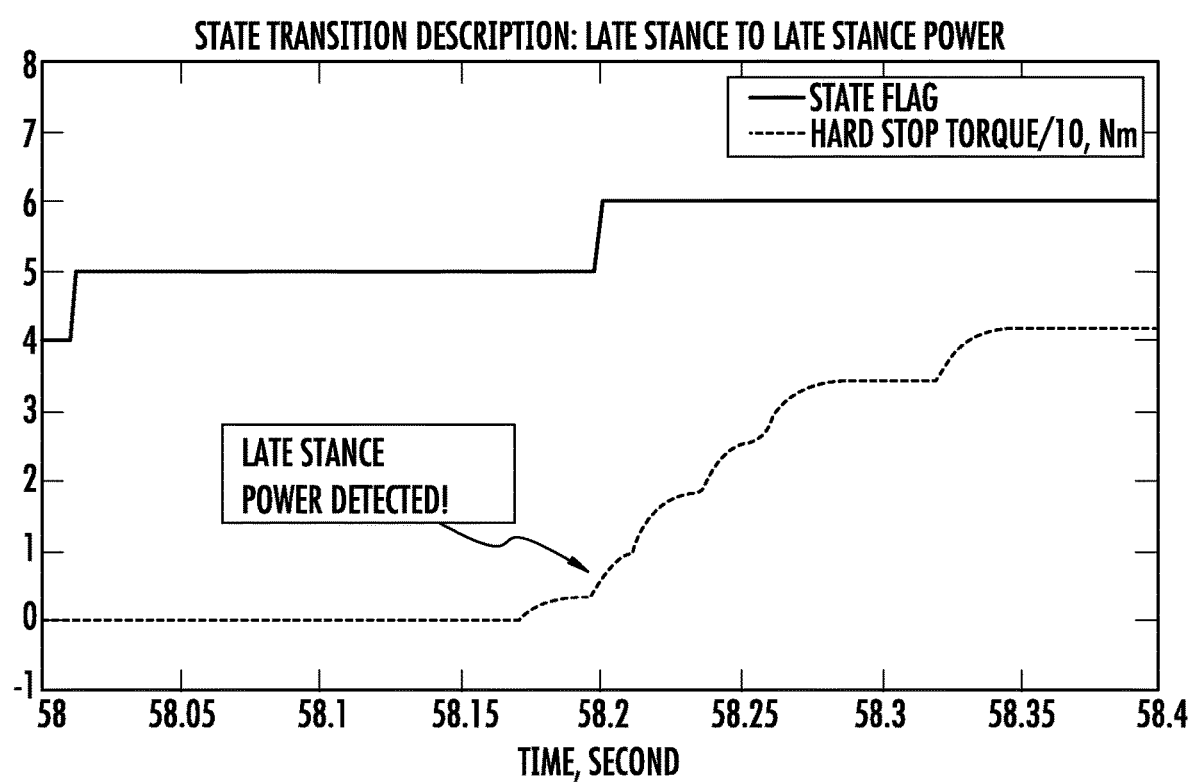
FIG. 8 depicts a state transition graph of a late stance to a late stance power transition in accordance with some embodiments.
Figure 9:
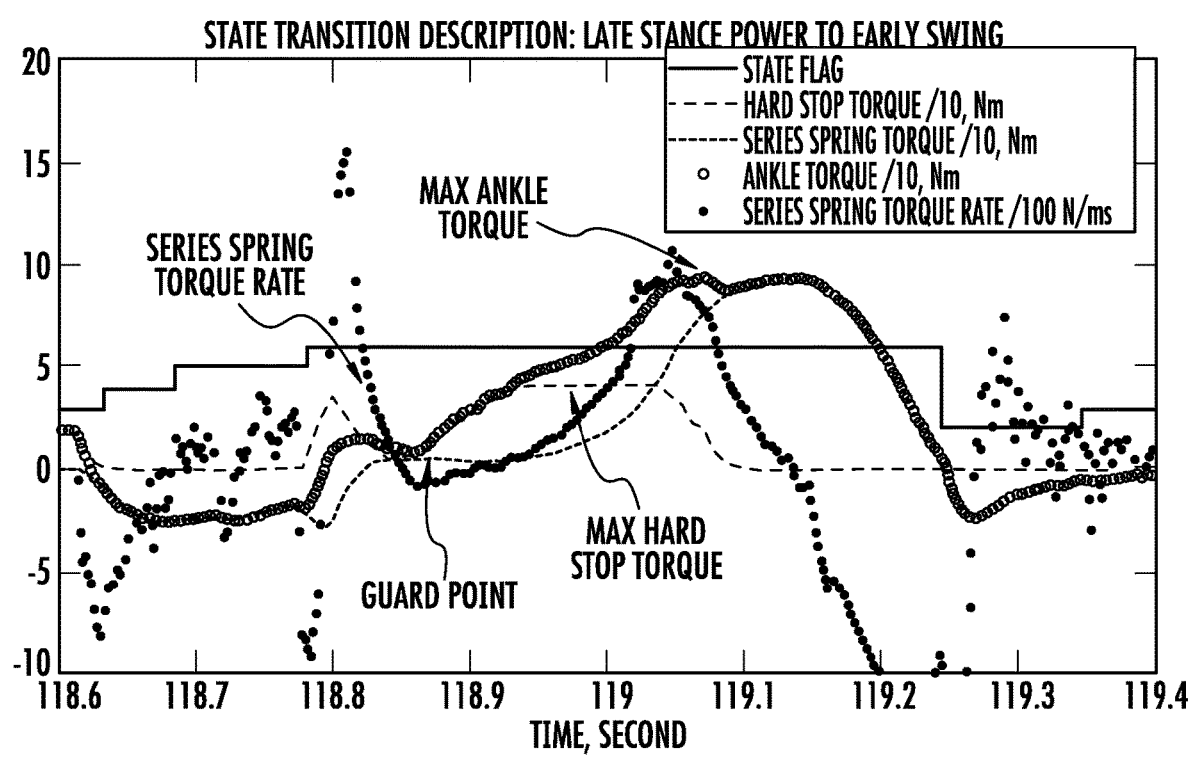
FIG. 9 shows a state transition graph of a late stance power to an early swing toe-off detection in accordance with some embodiments.

FIG. 6 depicts another embodiment of a state transition from Late Swing to Early Stance (3-4). Instead of a heel-strike transition, this embodiment shows a toe-strike transition. As can be seen, a substantial difference between the two different ground impact conditions is that in the situation where heel-strike occurs first, the ground impact imparts a large negative torque, $\Gamma_{SEA}$, and a large negative torque rate $\dot{\Gamma}_{SEA}$, on the SEA. Whereas in the case where toe-strike occurs first, the ground impact imparts a large positive torque, $\Gamma_{hs}$, against the hardstop. As such, to detect these conditions reliably, a "guard condition" may first be applied to the state transition logic so as to reject the "noise" in $\Gamma_{SEA}$ and $\Gamma_{hs}$, during the swing phase—this is a result of the SEA torque applied to achieve the ankle trajectory and a possible collision with the hardstop during the time interval.

Figure 10A:
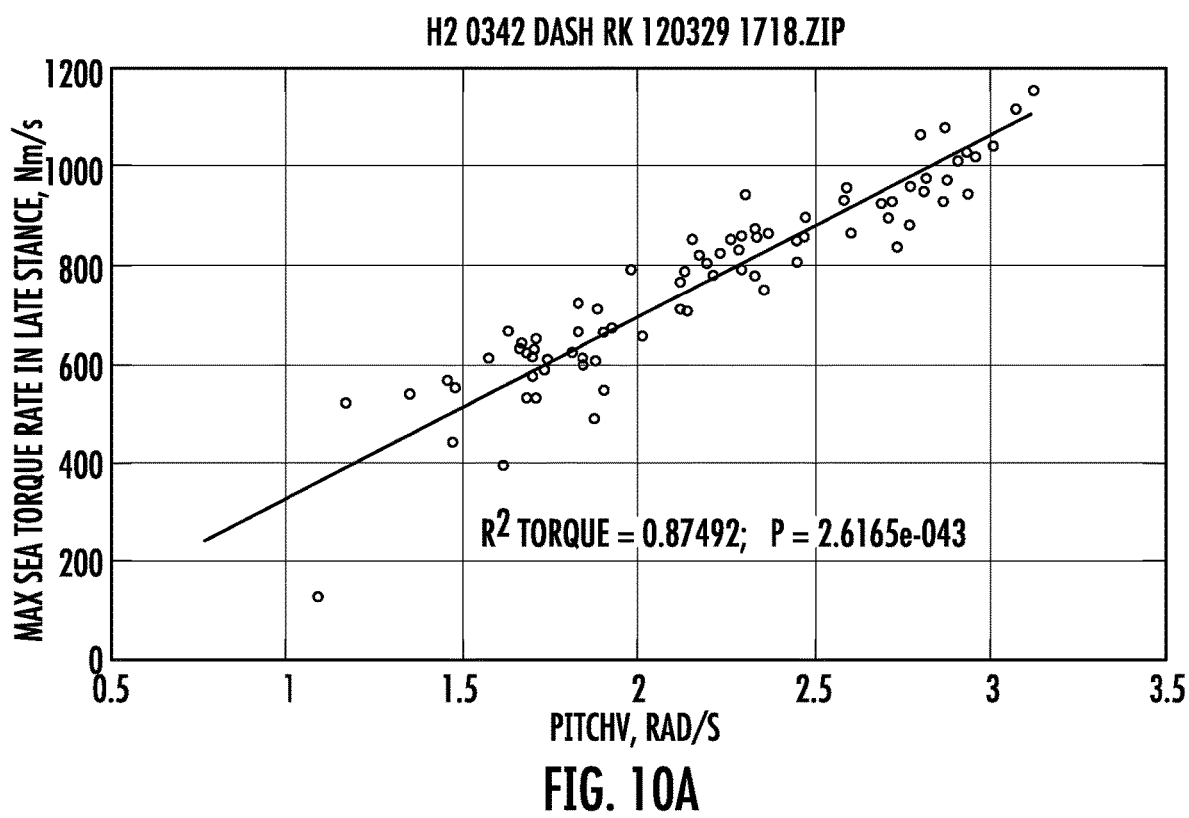
FIG. 10a illustrates a graph of data correlating torque rate with pitch rate in accordance with some embodiments.
Figure 10B:
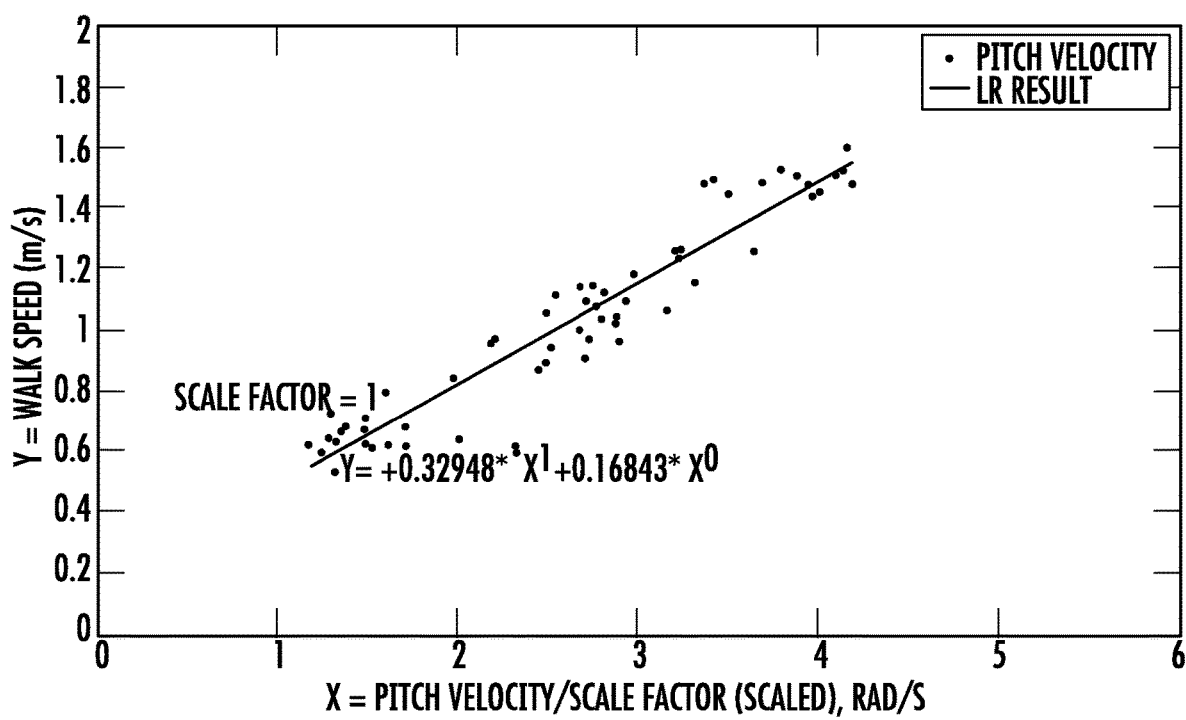
FIG. 10b depicts a graph of data correlating pitch rate with walking speed in accordance with some embodiments.

Accordingly, for each type of state transition, a threshold would be crossed (e.g., when the measured or sensed torque is greater than or less than a particular set torque value, within a certain period of time) that triggers transition from one state to Walking-Speed Referenced Reflex The device may use the maximum, rate-of-change in SEA torque ($\dot{\Gamma}_{SEA}$) as measured in Late Stance as an estimation (or surrogate) for instantaneous walking speed. FIG. 10a illustrates data that shows a linear relationship that exists between $\dot{\Gamma}_{SEA}$ and the tibia pitch rate, $\dot{\Psi}$. The tibia pitch rate at mid-stance (after the foot flat condition) is further known, through experimentation, to be proportional to leg-length normalized walking speed, as shown in FIG. 10b and as discussed in U.S. patent application Ser. No. 13/079,564. This estimation of walking speed may be computed just before use in Late Stance Power to inform the reflex parameter modulation.

Figure 10C:
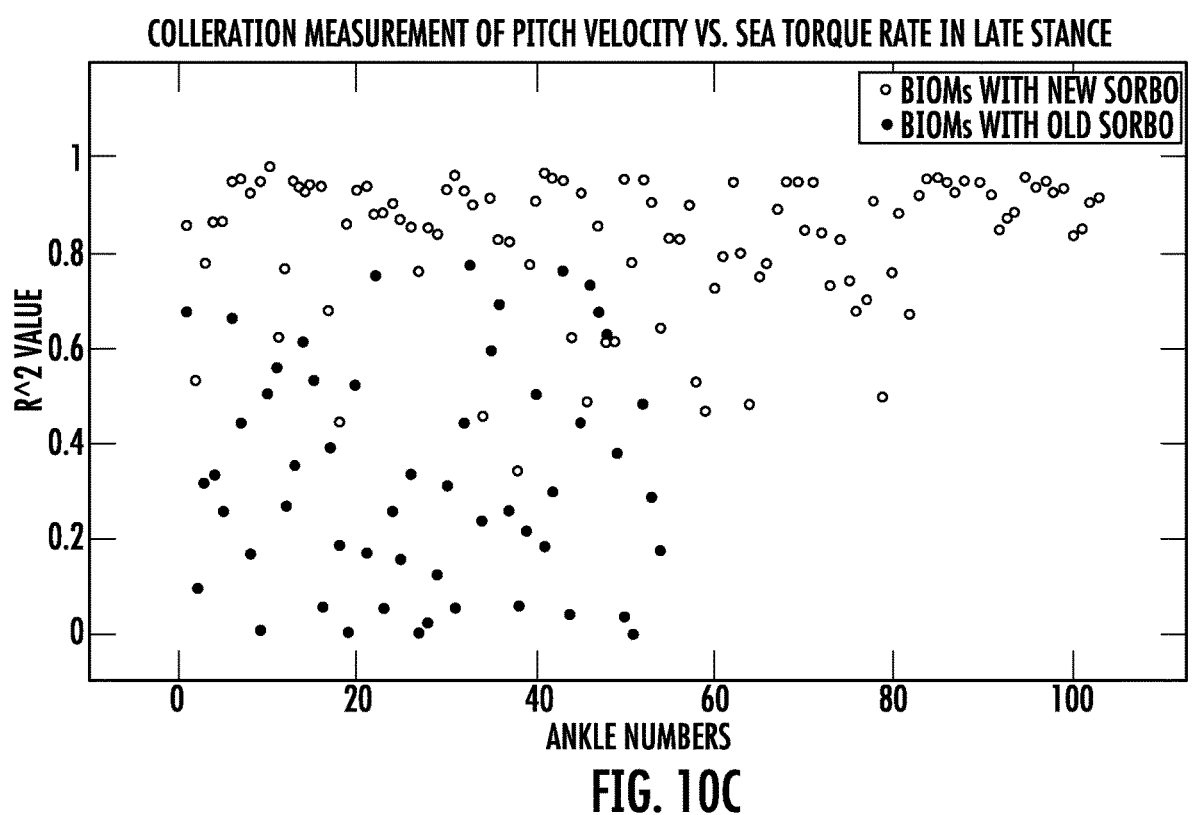
FIG. 10c shows a graph of the correlation data between torque rate and pitch rate in accordance with some embodiments.

The graph shown in FIG. 10c reports a high degree of correlation ($R^2$) of pitch velocity vs. SEA torque rate during Late Stance that exists across a broad population of production units and walkers (see circles), as measured in a standard walkabout test used to create a Dashboard.

Such studies have shown that $\dot{\Gamma}_{SEA}$ is not invariant across a population of wearers, even when normalized by, for example, peak torque at a self-selected walking speed. So, in one embodiment, $\dot{\Gamma}_{SEA}$ is observed for each specific wearer—both at the fastest achievable walking speed and at the slowest desired walking speed. At each speed, preferred values for torque gain, $p_{ff}(\dot{s})$, and torque exponent, $N(\dot{s})$, may be determined by tuning—thereby determining values/ ranges for various parameters, such as $p_{ff_{slow}}$, $N_{slow}$, $p_{ff_{fast}}$, $N_{fast}$. With these parameters in hand, a basis is provided through which the reflex response may be blended across a range of walking speeds. By replacing $\dot{s}$ with $\dot{\Gamma}_{SEA}$, the following blended reflex equations may be used:

Method I: Blended Torque Models $$\tau_{slow} = P_{ff_{slow}}\left(\frac{\Gamma_{ankle}}{\Gamma_0}\right)^{N_{slow}}$$

$$\tau_{fast} = P_{ff_{fast}}\left(\frac{\Gamma_{ankle}}{\Gamma_0}\right)^{N_{fast}}$$

$$\tau_{motor} = c_1(\dot{\Gamma})\tau_{slow} + c_2(\dot{\Gamma})\tau_{fast}$$

$$c_2 = 1 - c_1$$

$$c_1(\dot{\Gamma}) = 1 \text{ for } \dot{\Gamma} \leq \dot{\Gamma}_{slow}$$

$$c_1(\dot{s}) = 0 \text{ for } \dot{\Gamma} \geq \dot{\Gamma}_{fast}$$

$$c_1(\dot{\Gamma}) = \frac{(\dot{\Gamma}_{fast} - \dot{\Gamma})}{(\dot{\Gamma}_{fast} - \dot{\Gamma}_{slow})} \text{ for } \dot{\Gamma}_{slow} < \dot{\Gamma} < \dot{\Gamma}_{fast}$$

Method II: Blended Coefficients $$\tau_{motor} = \tilde{P}_{ff}(\dot{s})\left(\frac{\Gamma_{ankle}}{\Gamma_0}\right)^{\tilde{N}(\dot{\Gamma})}$$

Where $$\tilde{P}_{ff}(\dot{\Gamma}) = c_1(\dot{\Gamma})P_{ff}(\dot{\Gamma}_{slow}) + c_2 P_{ff}(\dot{\Gamma}_{fast})$$

and $$\tilde{N}(\dot{\Gamma}) = c_1(\dot{\Gamma})N\dot{\Gamma}_{slow}) + c_2 N(\dot{\Gamma}_{fast})$$

where $c_1$ and $c_2$ are defined as in Method I.

Where the subscript, SEA, on $\dot{\Gamma}_{SEA}$, is removed to simplify the notation.

Device Extensions

It should be appreciated that while device control architectures in accordance with the present disclosure have been applied to an artificial (bionic) ankle device with a hardstop, the hardstop functionality may be replaced by a physical, unidirectional or bi-directional element, parallel elastic element, a virtual, SEA-applied, parallel elastic element, or other suitable component. For example, in either case the hard stop torque, $\Gamma_{hs}$, may be replaced by a parallel elastic element torque, $\Gamma_{PE}$, where $\Gamma_{PE}$ is calibrated in manufacturing to determine the torque displacement characteristics of the physical or virtual elasticity.

Further, while device control architectures described herein have been applied to artificial ankle prostheses, concepts presented here may be extended for application in orthotic, exoskeletal, humanoid ankles, or other appropriate devices. And, while the device control architectures herein have been applied to artificial ankle applications, the techniques applied here may also be extended for use in accordance with other lower-extremity applications, for example, in the knee and hip.

Further Embodiments and their Implementation for Prosthetic or Orthotic Ankle Devices Embodiments of bionic leg devices, such as the BiOM$^{T2}$ system produced by iWalk, Inc., may employ five states— Early Stance (ES; State 4), Late Stance (LS; State 5), Late Stance Power (LSP; State 6), Early Swing (ESW; State 2) and Late Swing (LSW; State 3)—that align with the human biomechanical gait cycle states controlled plantar flexion (CP), controlled dorsiflexion (CD), powered plantar flexion (PP), Early Swing (ESW) and Late Swing (LSW), respectively. The present disclosure reviews various details of control actions within each state and describes the state transition logic that causes entry into the state.

Early Stance (ES) Control Action In ES (State 4), for some embodiments, the SEA applies a lightly-damped, torsional spring response in accordance with the human biomechanical joint response in Controlled Plantar Flexion. The impedance as applied by the SEA motor torque, $\tau_m$, is comprised of a time-varying spring, $k_{es}(l)$, and a time-varying damping component, $b_{es}(t)$. The "virtual spring" joint equilibrium, $\theta_{es}$, is the ankle angle as captured at ES entry. In some cases, one or more variables (e.g., spring constant, damping component, joint equilibrium, gain, exponent, etc.) of the motor torque may be time-dependent and/or may exhibit a time decay-type behavior (e.g., exponential, linear, piecewise, etc.). The actuator may apply an exponential decay to the stiffness component in order to make the ankle increasingly more compliant as the state progresses— to emulate human biomechanics while walking slowly, including on steep or uneven terrain. The ES control action may be modeled as follows:

$$\tau_m = \frac{\text{Lightly-damped spring response with exponential stiffness decay}}{k_{es}(t)(\theta - \theta_{es}) - b_{es}\dot{\beta}}$$

where
$\tau_m$ is the motor torque,
$\theta$ is the joint angle,
$\beta$ is the SEA motor angle,
And where,
$\tau_{es}\dot{k}_{es}(t)+k_{es}(t)=k_{es_\infty}$ applies an exponential stiffness decay with time constant, $\Gamma_{es}$ $\theta_{es}-\theta(t-0)$,
In some embodiments, the following second-order relation may be used to model exponential stiffness decay:
$\tau_{k_{es}}^2\ddot{k}_{es}(t)+2\tau_{k_{es}}\dot{k}_{es}(t)+k_{es}(t)=k_{es_\infty}$
t=time since ES entry
$k_{es}(0)=k_{es_0}$,
$b_{es}(0)=b_{es_0}$
To those skilled in the art, other linear or non-linear differential equations can be applied to accomplish this decay function.
As provided in the equation above, the stiffness decays to $k_{es_\infty}$ with a time constant, $\tau_{es}$—e.g., about 200 milliseconds, or between 100-500 milliseconds. In some embodiments, the time constant may be set (e.g., optimized) so as to allow the ankle to conform to the ground surface while the wearer walks slowly down an incline. Examples of these are included in Table 3 below.

Early Stance (ES) Entry State-Transition Details
Late Swing (LSW)-to-Early Stance (ES) Transition In some embodiments, the state transition into ES from LSW may occur when a foot-strike is detected—for example, by presence of a large or increasing heel load ($L_{3-4_B}$ or $L_{3-4_C}$, respectively) as measured by $\Gamma_{SEA}$; a large toe load ($L_{3-4_A}$) as measured by $\Gamma_{hard\ stop}$; or the extended presence of a large ankle load ($L_{3-4_D}$) as measured by $\Gamma_{ankle}$. That said, to detect these conditions reliably, a "guard condition" may first be applied to the logic to reject any such noise in $\Gamma_{SEA}$ and $\Gamma_{hard\ stop}$ that may arise during the swing phase. This may be a result of the SEA torque applied to achieve the ankle trajectory and a possible collision with the hardstop during the time interval. The LSW-ES guard logic (GUARD) may be implemented as follows:

GUARD=(($t_{lsw}$<100 msec) AND ($\Gamma_{hard\ stop}$<0.58$\Gamma_0$))
OR (($t_{lsw}$<250 msec) AND (TransitionEnabled=FALSE) AND ($\Gamma_{hard\ stop}$<0.58$\Gamma_0$))

Or, alternatively, the GUARD logic may be employed according to the following relation:

GUARD=(($t_{lsw}$<100) AND ($\Gamma_{hard\ stop}$<0.58$\Gamma_0$)) OR
(($t_{lsw}$<250 msec) AND
(AnkleNotReturned=TRUE) AND
($\Gamma_{hard\ stop}$<0.58$\Gamma_0$))

In the event that GUARD is FALSE, the LSW to ES state transition (3-4) logic may be as follows:

$L_{3-4} L_{3-4_A}$ OR $L_{3-4_B}$ OR $L_{3-4_C}$ OR $L_{3-4_D}$ where $L_{3-4_A}$: ($\Gamma_{hard\ stop}$>45 Nm) AND ($\Gamma_{hard\ stop}(t)-\Gamma_{hard\ stop}(t-40\ msec)$>11 Nm).

$L_{3-4_B}$: (min($\Gamma_{SEA_{es}}$) detected) AND
(Motor is in the READY state) AND
($\dot{\Gamma}_{SEA}$<−50 Nm/s) AND
($\Gamma_{SEA}$<min($\Gamma_{SEA_{es}}$)−2 Nm).
$L_{3-4_C}$: (min($\Gamma_{SEA_{es}}$) detected) AND
($\dot{\Gamma}$<−180 Nm/s) AND
($\Gamma_{SEA_{[t,t-6\ msec]}}$<min($\Gamma_{SEA_{es}}$)−1 Nm) AND
($\Gamma_{SEA}(t)-\Gamma_{SEA}(t-6\ msec)$<−0.5 Nm) AND
($\Gamma_{SEA}(t)-\Gamma_{SEA}(t-10\ msec)$<−1.0 Nm).
$L_{3-4_D}$: ($t_{LSW}$>1500 msec) AND
(TransitionEnabled=TRUE) AND
($\Gamma_{ankle}(t)$>30 Nm) ∀ t where $t_{LSW}$−300 msec≤t≤$t_{LSW}$.
where
$l_{LSW}$ is the elapsed time since LSW entry,
$\Gamma_{SEA}(t)$, and $\Gamma_{hard\ stop}(t)$ are the SEA and Hard Stop torque at time, t, respectively, READY is a signal indicating that the motor controller processor has completed the trajectory return,
Transition-Enabled is a motor state indicating that the motor controller has completed the trajectory return instruction and that the motor temperature measurement has been completed.
AnkleNotReturned is a check to indicate whether the ankle has returned to an initial state and has suitably dorsiflexed.
min($\Gamma_{SEA_{es}}$) is the first validated minimum of SEA torque while GUARD=FALSE.
$\Gamma_{SEA_{[t,t-n\ msec]}}$ is notation for the mean of $\Gamma_{SEA}$ computed using samples from the prior n milliseconds referenced to the current time, t.
$\Gamma_{ankle}(t)=\Gamma_{SEA}(t)+\Gamma_{hard\ stop}(t)$ is the total ankle torque.
For various embodiments presented herein, it is noted that the ES, LS, LSP, ESW and LSW control response may be invariant with respect to which logic condition—$L_{3-4_A}$, or $L_{3-4_B}$, $L_{3-4_C}$ or $L_{3-4_D}$—causes the state transition into ES.

Late Stance (LS)-to-Early Stance (ES) Transition
In some cases, for instance, when the wearer stops in mid-stance, the control system may transition from LS (State 5) back to ES (State 4), so that the ankle state responds in accordance with the true walking cycle state. The $L_{5-4}$ transition may be informed by a negative change in $\Gamma_{SEA}$ after the elapsed time in LS exceeds 500 msec and may be summarized as follows:

$L_{5-4}$=(($\Gamma_{SEA}(l_{LS})$−max$_{LS}(\Gamma_{SEA})$)<−5 Nm) AND (($\Gamma_{SEA}(t_{LS})-\Gamma_{SEA}(t_{LS}-10\ msec)$)<−0.5 Nm) AND
($t_{LS}$>500 msec)

where
$t_{LS}$ is the elapsed time since entering LS
$\max_{LS}(\Gamma_{SEA}(t))$ is the maximum value of $\Gamma_{SEA}(t)$ in LS.

Early Stance (ES)-to-Early Stance (ES) Transition

In some cases, for instance, when the wearer stops in ES then begins to walk again, the impedance and equilibrium are reset to appropriate values for foot strike to occur. Accordingly, the device may be configured to re-enter the ES state based upon detection of an $L_{4-4}$ transition. This transition may be informed by a negative change in $\Gamma_{SEA}$ after the elapsed time in ES exceeds 500 msec, and may be summarized as follows:

$L_{1-4} = (\Gamma_{SEA}(t_{es}) - \max_{ES}(\Gamma_{SEA})) < -5$ Nm) AND $((\Gamma_{SEA}(t_{ES}) - \Gamma_{SEA}(t_{ES} 10$ msec$)) << 0.5$ Nm) AND $(t_{ES} > 500$ msec)

where
$t_{ES}$ is the elapsed time since entering ES
$\max_{ES}(\Gamma_{SEA}(t))$ is the maximum value of $\Gamma_{SEA}(t)$ in ES.

Late Stance Power (LSP)-to-Early Stance (ES) Transition

In some cases, the entry into ES from LSP may occur if the ankle is back-driven into LSP (LSPRegen)—to protect the wearer in the event that the state machine does not detect a walking state transition out of LSP, for example, to ESW. Because there is no stiffness in opposition to a plantar flexion displacement in LSP, the expected ES impedance (heel-strike stiffness) may be absent in a heel-strike event and would thereby surprise the wearer. That is, if there is no stiffness in the ankle after LSP occurs, the system may, by default, set its parameters to the ES stance in preparation for the device in striking the ground.

LSP-to-ES "LSPRegen" Transition

The LSP-ES LSPRegen transition may occur when $L_{6-4_{LSPRegen}}$: per the logic equation:

$L_{6-1_{LSPRegen}} = \overline{\text{Guard}_{Regen}}$ AND $L_{6-4_{RegenA}}$ $\text{Guard}_{Regen} = (\max_{LSP}\Gamma_{SEA} - \Gamma_{SEA}(0) < 10$ Nm)

$L_{6-1_{Regen}} = \dot{\Gamma}_{SEA}(t) < -150$ Nm AND $(\Gamma_{SEA}(t) - \Gamma_{SEA}(t-10$ msec$)) < -1.2$ Nm AND $\Gamma_{hard\ stop}(t) < 1$ Nm where
$t = t_{LSP}$ is the elapsed time in LSP and
$\max_{LSP}\Gamma_{SEA}$ is the maximum value of the SEA torque since entry into LSP.

Late Stance (LS) Control Response

In various embodiments of a controller for artificial leg devices presented herein, LS (State 5) bridges the control response between ES and LSP—typically between foot flat and hard stop engagement. In LS, the actuator continues to apply a damped, torsional spring response so as to correspond with the early CD response in human biomechanics. Mathematically, the LS response is captured in Eq. 1.

It is well-understood that the spinal reflex arc connecting the Achilles tendon stretch and the soleus (calf) muscle contraction employs positive force feedback—both torque and torque derivative are employed to amplify the reflex response in the contractile element (muscle). To mimic this reflex arc in artificial leg devices according to the present disclosure, the peak rate of change of ankle torque in LS, $\dot{\Gamma}_{ankle_{ls}}$, may be used as input for the strain-rate component of the reflex and spring dynamics applied in LSP by the SEA—itself the bionic, artificial muscle-tendon unit in the BiOM ankle. Here, $$\dot{\Gamma}_{ankle_{ls}} = \{c_{SEA}\max_{ls}(\dot{\Gamma}_{SEA}) + c_{hs}\max_{ls}(\dot{\Gamma}_{hard\ stop})\}_{ls} \quad (1)$$

where
$\max_{ls}(\cdot)$ denotes the maximum of a function during LS $$c_{SEA} = \frac{\int_{ls}|\Gamma_{SEA}|dt}{\int_{ls}(|\Gamma_{SEA}| + |\Gamma_{hard\ stop}|)dt}$$

$$c_{HS} = \frac{\int_{ls}|\Gamma_{hard\ stop}|dt}{\int_{ls}(|\Gamma_{SEA}| + |\Gamma_{hard\ stop}|)dt}$$

and
$\int_{ls}(\cdot)dl$ denotes the time integral over LS.

Late Stance (LS) Entry State-Transition Details

In some embodiments, ES entry into LS (State 5) is the only state transition into LS. The LS transition may occur if either a large toe load ($L_{4-5_A}$) or heel load ($L_{4-5_B}$) is sensed by $\Gamma_{hard\ stop}$ and $\Gamma_{SEA}$ respectively. An example of the mathematical formulation of the state transition (4-5) is described below.

$L_{4-5} = L_{4-5_A}$ OR $L_{4-5_B}$ where $$L_{4-5_A} = \overline{(\Gamma_{hard\ stop} > 0.58\Gamma_0) \text{ OR } ((\Gamma_{hard\ stop} > 45\ Nm) \text{ AND } (\Gamma_{hard\ stop}(t) - \Gamma_{hard\ stop}(t-40\ msec)) > 11\ Nm)}^{\text{Toe-load term}}$$

$$L_{4-5_B} = \overline{(\dot{\Gamma}_{SEA} > 0) \text{ AND } \left(\Gamma_{SEQ[t,t-10\ msec]} > 10\frac{Nm}{\sec}\right)}^{\text{Heel-load term}}$$

$L_{1-5} = L_{4-5_A}$ OR $L_{4-5_B}$

Where $$L_{4-5_A} = \overline{(\Gamma_{hard\ stop} > 45\ Nm)}^{\text{Toe-load term}}$$

$$L_{405_B} = \overline{(\dot{\Gamma}_{SEA} > 0) \text{ AND } \left(\Gamma_{SEA[t,t-10\ msec]} > 20\frac{Nm}{msec}\right)}^{\text{Heel-load term}}$$

It should be appreciated that the control response in LS, LSP, ESW and LSW may be invariant with respect to which logic condition—$L_{4-5_A}$ or $L_{4-5_B}$—causes the 4-5 transition.

Late Stance Power (LSP) Control Response

In some embodiments, the actuator response in LSP (State 6) is comprised of two terms—a unidirectional torsional spring, $k_{lsp}$, with equilibrium at a torque-rate-dependent plantar flexion angle, $\theta_{pp}$, and a torque-rate-dependent reflex. The reflex term applies a positive force-feedback response that comprises two components—a torque-rate dependent gain, $p_{ff}(\dot{\Gamma}_{ankle_{ts}})$, and a non-linear, normalized joint torque feedback, $$\tau_m = \max(\overbrace{-k_{lsp_{max}}(\theta - \theta_{pp}(\dot{\Gamma}_{ankle_{ls}}))}^{\text{Torsional spring with equilibrium at }\theta_{pp}}, \overbrace{p_{ff}(\dot{\Gamma}_{ankle_{ls}})\Gamma_{ankle}^{N(\dot{\Gamma}_{ankle_{ls}})}}^{\text{Torque-rate dependent reflex}}) \quad (2)$$

with a torque-rate dependent exponent, $N(\dot{\Gamma}_{ankle_{ls}})$. In some embodiments, the torque gain may range between 0 and 200 Nm, and the torque exponent may range between 1 and 5. Here, $\dot{\Gamma}_{ls}$ is the peak rate of change of joint torque in LS, as described in the previous section that addresses late stance. Both $p_{ff}$ and N may be piecewise-continuous, linear functions, defined each by their values at a slow speed and a high speed torque rate—$\dot{\Gamma}_{ankle_{ls}slow}$ and $\dot{\Gamma}_{ankle_{ls}fast}$ respectively. At torque rates beyond this range both $p_{ff}$ and N may be held constant. In some embodiments, $p_{ff}$ and/or N are time-dependent functions, for example, that exhibit an exponential decay behavior.

Mathematically, the LSP control response may be defined in Equation 2, shown below.

$$\tilde{\Gamma}_{ankle} = \frac{\Gamma_{SEA} + \Gamma_{hard\ stop}}{\Gamma_0},$$

where $\tau_m$ is the SEA motor torque $k_{lsp_{max}}$ is a torsional spring stiffness defined as the maximum of a quantity equal to the torque-rate dependent reflex torque divided by the value of $\theta - \theta_{pp}$.

$\theta_{pp}$ is a plantar flexed torsional spring equilibrium that is a piecewise, continuous linear function of $\dot{\Gamma}_{ankle_{ls}}$ $p_{ff}$ and N are each a piecewise, continuous linear function of $\dot{\Gamma}_{ankle_{ls}}$ as defined above, or may be time-dependent functions that may range between 0-200 Nm and between 1-5, respectively.

$$\tilde{\Gamma}_{ankle} = \frac{\Gamma_{SEA} + \Gamma_{hard\ stop}}{\Gamma_0}$$

is the normalized ankle torque
where
$\Gamma_0$ is a normalizing torque equal to $$1.7 \frac{Nm}{kilogram} m_{wearer}$$

where $m_{wearer}$ is the wearer mass in kilograms.

Figure 24:
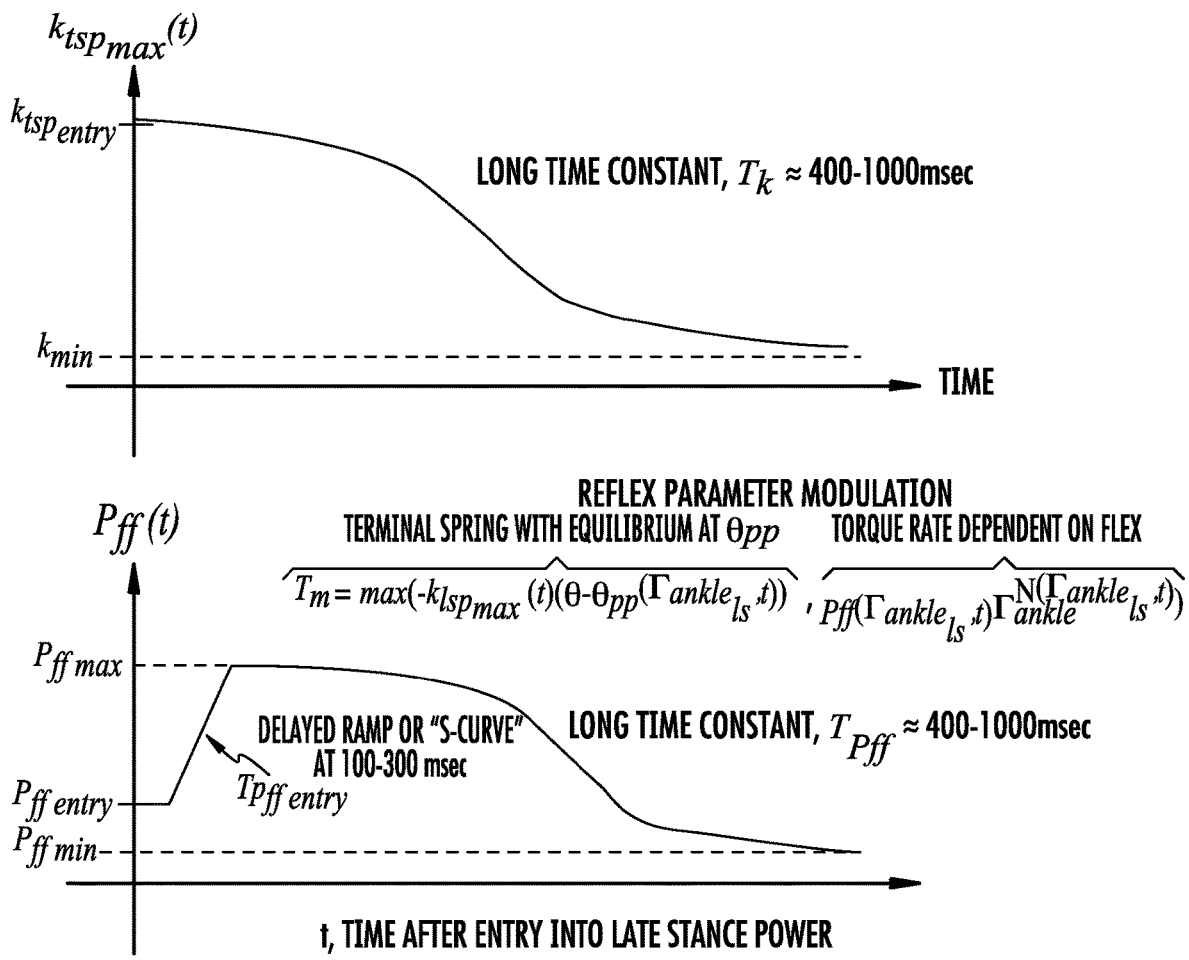
FIGS. 24-25 illustrate graphs of reflex parameter modulation functions in accordance with some embodiments.
Figure 25:
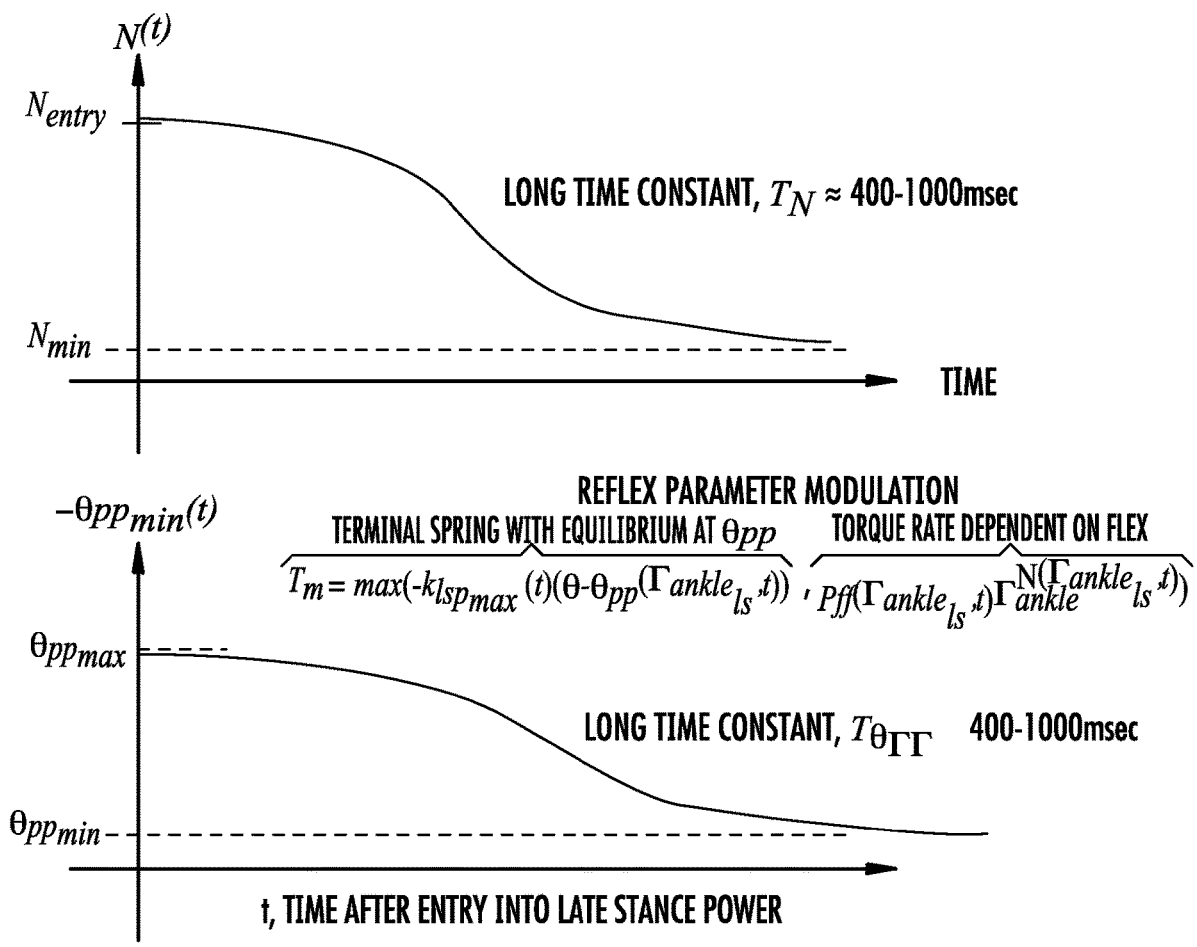

In some cases, one or more of the parameters of an actuated torque are time-dependent functions that exhibit time-decay behavior (e.g., exponential, linear, piecewise, etc.). For instance, $k_{pp}, \theta_{pp}, p_{ff}$ and/or N may exhibit exponential decay behavior over time, so as to provide for a soft reflex response or gradual joint equilibrium transitions. As an example, during LSP, the wearer may decide that he/she would like to ease in or out of powered plantar flexion. If the gain and/or exponent of the torque reflex response exhibits time-dependent decay, the wearer may experience a relatively smooth reflex response than may otherwise be the case without the decay behavior. Or, $\theta_{pp}$ may also exhibit time-dependent decay behavior, resulting in relatively smooth transitions from one state to another. Any suitable time-dependent behavior may be employed, such as those functions described for various embodiments of the present disclosure. FIGS. 24-25 show examples of suitable reflex parameter modulation relationships.

Late Stance Power (LSP) Entry State-Transition Details

In some embodiments, the LS to LSP transition (5-6) may occur when the toe-load torque exceeds a programmable threshold. Mathematically, the $L_{5-6}$ transition may occur when $\Gamma_{hard\ stop} > 5$ Nm.

Early Swing Control Response

In some embodiments, the ESW (State 2) control response of the artificial leg device mimics the damped, second-order, spring-mass response of the early swing phase in human walking biomechanics—this response restores the ankle from the toe-off position at the terminus of powered plantar flexion to its neutral position, in anticipation of the foot strike in the next gait cycle. Typically, the time constant, $\tau_{esw}$, of this response is approximately 50 milliseconds, but may vary appropriately.

In ESW, an overdamped, second-order equilibrium trajectory, $\theta_0(t)$, may be applied to return the joint to a fixed neutral position, $\theta_{esw}$—a position that may be invariant to all biomechanical modalities including, but not limited to, terrain, walking speed, and toe-off angle. A damped ($b_{esw}$) and spring ($k_{esw}$) impedance may be applied in relation to this equilibrium trajectory. Feedforward of the estimated motor torque may be used to eliminate response lag due to motor/drive-train inertia and damping. The mathematical formulation of the ESW control response with inertia-only feedforward may be summarized in Equation 3 shown below.

$$\tau_m = \overbrace{-k_{esw}(\theta(t) - \theta_0(t)) - b_{esw}(\dot{\beta} - \dot{\theta}_0(t))}^{\text{Lightly-damped impedance referenced to over-damped, second-order trajectory}} + \overbrace{J_{\beta_m}\ddot{\beta}}^{\text{Motor inertia feedforward}} \quad (3)$$

and $$\overbrace{\tau_{esw}^2\ddot{\theta}_0 + 2\tau_{esw}\dot{\theta}_0 + \theta_0 = \theta_{esw}}^{\text{Over-damped, second-order, equilibrium trajectory}}$$

where
$\tau_m$ is the SEA motor torque,
$\tau_{esw}$ is the time constant of the over-damped, second-order response,
$\theta_0(0)$ is the toe-off angle, initialized to $\theta(t)$ at ESW entry (LSP Exit),
$\beta$ is the SEA motor angle reflected at the ankle joint and
$\theta_{esw}$ is the invariant, neutral position destination for all ESW trajectories
$J_{\beta_m}$ is the motor inertia reflected onto the joint Early Swing (ESW) Entry State Transition Logic Transitions into ESW may normally originate from LSP, as described in the following section that addresses the late stance power to early swing transition. Transitions into ESW can originate from ES when the wearer lifts the foot off the ground, as described in the section that addresses ES-to-ESW at Foot-off.

Late Stance Power (LSP)-to-Early Swing (ESW) Transition

The LSP-ESW transition may be defined by either a toe-off ($L_{6-2_{toe-off}}$) or a foot-off event $L_{6-2_{foot-off}}$) while in LSP.

LSP-to-ESW at Toe-Off

Toe-off may occur when the ankle torque, $\Gamma_{ankle}$, drops below a threshold close to zero.

The following guard, pre-trigger, and state transition conditions may be applied in succession to accomplish the LSP-ESW (6-2) transition by toe-off.

Toe-Off Guard Condition Details

The LSP-ESW by toe-off transition may be halted until GUARD has transitioned from TRUE to FALSE.

$$GUARD = (t_{lsp} < 200 \text{ , sec}) \text{ AND } \Big(\Gamma_{hard\ stop} >$$

$$0 \text{ OR } \overline{\dot{\Gamma}}_{SEA[t,t-10\ msec]} > -200\frac{Nm}{\sec} \text{ OR } \max_{lsp}(\Gamma_{hard\ stop}) < 20\ Nm\Big)$$

Toe-Off Pre-Trigger Details

Before detecting the LSP-ESW toe-off transition, compute the following: ToeOffTransitionEnable–$\Gamma_{ankle}<0.5$ $\max_{lsp}(\Gamma_{hard\ stop}(t))$ AND $\Gamma_{ankle}<25$ Nm if ToeOffTramsitionEnable=TRUE then capture $t_{enabled}$

Toe-Off Transition (6-2) Logic $L_{6-2_{toe-off}}$=ToeOffTransitionEnable AND ($\Gamma_{ankle}<10$ Nm OR t–$1_{enabled}\geq 20$ msec)

where in the above, $t_{lsp}$ is the time since LSP entry $\max_{lsp}(\Gamma_{hard\ stop}(t))$ is the maximum value of hard stop torque in LSP prior to $t_{lsp}$ $\overline{\dot{\Gamma}}_{SEA[t,t-10\ msec]}$ is the mean value of SEA torque rate over the past 10 milliseconds.

As a result, the LSP to ESW transition can occur when $L_{6-2}$ is TRUE.

LSP-to-ESW at Foot-Off

The "foot-off" condition—$L_{6-2_{foot-off}}$—may be informed by a rapid drop in both SEA and Hard Stop torque, which may be summarized as follows:

$L_{G-2_{foot-off}}=(L_{6-2_{foot-offA}} \text{ OR } L_{6-2_{foot-offB}} \text{ OR } L_{6-2_{foot-offC}} \text{ OR } L_{6-2_{footoffD}}) \text{ AND } (t_{lsp}>1600\ msec)$ $L_{6-2_{foot-offA}}=\Gamma_{SEA}<0$ AND $\Gamma_{SEA}(t)-\Gamma_{SEA}(t-10\ msec)<-1$ Nm AND $\Gamma_{hard\ stop}<30$ Nm AND $\Gamma_{hard\ stop}(t)-\Gamma_{hard\ stop}(t-40\ msec)<-11$ Nm $L_{6-2_{foot-offB}}=\dot{\Gamma}_{SEA}$–180 Nm/sec AND $\Gamma_{hard\ stop}<30$ Nm AND $\Gamma_{hard\ stop}(t)-\Gamma_{hard\ stop}(t-40\ msec)<-5$ Nm $L_{6-2_{foot-offC}}=\dot{\Gamma}_{SEA}<-50$ Nm/sec AND $\Gamma_{hard\ stop}<30$ Nm AND $\Gamma_{hard\ stop}(t)-\Gamma_{hard\ stop}(t-40\ msec)<<11$ Nm.

$L_{6-2_{foot-offD}}=\dot{\Gamma}_{SEA}<-50$ Nm/sec AND $\Gamma_{hard\ stop}<50$ Nm AND $\Gamma_{hard\ stop}(t)-\Gamma_{hard\ stop}(t-40\ msec)<-22$ Nm where $t=t_{LSP}$ is the elapsed time since entry into LSP

ES-to-ESW at Foot-Off

The "foot-off" condition—$L_{4-2_{foot-off}}$—may be informed by a rapid drop in SEA and Hard Stop torque, as follows:

$L_{1-2_{foot-off}}=\overline{Guard_{foot-off}} \text{ AND } \{L_{1-2_{foot-offA}} \text{ OR } L_{1-2_{foot-offB}} \text{ OR } L_{1-2_{foot-offC}} \text{ OR } L_{4-2_{foot-offD}}\}$ $Guard_{foot-off}$=FromLSPRegen OR $t_{ES}<800$ msec $L_{4-2_{foot-offA}}=\Gamma_{SEA}<0$ AND $\Gamma_{SEA}(t)-\Gamma_{SEA}(t-10\ msec)<-1$ Nm AND $\Gamma_{hard\ stop}<30$ Nm AND $\Gamma_{hard\ stop}(t)-\Gamma_{hard\ stop}(t-40\ msec)<--11$ Nm $L_{1-2_{foot-offB}}=\dot{\Gamma}_{SEA}<-180$ Nm/sec AND $\Gamma_{hard\ stop}<30$ Nm AND $\Gamma_{hard\ stop}(t)-\Gamma_{hard\ stop}(t-40\ msec)<-5$ Nm $L_{4-2_{foot-offC}}=\dot{\Gamma}_{SEA}<-50$ Nm/sec AND $\Gamma_{hard\ stop}<30$ Nm AND $\Gamma_{hard\ stop}(l)-\Gamma_{hard\ stop}(l-40\ msec)<-11$ Nm $L_{1-2_{foot-offD}}=\dot{\Gamma}_{SEA}<-50$ Nm/sec AND $\Gamma_{hard\ stop}<50$ Nm AND $\Gamma_{hard\ stop}(l)-\Gamma_{hard\ stop}(l-40\ msec)<-22$ Nm where $t=t_{ES}$ is the elapsed time since entry into ES, FromLSPRegen is a flag set in ES to note that ES entry originated from LSP during an unexpected regeneration event in powered plantar flexion, $Guard_{foot-off}$ is a guard logic condition that blocks the transition if ES entry originated from the excessive regeneration event in LSP or if the elapsed time within ES is less than a pre-specified duration (800 milliseconds).

Late Swing (LSW) Control Response

In LSW after the ESW return to the neutral angle is completed, the SEA applies a lightly-damped, torsional spring response equivalent to that applied at ES entry. This ensures that the intended impedance to be applied at foot strike is instantiated before impact—thereby achieving response continuity that is insensitive to ES state transition delay. The mathematical formulation of the LSW response is captured in Equation 4.

$$\underset{\text{Lightly-damped ES response at equilibrium}}{\tau_m = \quad -k_{es_0}(0-0_{es_0})-b_{es_0}\dot{\beta}} \quad (4)$$

where $\beta$ is the motor angle as projected onto the joint angle from SEA kinematics In LSW, after the ESW return to the neutral angle is completed, the SEA may apply a lightly damped, torsional spring response with a spring constant, $k_{es}(t)$ that may be designed to decay exponentially, according to a second-order differential equation. Such a decay, while not limited to exponential behavior, may help to ensure that the intended impedance to be applied at foot strike is instantiated before impact thereby achieving foot-strike response continuity that is insensitive to ES state transition delay. Such a form of decay dynamics has the emergent property that stiffness decreases with increased walking speed. This property acts to reduce foot-strike stiffness while walking slowly down a steep slope, for instance. The joint equilibrium, $\theta_{es0}$, may be set to the ankle angle, at entry, $\theta(0)$. The mathematical formulation of the LSW response, including stiffness decay dynamics, is captured in the Equations 5 and 6 below.

$$\underset{\text{Lightly-damped ES response at equilibrium}}{\tau_m = \quad -k_{es}(t)(\theta-\theta_{es_0})-b_{es_0}\dot{\beta}} \quad (5)$$

$$\tau_{k_{es}}^2 \ddot{k}_{es}(t) + 2\tau_{k_{es}}\dot{k}_{es}(t) + k_{es}(t) = k_{es_\infty} \quad (6)$$

Where t is the time elapsed since LSW entry $\theta_{es_0}=\theta(0)$, the value at LSW entry $b_{es_0}$ is the fixed value of damping $\beta$ is the motor angle as projected onto the joint angle from SEA kinematics $\tau_{k_{es}}$ controls the stiffness decay, typically 200 milliseconds $k_{es}(0)=k_{es_0}$ $k_{es_\infty}$ is the terminal value of stiffness

Late Swing (LSW) Entry State-Transition Details

The ESW-LSW state transition may occur when the motor control processor reports that it is READY, thereby signifying that the ESW trajectory is completed, OR, for example, when $t_{esw}$>100 msec.

Late Swing (LSW) Entry from Early Stance (ES)

An ES-LSW transition can occur in cases where after an extended period in

ES (e.g., approximately two seconds) a possible ground impact is present as detected by a toe load ($L_{3-4_A}$), toe unload ($L_{3-4_B}$), or footstrike ($L_{3-4_C}$), as provided below.

$L_{4-3_A}$: Toe-Load Detected
($\Gamma_{hard\ stop}$>45 Nm) AND
($\Gamma_{hard\ stop}(t)-\Gamma_{hard\ stop}$(t−40 msec)<11 Nm).

$L_{4-3_B}$: Toe-unload Detected
(min($\Gamma_{SEA_{es}}$) detected) AND
(Motor is in the READY state) AND
($\dot{\Gamma}_{SEA}$<−50 Nm/s) AND
($\Gamma_{SEA}$<min($\Gamma_{SEA}$)−2 Nm).

$L_{4-3_C}$: Foot-Strike Detected
(min($\Gamma_{SEA_{es}}$) detected) AND
($\dot{\Gamma}_{SEA}$<−180 Nm/s) AND
($\Gamma_{SEA_{[t-6\ msec]}}$<min($\Gamma_{SEA_{es}}$)−1 Nm) AND
($\Gamma_{SEA}(t_{es})-\Gamma_{SEA}(t_{es}$−6 msec)<−0.5 Nm) AND
($\Gamma_{SEA}(t)-\Gamma_{SEA}$(t−10 msec)<−10 Nm).

Where
$t_{es}$ is the elapsed time since ES entry,
$\Gamma_{SEA}(t)$, and $\Gamma_{hard\ stop}(t)$ are the SEA and hard stop torque at time, t, respectively, READY is a motor state indicating that the motor controller processor is ready to accept commands.

min($\Gamma_{SEA_{es}}$) is the first validated minimum of SEA torque after ES entry.

Figure 11:
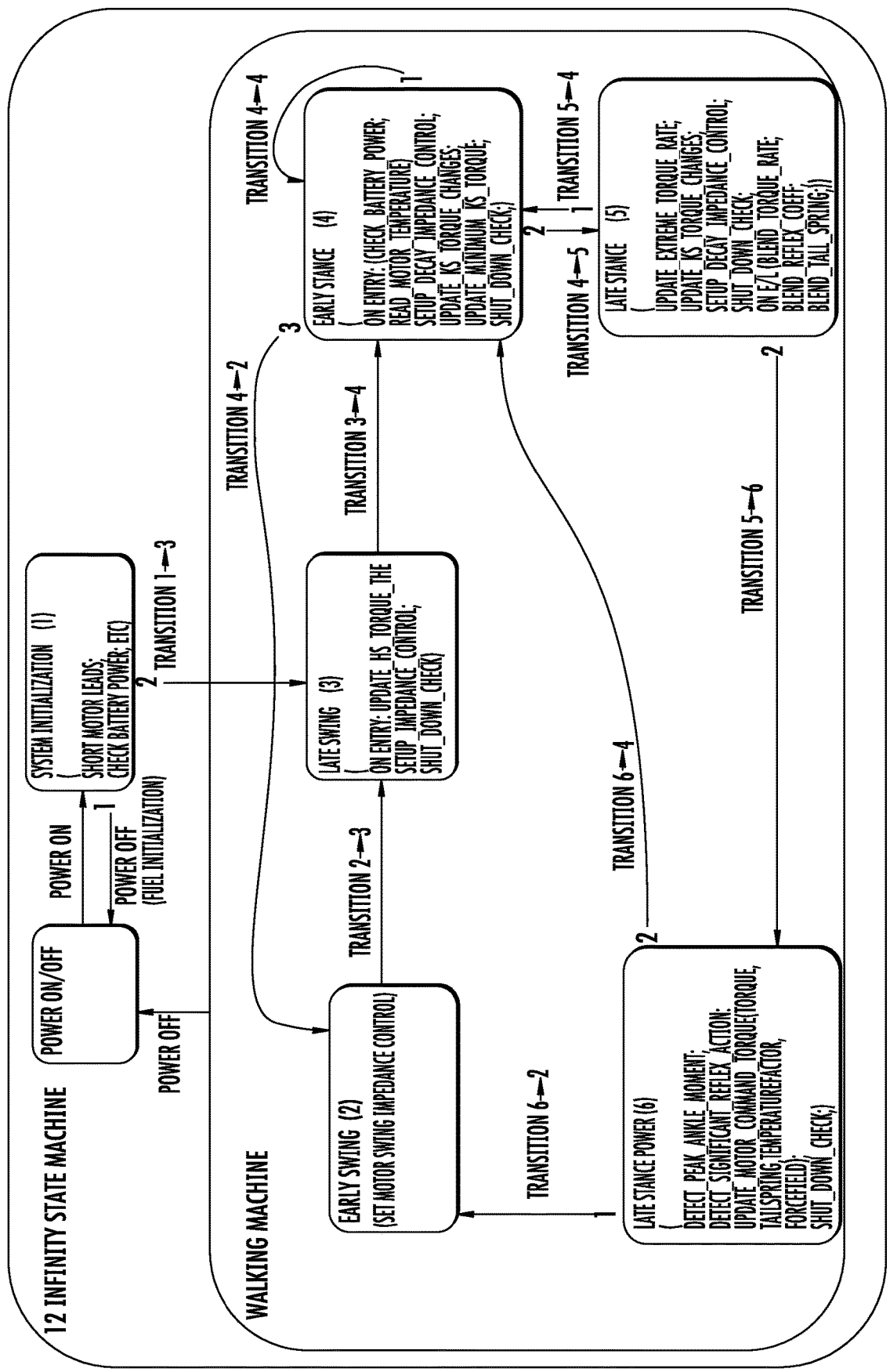
FIG. 11 depicts a schematic diagram of operation of an artificial leg device in accordance with some embodiments.

While description for each of the state transitions is provided above, Table 3 summarizes the state transition logic, including various non-limiting conditions and thresholds that are used for an embodiment of an artificial leg device, in accordance with the present disclosure. FIG. 11 provides a schematic that illustrates operation of an embodiment of an artificial leg device.

TABLE 3

State transition setup for an embodiment of an artificial leg device.
State Machine Transitions and Threshold Setup

| State & Transition | Transition Conditions | | Threshold Setting |
|---|---|---|---|
| In STATE 1 | Power On | | |
| 1 -> 3 | Systems initialization completed! AND 10 Nm > Ks_torque > −35 Nm | | Ks torque value |
| In STATE 2 | | | |
| 2 -> 3 | Timer > 100 ms | | Local Timer |
| In STATE 3 | | | |
| 3 -> 4 | Guard - No Transition | (Timer < 0.1 sec) AND (Ankle_Torque < 0.58 PCI) | Timer Large Ankle load |
| | | (Timer < 0.25 sec) AND (transition NOT enabled) AND (ankle_Torque < 0.58 PCI) | Timer Motor_ready_flag Large Ankle Load |
| | Transitions | ($1^{st}$_min Ks_torque found) AND (Ks_torque_dot < −180 Nm/s) AND (Ks_torque_rising_6 ms < 0.5 Nm) AND (Ks_torque_rising_10 ms < −1 Nm) AND (Ks_torque_6 ms_mean − $1^{st}$ min Ks_torque < −1 Nm) | Ks torque rate Ks_torque_changes_6 ms Ks_torque_changes_10 ms Ks_torque_drops_from min position |
| | | ($1^{st}$_min Ks torque found) AND (motor ready flag re-settled) AND (Ks_torque_dot < −50 Nm/s) AND (Ks torque_6 ms_mean − $1^{st}$ min Ks_torque < −2 Nm) | Ks torque rate Ks_torque_drops_from min position |
| | | (HS torque > HS_torque_Thr) AND (HS torque_rising in 40 ms > 11 Nm) | Hard Stop Torque HS torque rate_mean |
| | | (Timer > 1.5 sec) AND (transition enabled) AND (ankle Torque > 30 Nm) AND (High Ankle Torque Timer > 0.3 sec) | Local Timer Ankle Torque Timer_High Load |
| In STATE 4 | | | |
| 4 -> 5 | HS_torque > 0.58 PCI (HS_torque > HS_torque_Thr)AND (HS torque_rising in 40 ms > 11 Nm) (HS_torque < 15 Nm) AND (Ks_torque_max_drops_from_entry < −5 Nm) AND (Ks_torque_dot > 0) AND (Ks_torque_dot_10 ms_mean > 10 Nm/s | | Hard stop torque Hard Stop Torque HS torque rate_mean Hard stop Torque Ks torque max drops in 4 Ks_torque_rate Ks_torque_rate_10 ms_mean |

TABLE 3-continued

State transition setup for an embodiment of an artificial leg device.
State Machine Transitions and Threshold Setup

| | | | |
|---|---|---|---|
| 4 -> 4 | | (Timer > 0.5 sec) AND (Ks_torque_drops_in_10 ms < −0.5 Nm) AND (Ks_torque_max_drops_from_entry < −5 Nm) | Timer Ks_torque_changes_10 ms Ks torque max drops in 4 |
| 4 -> 2 | Guard - NO transition | State 6 to 4 protection ON Timer < 0.8 sec | Timer |
| | Foot unloading detector Transitions: | (HS_torque_40 ms_Ago < 30 Nm) AND (HS_torque_drops_in_ 40 ms < −5 Nm) AND (Ks_torque_dot < −180 Nm/s) | Hard Stop Torque 40 ms ago Hard Stop Torque drops moderately Ks torque rate |
| | | (HS_torque_40 ms_Ago < 30 Nm) AND (HS_torque_drops_in_40 ms < −11 Nm) AND (Ks_torque_dot <− 50 Nm/s) | Hard Stop Torque 40 ms ago Hard Stop Torque drops fast Ks torque rate |
| | | (HS_torque_40 ms_Ago < 30 Nm) AND (HS_torque_drops_in_40 ms < −11 Nm) AND (Ks_torque_rising_10 ms < −1 Nm) AND (Ks_torque < 0 Nm) | Hard Stop Torque 40 ms ago Hard Stop Torque drops fast Ks_torque_changes_10 ms Ks torque |
| | Transitions: | (HS_torque_40 ms_Ago < 50 Nm) AND (HS_torque_drops_in_40 ms < −22 Nm) AND (Ks_torque_dot < −50 Nm/s) | Hard Stop Torque 40 ms ago Hard Stop Torque drops very fast Ks torque rate |
| In STATE 5 | | | |
| 5 -> 6 | | HS torque > 5 Nm | Hard Stop Torque |
| 5 -> 4 | | (Timer > 0.5 sec) AND (Ks_torque_rising_in_10 ms < −0.5 Nm) AND (Ks_torque_drops_from_max_in_5 < −5 Nm) | Timer Ks_torque_changes_10 ms Ks_torque_max_changes |
| In STATE 6 | | | |
| 6 -> 2 | Guard - No Transition | (Timer < 0.2 sec) AND ((maxHS_torque < 20 Nm) OR (HS torque > 0) OR (Ks_torque_dot_10 ms_mean > −200 Nm/s)) | Timer Max HS torque HS torque Mean Ks torque rate in 10 ms |
| | Transitions | (Timer > 1.6 sec) AND (foot_unloading_detector) If (ankle_Torque < 0.5*PeakTorque) AND (ankle_torque < 25 Nm) Timer_delayed ++ End Transitions: (ankleTorque < 10 Nm) OR (Timer_delayed > = 0.02 sec) | Timer Low ankle torque Ankle total torque Low ankle Torque Timer |
| 6 -> 4 | | (maxKs_torque_rising_from_entry_in_6 < 10 Nm) AND (HS torque < 1 Nm) AND (Ks_torque_rising_in_10 ms < −1.2 Nm) AND (Ks_torque_dot < −150 Nm/s) | maxKs_torque_rising_from_entry_in_6 Hard Stop Torque Ks_torque_changes_10 ms Ks_torque_rate |

| State & Transition | Thesholds values | notes |
|---|---|---|
| In STATE 1 | | Systems initializing; {short motor leads; Check battery power; etc.} |
| 1 -> 3 | −35 Nm to 10 Nm | |
| In STATE 2 | | Setup motor swing impedance control{ } |
| 2 -> 3 | 0.1 sec | Time period given for foot return |
| In STATE 3 | | On entry{update HS_torque_Thr}; Setup impedance_control; Shut_down_check; |

TABLE 3-continued

State transition setup for an embodiment of an artificial leg device.
State Machine Transitions and Threshold Setup

| | | |
|---|---|---|
| 3 -> 4 | 0.1 sec | min time period in 4; |
| | 058 PCI | Large ankle load to see foot on ground; |
| | 0.25 sec | Short time period in 3, |
| | 0.58 PCI | Motor NOT ready (ankle returned, temperature measured); Large ankle load to see foot on ground; |
| | −180 Nm/s | Min Ks Torque found |
| | −0.5 Nm/6 ms | at beginning of 3 Ks |
| | −1 Nm/10 ms | torque reduced in |
| | −1.0 Nm | fast speed Ks torque drops in 6 ms period Ks torque keeps dropping in 10 ms Ks torque drops from its min position |
| | −50 Nnm/s | Min Ks Torque found |
| | −2.0 Nm | at beginning of 3 HS torque NOT rising; Ks torque reduced in moderate speed; Ks torque drops big from its min position |
| | 25 Nm to 45 Nm | Protect 3 count |
| | 11 Nm/40 ms | drift on ankle encoder; varying based on user weight; Protect slow loading case; |
| | 1.5 sec | Long enough in 3; |
| | 30 Nm | Ankle loaded (>2 |
| | 0.3 sec | encoder counts); Ankle Loaded long to see foot on ground; |
| In STATE 4 | | On Entry {Check_battery_power; Read_motor_temperature;} Setup_decay_impedance_control; Update_Ks_torque_changes; Update_maximum_Ks_torque; Shut_down_check; |
| 4 -> 5 | 0.58 PCI | Large Hard stop load |
| | 25 to 45 Nm | Ankle loaded; |
| | 11 Nm/40 ms | Ankle loaded fast; |
| | 15 Nm | Hard stop NOT loaded; |
| | −5 Nm | Ks torque drops big to |
| | 0.10 Nm/s | confirm foot strike; Positive Ks torque rates to confirm foot flat happened; |
| 4-> 4 | 0.5 sec | Max time in 4 normally; |
| | −0.5 Nm/10 ms | To see Ks torque changing |
| | −5 Nm | direction; Ks torque drops big to confirm foot strike; |
| 4 -> 2 | | This state 4 was transitioned from state 6 |
| | 0.8 sec | Must stay in 4 long enough |
| | 30 Nm | Low Hard stop torque; |
| | −5 Nm/40 ms | Hard stop torque drops to see unloading; |
| | −180 Nm/s | Ks torque reduced in fast speed to see unloading |
| | 30 Nm | Low Hard stop torque; |
| | −11 Nm/40 ms | Hard stop torque drops to see unloading; |
| | −50 Nm/s | Ks torque reduced in moderate speed to see unloading |
| | 30 Nm | Low Hard stop torque; |
| | −11 Nm/40 ms | Hard stop torque drops to see unloading; |

TABLE 3-continued

State transition setup for an embodiment of an artificial leg device.
State Machine Transitions and Threshold Setup

| | | |
|---|---|---|
| | −1 Nm/10 ms | Ks torque keeps dropping in |
| | 0 Nm | 10 ms |
| | | Ks torque is low |
| | 50 Nm | moderate Hard stop torque; |
| | −22 Nm/40 ms | Hard stop torque drops very fast |
| | −50 Nm/s | to see unloading; Ks torque reduced in moderate speed to see unloading |
| In STATE 5 | | Update_extreme_Torque_rate; Update_Ks_torque_changes; Setup_decay_impedance_control; Shut_down_check; On Exit { Blend_torque_rate; Blend_reflex_Coeff; Blend_tail_spring;} |
| 5 -> 6 | 5 Nm | Hard stop triggered |
| 5 -> 4 | 0.5 sec | Max time in 5 normally; |
| | −0.5 Nm/10 ms | To see Ks torque changing direction; |
| | −5 Nm | To see foot strike for sure; |
| In STATE 6 | | Detect_peak_ankle_moment; Detect_significant_reflex_action; Update_motor_command_torque (torque,tailSpring,temperatureFactor, ForceField); Shut_down_check; |
| 6 -> 2 | 0.2 sec | Min Time in state 6 normally; |
| | 20 Nm | |
| | 0 Nm | Hard stop NOT engaged; |
| | −200 Nm/s | Hard stop still touching; Ks Not released; |
| | 1.6 sec | Max time allowed in state 6 |
| | 25 Nm | low ankle torque |
| | 10 Nm | Acknowledged; |
| | 0.02 sec | Ankle load released; Stayed long enough at low ankle torque level; |
| 6 -> 4 | 10 Nm | No reflex detected; |
| | 1 Nm | Hard stop NOT triggered; |
| | −1.2 Nm/10 ms | Last two conditions to see |
| | −150 Nm/s | foot strike for sure; |

Embodiments of the present disclosure may include a multi-modal control system for an artificial leg device having series and parallelelastic actuator-based muscle-tendon units (MTU) at the ankle and knee for modulation of joint impedance, joint equilibrium and reflex torque, in accordance with locomotion modality, gait cycle phase within that modality and cadence; a plurality of metasensors for intra-gait cycle determination of terrain modality, ground reaction force and zero-moment point, and external load-bearing influence; an intent recognition processor that employs the metasensor data to infer locomotion modality and the transitions between these; and a biophysically-inspired state control processor that employs MTU torque and derivatives, metasensor state and intent recognition output to accomplish transitions between the joint-based state machines.

The bionic architecture may restore function per normative measures of metabolic cost-of-transport and gait mechanics, including joint kinematics and kinetic measures. The architecture may further optimize battery economy and achieve safe operation in the event of power loss through use of tuned series-elastic elements and regenerative dynamic clutching (braking) functions in the joint MTU controls. The multi-modal architecture herein can be broadly applied to lower extremity augmentation systems—including powered prosthetic and orthotic leg systems, exoskeletons, and exo-muscle-tendon units—and humanoid robots that actuate the ankle, knee and hip.

Figure 12:
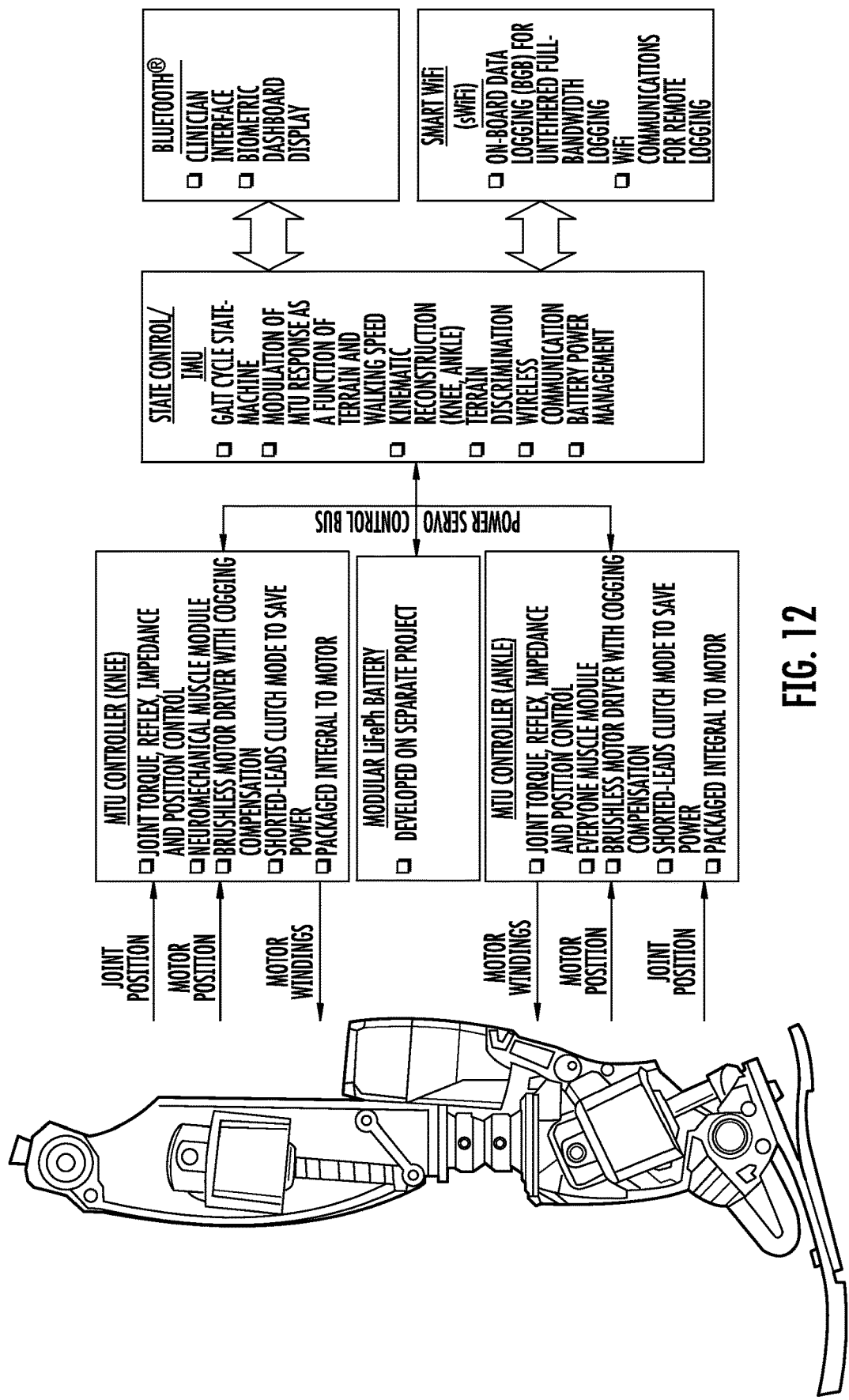
FIG. 12 illustrates an artificial leg device system architecture in accordance with some embodiments.

FIG. 12 illustrates elements of another embodiment of a bionic leg system architecture in accordance with the present disclosure. In the embodiment shown, the system includes series-elastic actuators (SEA) serving as bionic muscle-tendon units (MTU) at the ankle and knee; an ankle socket-mounted force/torque sensor to measure axial force, sagittal plane moment and coronal plane moment; a state control processor that embodies a gait cycle state machine, modulates MTU response, and recognizes wearer intent including terrain (sloping ground and stairs) context. Here, intent recognition can be accomplished through use of metasensors as follows:

Kinematic State Estimator (KSR)—The KSR employs a 6-DOF IMU embedded in the ankle or knee and the knee joint angle, $\theta_k$, to reconstruct the tibia and femur coordinate systems in real-time—capturing the inertial path of the ankle, knee and hip and points between these throughout all or part of a gait cycle.

Terrain Modality Discriminator (TMD)—The TMD applies pattern recognition of the ankle, knee and hip translational and rotational paths during the swing phase to infer underlying terrain. The state control processor uses the terrain context to inform the ankle and knee equilibrium and impedance at foot strike.

Ground Reaction Force/ZMP Estimator (GRFZMP)—The GRFZMP processes the force-torque sensor data, the ankle joint torque and the tibia kinematic state to compute the ground reaction force vector and the zero-moment position of this. This information may be used by the state control processor in combination with the KSR, TMD and EIE (below) to determine locomotion context (walking, sitting, standing, stair climbing) and/or to apply balance control while standing, walking and running.

External Influence Estimator (EIE)—The EIE may use the GRFZMP and the KSR information to determine, via inverse dynamic approximation, the external influences that must be acting on the trunk (as measured at the hip) to achieve its kinematic state (of acceleration). The EIE can estimate, for instance, the presence, and influence of external force as might be applied by the arms as the bionic leg wearer lifts out of a chair. The EIE can also estimate the presence and influence of trailing leg powered plantar flexion on a stair. Such information may be used by the state control processor to determine when to apply leg joint torques in such locomotion contexts. Additional details regarding various embodiments of the leg architecture are provided in the references incorporated by reference above.

Control Architecture

Embodiments of the leg system employ a loosely-coupled joint control architecture. Here, the ankle state machine and control behaviors are largely independent of the knee control state. Ankle state machine and control behaviors are described in greater detail in the references incorporated by reference above. In particular, the biophysically-motivated ankle state machine and behaviors are described in detail in U.S. Provisional Patent Application Ser. No. 61/662,104, entitled "Bionic Control System for an Artificial Ankle Joint."

Figure 13:
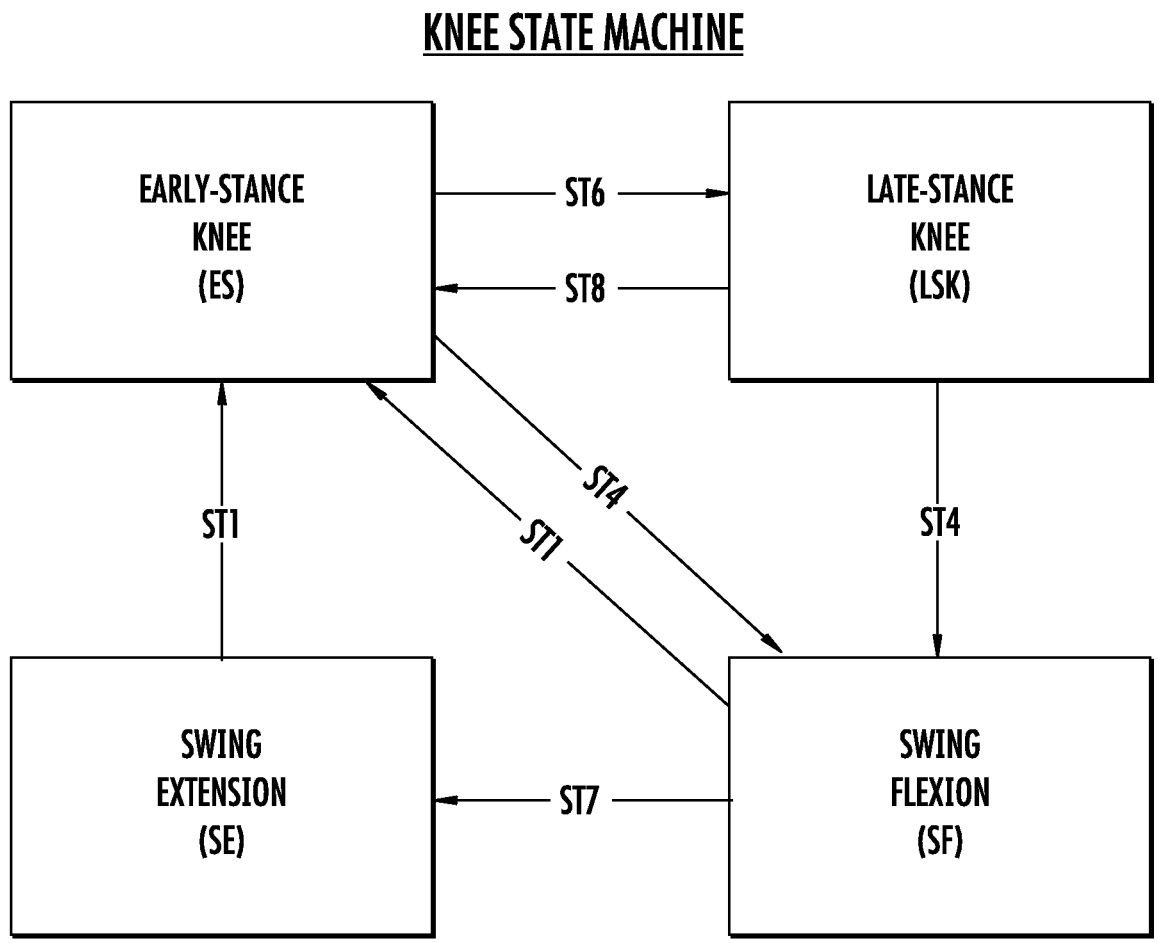
FIG. 13 shows a schematic of a knee state machine with state transitions in accordance with some embodiments.

A schematic of one embodiment of a knee state machine is illustrated in FIG. 13. As shown in FIG. 13, the Knee State Machine (KSM) embodies four states—Early Stance, Late Stance, Swing Flexion and Swing Extension with state-dependent control behaviors and state transitions (ST1, ST4, ST6, ST7 and ST8), as further discussed below.

State-Dependent Control Behaviors

Figure 14:
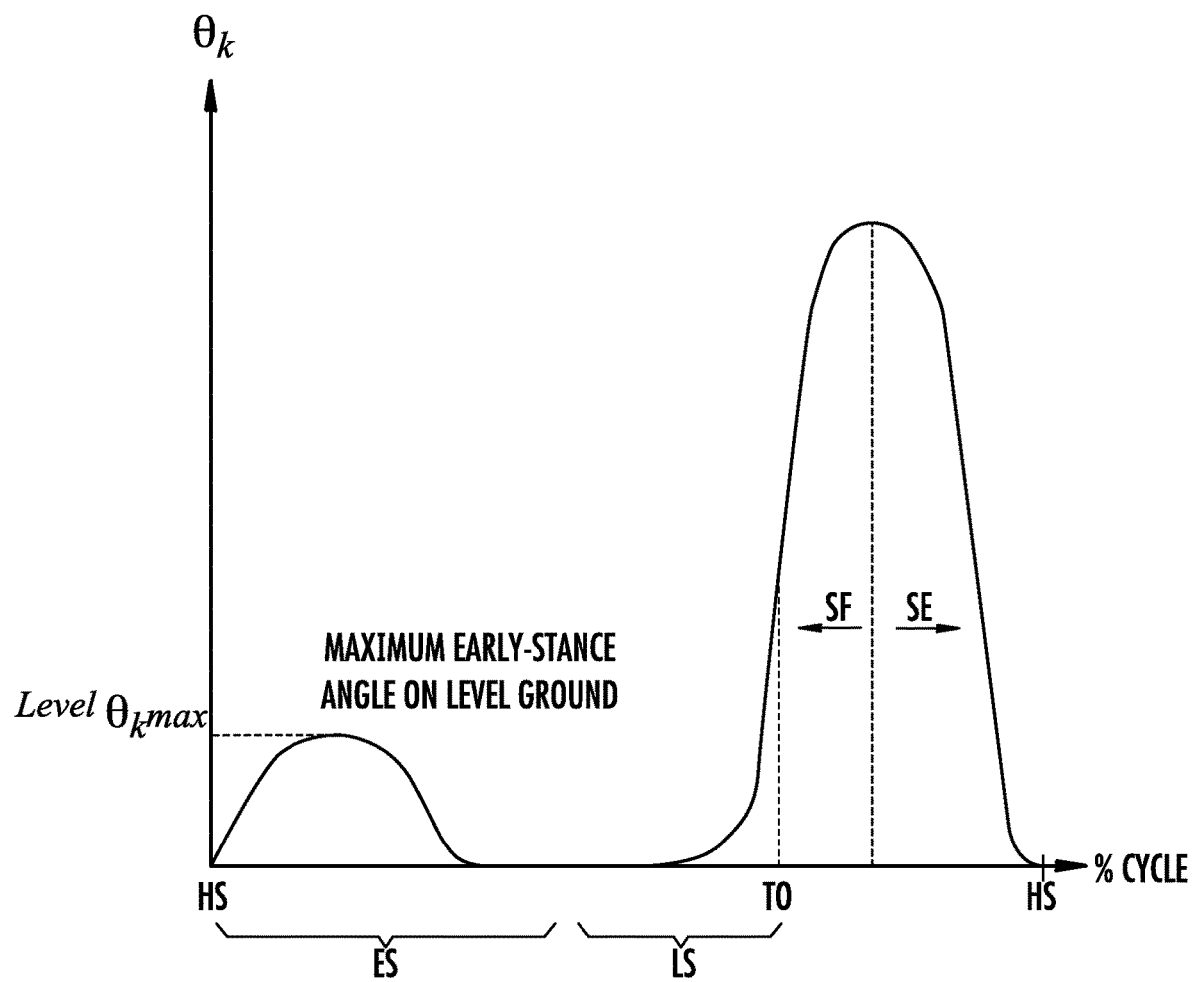
FIG. 14 depicts a graph of knee kinematics for a typical gait cycle.

FIG. 14 illustrates the kinematic behavior of the knee during a typical gait cycle where ES refers to Early Stance; LS refers to Late Stance; ESW refers to Early Swing; LSW refers to Late Swing; $\theta_k$ refers to Knee Angle; HS refers to Foot Strike; and TO refers to Toe-Off.

Early Stance

In Early Stance, the knee applies a lightly-damped spring response defined by stiffness, $k_{ES}$, and damping, $b_{ESO}$. For stance flexion, $\delta\theta_k = \theta_k - \theta_{0es}$, when less than about 15°, the early stance impedance relation may be provided as follows:

$$\Gamma_k = -k_{ES}(\theta - \theta_{es0}) - b_{es0}\dot{\theta} \quad \text{Eq (7)}$$

Where $\Gamma_k$–knee joint torque $\theta_{es_0}$ fully extended knee angle setpoint, typically 0 deg For stance flexion that exceeds about 15°, the joint impedance relation creates a highly damped response:

$$\Gamma_k = -b_{es_{large}}\dot{\theta}_k \quad \text{Eq (8)}$$

Equations 7 and 8 may be implemented by using closed-loop torque control, using SEA deflection as a measure of joint torque feedback. In another embodiment, the knee SEA may employ a series elasticity with stiffness substantially equal to $k_{es}$ In this way, the motor drive transmission can be locked at $0_{es0}$, enabling the series elastic element to compress and extend without motor movement to account for the maximum early stance knee flexion for typical level-ground gait cycles.

In another embodiment, the motor may be employed as a programmable clutch (dynamic brake/damper) by shorting the motor leads applying a strong braking function with a time constant typically in the range of approximately 800-1500 milliseconds. Details concerning the use of shorted leads may be found in U.S. patent application Ser. No. 13/417,949, entitled "Biomimetic Joint Actuators." In such an embodiment, the battery power source may be disconnected from the SEA, thereby eliminating battery consumption during knee flexion and extension in level-ground walking.

Figure 15:
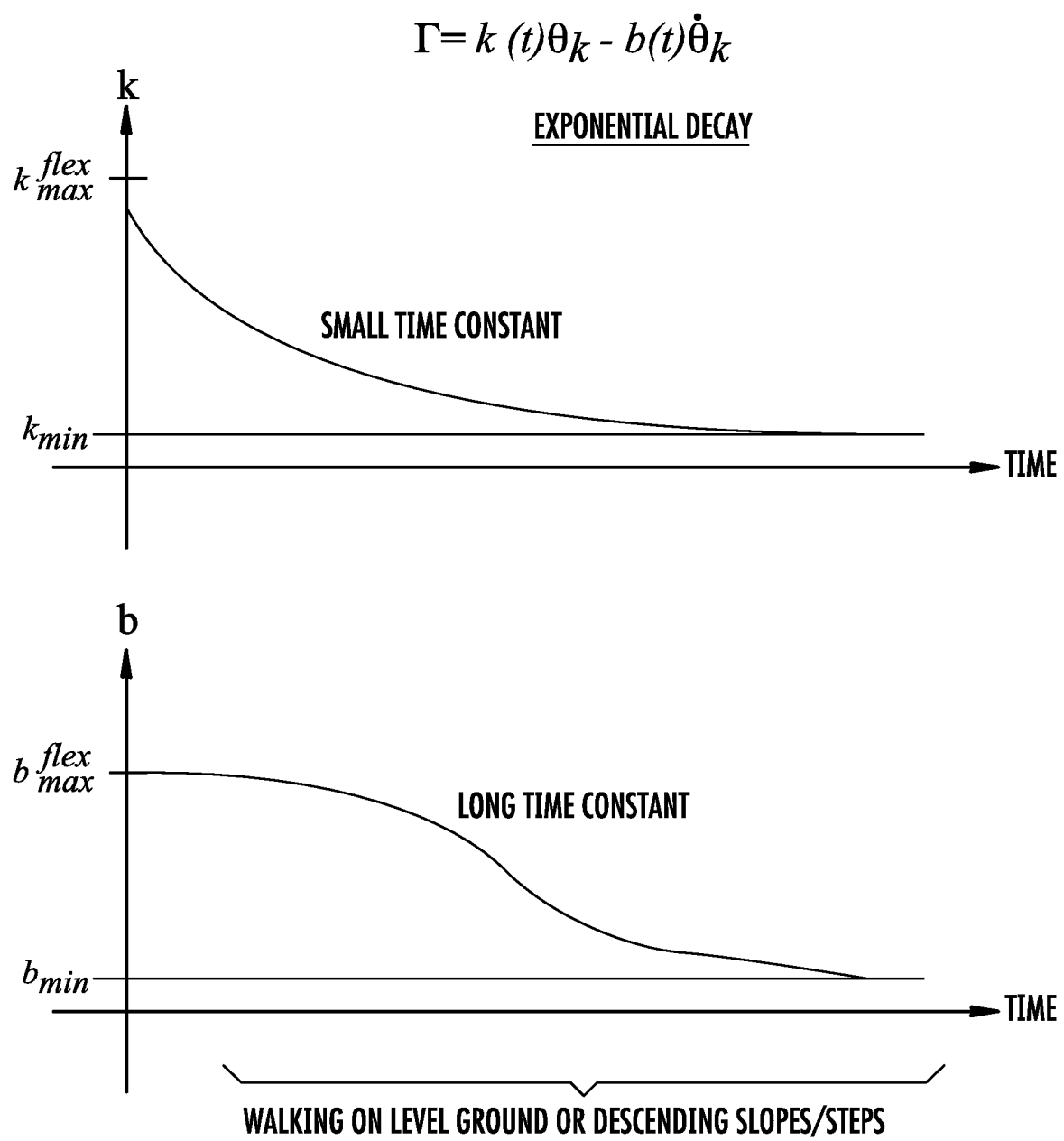
FIG. 15 shows graphs of early stance exponential stiffness and damping responses in accordance with some embodiments.

In some cases, the shorted-leads may be pulse-width modulated, enabling the damping to be controlled, e.g., to reduce the damping at large flexion while at the same time harvesting energy to charge the bionic leg power source (i.e., battery) during, for example, the swing phase of walking. Since the knee joint generally draws net energy, such an embodiment can be used to operate the knee joint at extremely low power in at least early stance flexion/extension early swing and late swing, even when the battery is disconnected. The shorted leads functionality can make possible assertion of a safe state during fault or power interruption, thereby protecting the wearer. In some embodiments, $k_{es}$, and $b_{es}$, are functions of time (e.g., may exhibit a time-dependent decay behavior). For instance, the change from a stiffness-dominated response to the damping-dominated response may not be accomplished by crossing an angle threshold, but rather by applying a programmable, exponential decay of the stiffness and damping as shown in FIG. 15, which illustrates an early stance exponential stiffness and damping response for an embodiment of a knee device.

The stiffness and damping impedance coefficients may be defined by the following relations:

$$=\tau_k^2 \ddot{k}_{es}(t) + 2\tau_k \dot{k}_{es}(t) + 1 = k_{es_{min}} \quad \text{Eq (9)}$$

Where $k_{es}(0) = k_{es_{max}}$ and $\tau_k$ is the time constant of the stiffness decay $$\tau_b^2 \ddot{b}_{es}(t) + 2\tau_b \dot{b}_{es}(t) + 1 = b_{es_{min}} \quad \text{Eq (10)}$$

Where $b_{es}(0) = b_{es_{max}}$ and $\tau_b$ is the time constant of the damping decay As shown in FIG. 15, the time constant for stiffness decay may be set to be shorter than the damping time constant. Though, in some embodiments, the time constant for stiffness decay may be greater than the damping time constant.

In some embodiments, a first-order or higher order differential equation may be used in place of Eqs. 9 and 10. A second-order response may be advantageous in that the attenuation is substantively delayed—the initial values are substantially maintained for a certain amount of time controlled by the time constant prior to dropping off. Through these time varying impedances, the knee will behave during early stance as an efficient spring during level ground walking, a damper with a relatively high damping value for stair and slope descent, and a lightly damped knee while sitting.

Late Stance

The joint torque sign reversal at substantially full knee extension signals the transition from Early Stance to Late Stance in a typical gait cycle. In one embodiment, the Late Stance reflex behavior follows the relation below:

$$\tau_{motor_{knee}} = p_{\!f\!f}(\Gamma_k)\left(\frac{\Gamma_k}{\Gamma_{0_k}}\right)^{N(\Gamma_k)} \quad \text{Eq (11)}$$

Where $\tau_{motor_{knee}}$ is the SEA motor torque, $\Gamma_{0_k}$ is a normalizing torque defined by body weight and activity level, and pff( ) and N( ) sre functions of knee torque rate of change at entry to late stance.

In other embodiments, a neuromuscular model, also employing positive force feedback on a modeled Gastrocnemius muscle, may be used. For further details regarding this neuromuscular model, the disclosure of U.S. Provisional Patent Application Ser. No. 61/595,453, entitled "Powered Ankle Device" may be relevant.

Figure 16A:
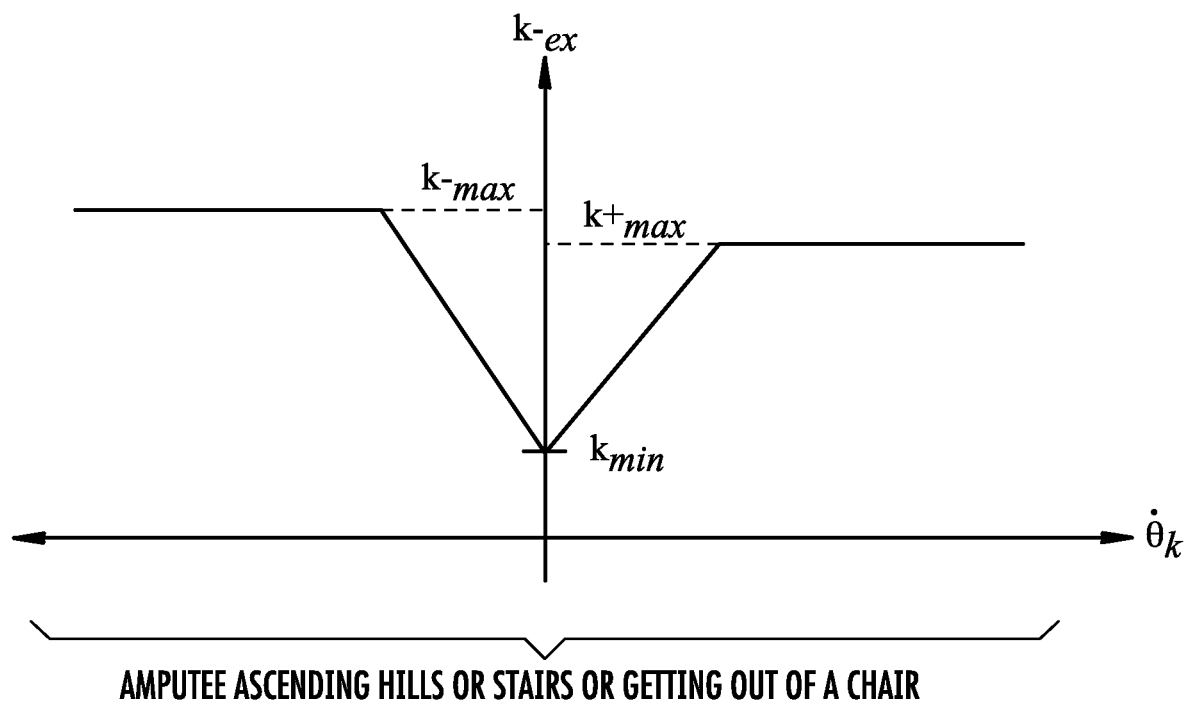
FIG. 16a illustrates a graph of rate-dependent early stance spring stiffness in accordance with some embodiments.
Figure 16B:
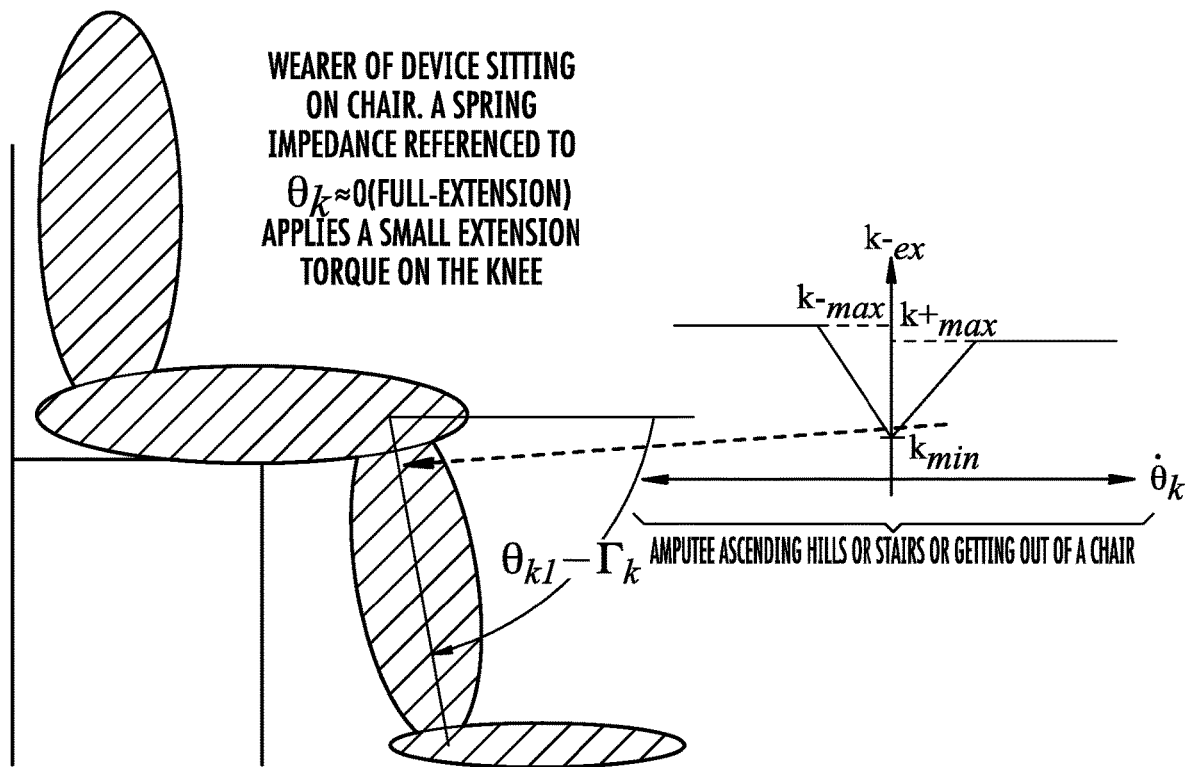
FIG. 16b shows a schematic of a wearer in a sitting position in accordance with some embodiments.
Figure 16C:
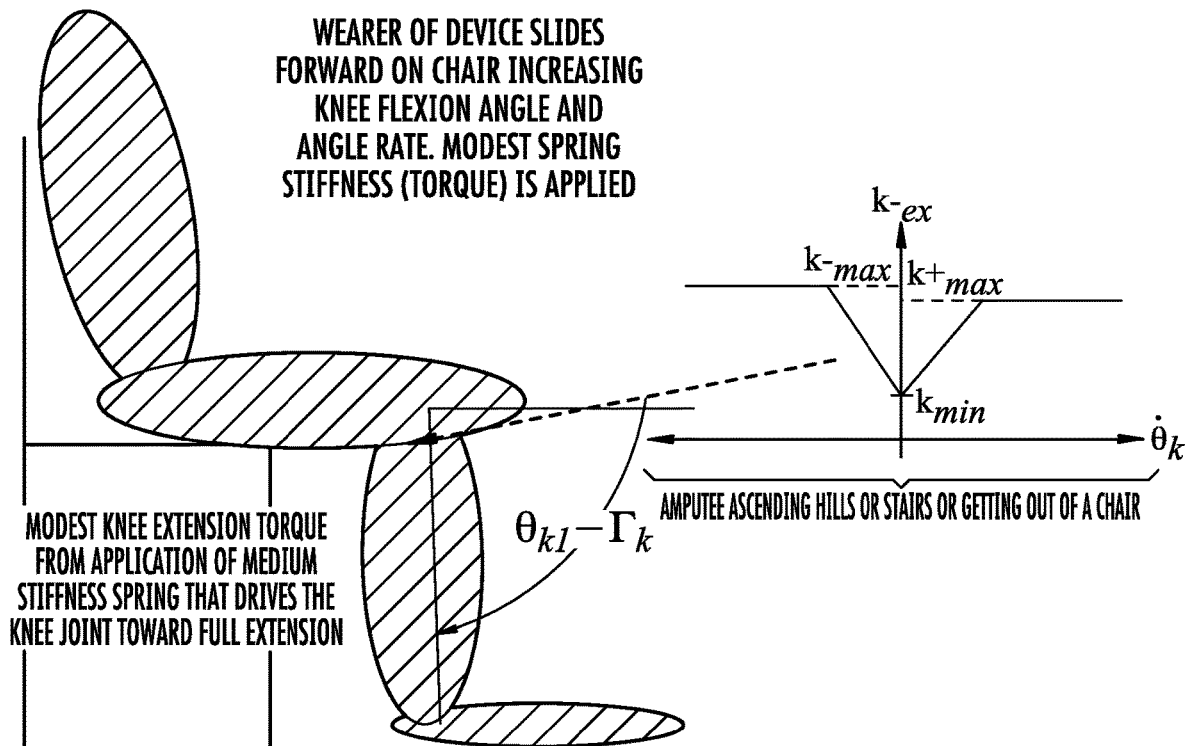
FIG. 16c shows a schematic of the wearer of FIG. 16b in a sitting position in accordance with some embodiments.
Figure 16D:
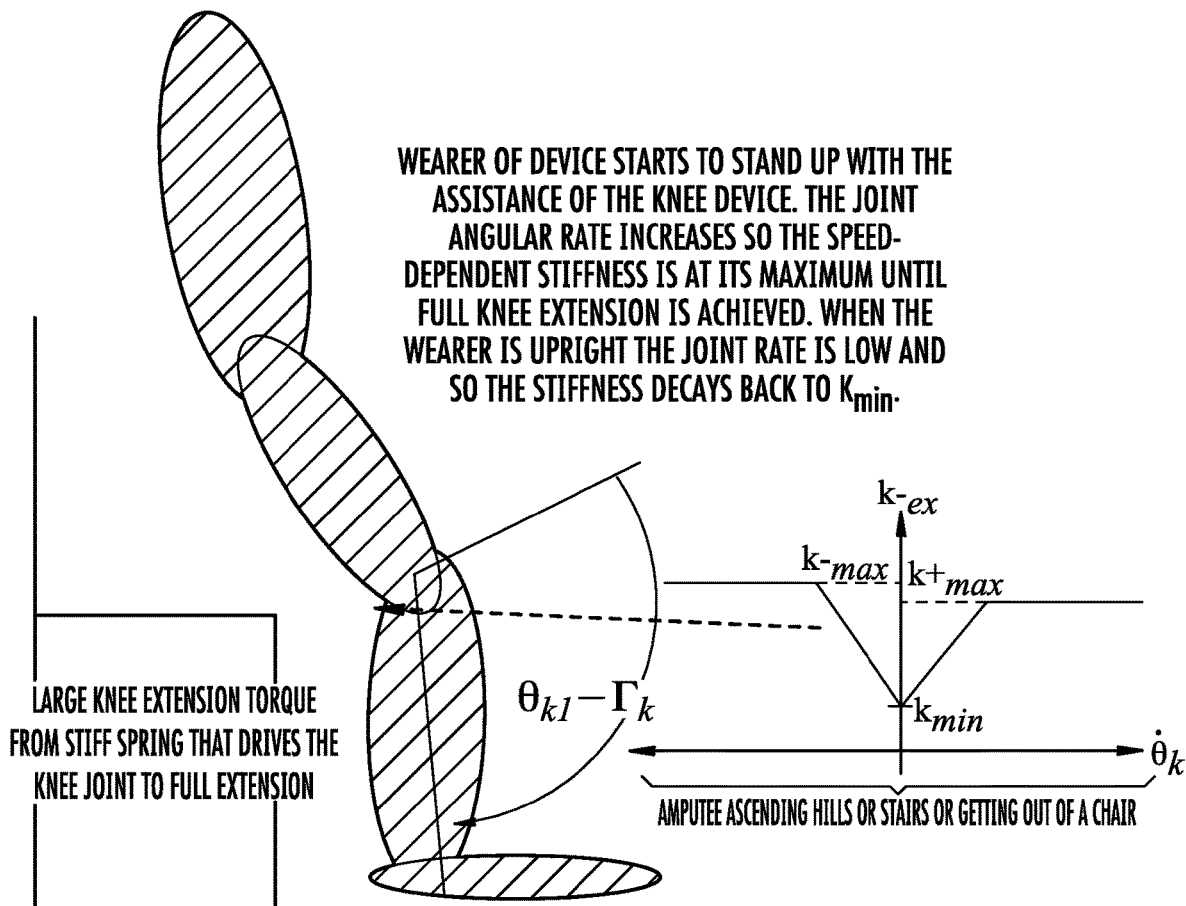
FIG. 16d shows a schematic of the wearer of FIGS. 16b-16c in an upright position in accordance with some embodiments.

In certain cases—including stair ascent, steep ramp ascent and during the transition from sitting to standing—the knee joint may be flexed past a threshold of $\theta_{k_{iso}}$, and extending at a substantial rate ($|\dot{\theta}_k|>\dot{\xi}_{ext_0}$) where $\dot{\xi}_{ext_0}$ is the rate threshold. In this case, a rate dependent spring stiffness, $k_{ex}$, that applies positive feedback in response to angular rate increases for an embodiment of a knee device as shown in FIG. 16a and captured in the anti-slip impedance control behavior defined by Eq. 12 may be applied.

$$\Gamma_k = -k_{ex}(\tilde{\dot{\theta}}_k)\tilde{\theta}_k - b_{ex}(\dot{\theta})\dot{\theta}_k \quad \text{Eq (12)}$$

Where $b_{ex}(\dot{\theta})$ applies light damping to achieve stability when $\dot{\theta} \leq 0$, $b_{ex}(\dot{\theta})$ applestrong damping to resist flexing $\dot{\theta}_k$ is the knee joint angular rate, and $\tilde{\dot{\theta}}$ is the output of a peak detection filter of the form $\tau_{ext}(\dot{\theta})\tilde{\dot{\theta}}+\tilde{\dot{\theta}}=\dot{\theta}$, where $\tau_{ext}(\dot{\theta})=\tau_{ext_{small}}$ if $\dot{\theta}<0$ and $\tau_{ext}(\dot{\theta})=\tau_{ext_{large}}$ if $\dot{\theta}\geq 0$ And where $k_{ex}((\tilde{\dot{\theta}})$ is of the form shown in FIG. 16a In some embodiments, $k_{ex}$ and $b_{ex}$ are time-dependent functions that exponentially decay over time and are initialized to the nominal form when retriggered ($\dot{\theta} \leq \dot{\xi}_{ext_0}$) In an "anti-slip" embodiment described here, momentary flexion velocities do not cause the knee torque to drop—thereby making it easier for the wearer to maneuver (e.g., to get out of a chair or to transition to bionic limb support when the sound side (trailing leg) is pushing off of a stair below the bionic limb). FIG. 16s defines the general form of $k_{es}$, illustrating that the flexion stiffness may increase with increasing joint speed. In some cases, the peak flexion stiffness may have a lower peak than in extension, enabling the wearer to more easily flex the knee while sitting. FIGS. 16b-16d illustrate schematics of a wearer moving from a sitting position to a standing upright position.

Swing Flexion

The Early Swing state transition occurs at toe-off, as reported by the ankle state machine. In early swing flexion, knee behavior may be ballistic for flexion angles less than about 45° (e.g., no spring or damping) and lightly damped ($b=b_{sf}$) for greater flexion. This behavior is captured in Eq. 13.

$$\Gamma_k = -b_{sf}\dot{\theta}_k \ V \ \theta_k < \theta_{sf} = 0 \text{ elsewhere} \quad \text{Eq. (13)}$$

Swing Extension

Figure 17A:
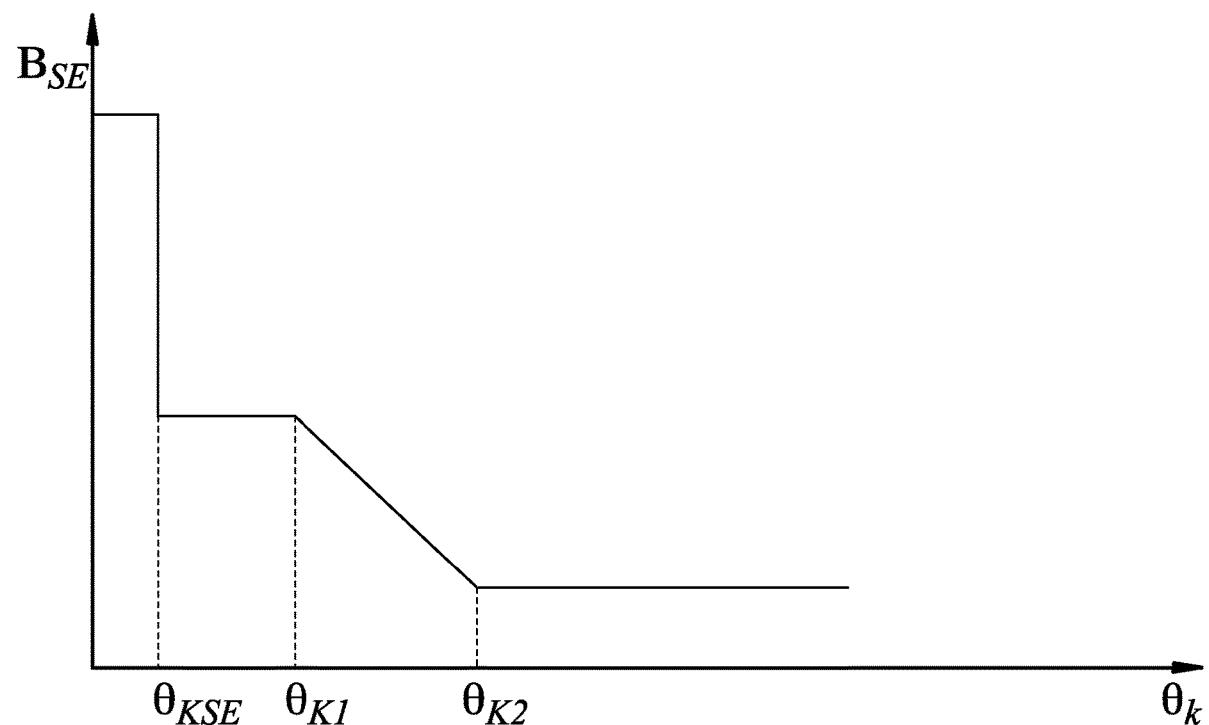
FIG. 17a shows a graph of a piece-wise constant and linear damping constant as a function of knee flexion in accordance with some embodiments.
Figure 17B:
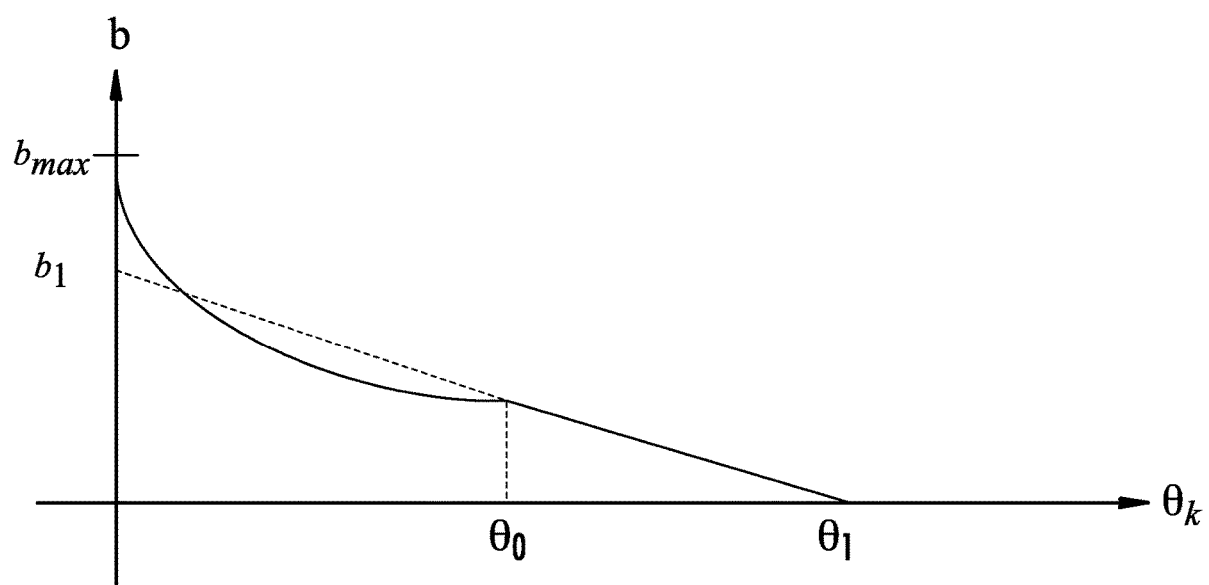
FIG. 17b shows a graph of a piece-wise linear and quadratic damping constant as a function of knee flexion in accordance with some embodiments.
Figure 17C:
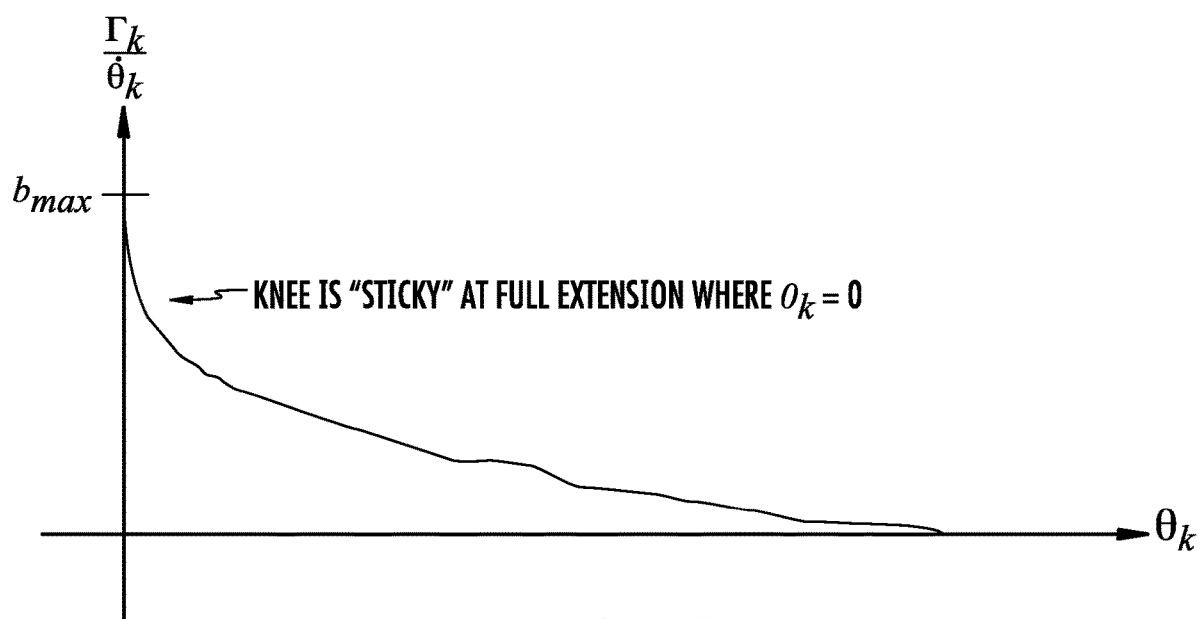
FIG. 17c shows a graph of an angular rate as a function of extension angle in accordance with some embodiments.

Once the maximum swing flexion is achieved, the knee state transitions to swing extension. In early swing extension the behavior is nearly ballistic (e.g., lightly damped) with damping constant, $b_{se}=b_{se_\infty}$. The damping coefficient increases nearly quadratically as the knee flexion approaches $\theta_k=\theta_{kes_0}$, as shown in three piecewise continuous angle-dependent damping function embodiments (in swing extension) in FIGS. 17a-c. FIG. 17a depicts the behavior of an embodiment that exhibits piece-wise constant and linear behavior. FIG. 17b illustrates the behavior of an embodiment that exhibits piece-wise linear and quadratic behavior. FIG. 17c shows the behavior of another embodiment that exhibits a more general functional form.

In Swing Extension, such behavior may be captured in Eq. 14.

$$\Gamma_k = -b_{se}(\theta_k)\dot{\theta}_k \quad \text{Eq. (14)}$$

Where $b_{se}(\theta_k)$ is defined as a piecewise continuous functions per FIGS. 17a-c Damping during Swing Extension may be used to decelerate knee flexion (tibia angular rate) as the joint angle approaches full-extension—increasing substantially linearly until $\dot{\theta}$ drops below a threshold angle. Below the threshold, the damping increases according to a substantially quadratic function as it approaches $\theta \approx 0$. Such damping creates a "sticky" behavior that holds the joint near full-extension-preparing the knee to absorb the foot strike energy and to transition to the spring-like behavior in Early Stance.

State Transitions

FIG. 13 illustrates the knee state machine and defines knee controller state transitions, as further discussed below.

State Transition 1 (ST1): Swing Extension (or Flexion)-to-Early Stance

Figure 18:
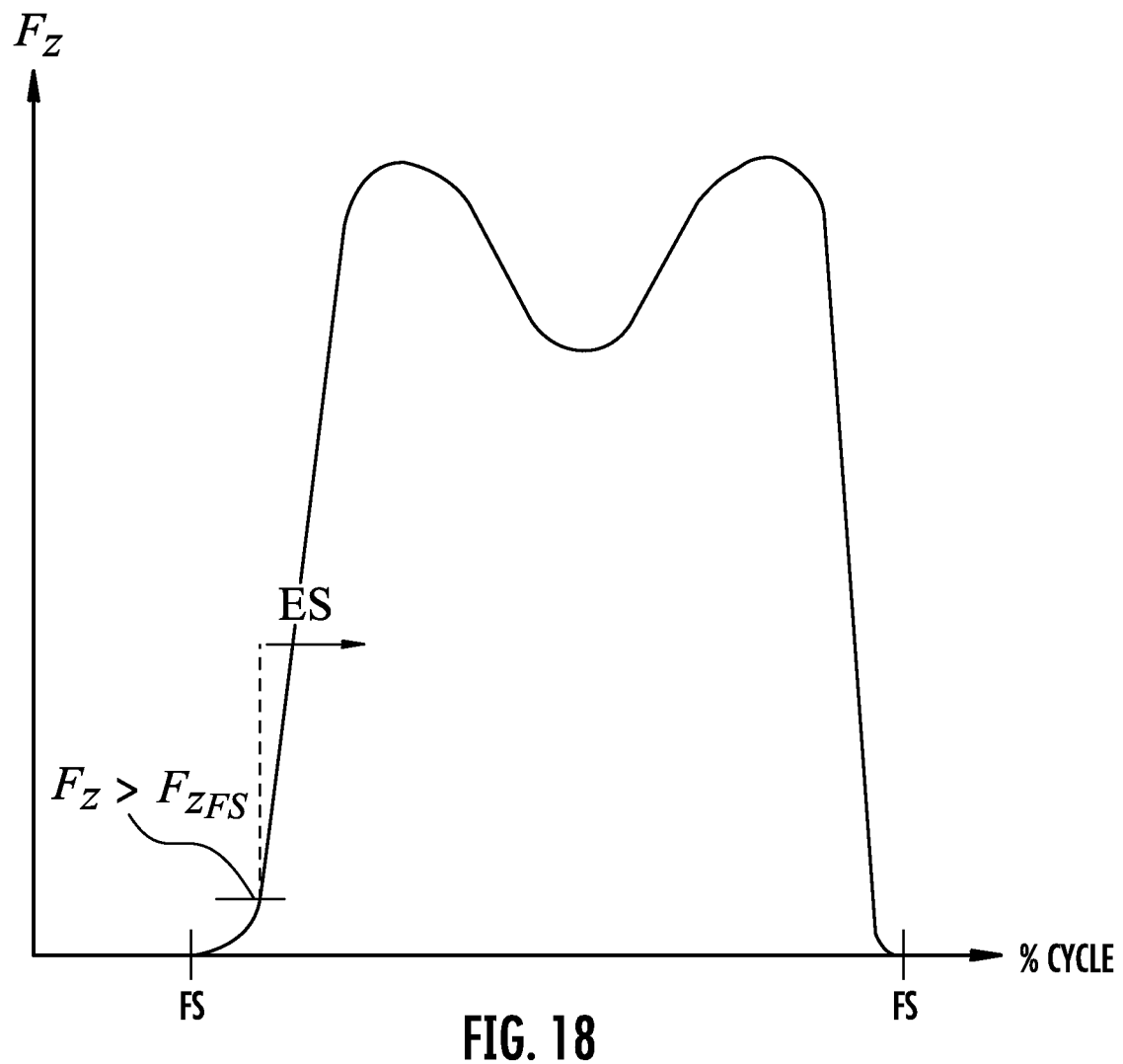
FIG. 18 depicts a graph of a ground reaction force used to detect a foot strike transition in accordance with some embodiments.

The foot strike gait event marks the transition from Swing Extension (or Flexion)-to-Early Stance—a transition that aligns with the Late Swing to Early Stance transition on the ankle. Here, the world-z component of the ground reaction force, as shown in FIG. 18, will be used to detect the ST1 transition (i.e., foot strike transition, heel-strike or toe-down), defined as:

$$ST1 = (F_c > F_{z_{FS}}) \quad \text{Eq. (15)}$$

Where $F_{z_{FS}}$ is the force transition threshold signals fool—strike.

In another embodiment as described in U.S. Provisional Patent Application Ser. No. 61/662,104, entitled "Bionic Control System for an Artificial Joint," a logic transition informed by ankle torque and derivatives can be used to accomplish ST1.

State Transition 6 (ST6): Early Stance-to-Late Stance

The Early Stance to Late Stance transition gait event signifies that toe-loading is occurring when the knee is fully extended as defined by the logic equation:

$$ST6 = \overbrace{(\xi^- < \theta_k < \xi^-)}^{\text{Knee angle is small}} \wedge \underbrace{(\Gamma_a < \Gamma_{toe\_load})}_{\text{Toe is loaded}} \quad \text{Eq. (16)}$$

Where

ξ⁺ and ξ⁻ are small angles signifying proximity to full extension, and $\Gamma_{toe\ load}$ is the toe loading threshold as measured at the ankle, and $\Gamma_a$ signifies the ankle torque reported by the ankle MTU.

In other embodiments, toe loading is detected by determining whether the ZMP of a ground reaction force of significant magnitude is substantially located in the forward half of the foot.

State Transition 4 (ST4): Late Stance (or Early Stance)-to-Swing Flexion

The toe-off gait event signals the transition to Swing Flexion from either Late Stance or Early Stance. ST4 is defined as:

$$ST4 = (F_z < F_{z_{toe\ off}}) \qquad \text{Eq. (17)}$$

Where $F_z$ is the z-component. of the ground reaction force, $F_{z_{toe\ off}}$ is the toe-off force threshold.

In other embodiments, substantially zero torque, as reported by the ankle MTU, can be used to detect the toe-off condition. In another embodiment described in U.S. Provisional Patent Application Ser. No. 61/662,104, entitled "Bionic Control System for an Artificial Joint," ankle torque and derivatives ($\Gamma_{ankle} \approx 0$) can be used as input for triggering or modulating parameters of the ST4 transition.

State Transition 7 (ST7): Swing Flexion-to-Swing Extension

The state transition from Swing-Flexion to Swing Extension is marked by a sign reversal in the knee angular velocity—detected here as the time when the knee velocity goes to zero at a time sufficiently after toe-off:

$$ST7 = \underbrace{(t_{sf} > t_{min_{sf}})}_{\text{Sufficient time elapsed}} \wedge \underbrace{(\xi^- < \dot{\theta}_k < \xi^+)}_{\text{Knee velocity near zero}} \qquad \text{Eq. (18)}$$

Where $t_{sf}$ is the time elapsed since toe-off, $t_{sf_{min}}$ is the minimum duration threshold, and ξ⁺ and ξ⁻ define the small velocity boundary.

State Transition 8 (ST8): Late Stance-to-Early Stance

In some circumstances, e.g. when the wearer is standing quietly and then enters Late Stance and then flexes the knee, it may be appropriate for the state machine to transition back to early stance. The logic is defined as follows:

$$ST8 = \underbrace{(\theta_k > \theta_{k_{large}})}_{\text{Knee angle is large}} \wedge \underbrace{(\xi_\Gamma^- < \Gamma_k < \xi_\Gamma^+)}_{\text{Ankle torque is small}} \qquad \text{Eq. (19)}$$

Where $\theta_{k_{large}}$ defines the angle threshold, and $\xi\Gamma^-$ and $\xi\Gamma^+$ define the small torque detection boundaries.

Other Embodiments

Self-Adjusting Joint Equilibrium

In this embodiment, the joint equilibrium tracks the joint angle with a programmable convergence—preferably through use of a first or second-order tracking filter with time constant, τ. In some embodiments, the system is configured for the joint equilibrium to exhibit time-dependent behavior that relaxes to an equilibrium that is substantially equivalent to the current joint angle. That is, in accordance with the system exhibiting a programmable convergence, the joint equilibrium of the system continually, yet gradually, tracks the current joint angle. For example, if the joint angle does not change after a long period of time, then the joint equilibrium gradually relaxes from an initial value to a value equal to that of the current joint angle.

In some embodiments, self-adjusting joint equilibrium behavior may be governed by the following relationships:

$$\Gamma = -k(\theta - \theta_0) - b\dot{\theta} \qquad \text{Eq. 20}$$

$$\tau_0 \dot{\theta}_0 = \theta \qquad \text{Eq. 21}$$

Equation 21 is inserted into Eq. 20 and the resulting relationship is subject to a Fourier transform, where the function is transformed from the time domain to the frequency domain. Accordingly, the derivative represented by (·) is replaced with s=jω and $\omega_0$ with $$\frac{1}{\tau_\theta},$$

resulting in an impedance relation of the form:

$$\Gamma(s) = \left\{ \left( b + \frac{K}{\omega_\theta} \right) H(s) \right\} s\ \theta(s) \qquad \text{Eq. 22}$$

where H(s) is defined by the relation, $$H(s) = \left( \frac{\frac{s}{k} + 1}{\frac{s}{\omega_\theta} + 1} \cdot \frac{\frac{k}{b} + \omega_\theta}{1} \right) \qquad \text{Eq. 23}$$

Figure 19:
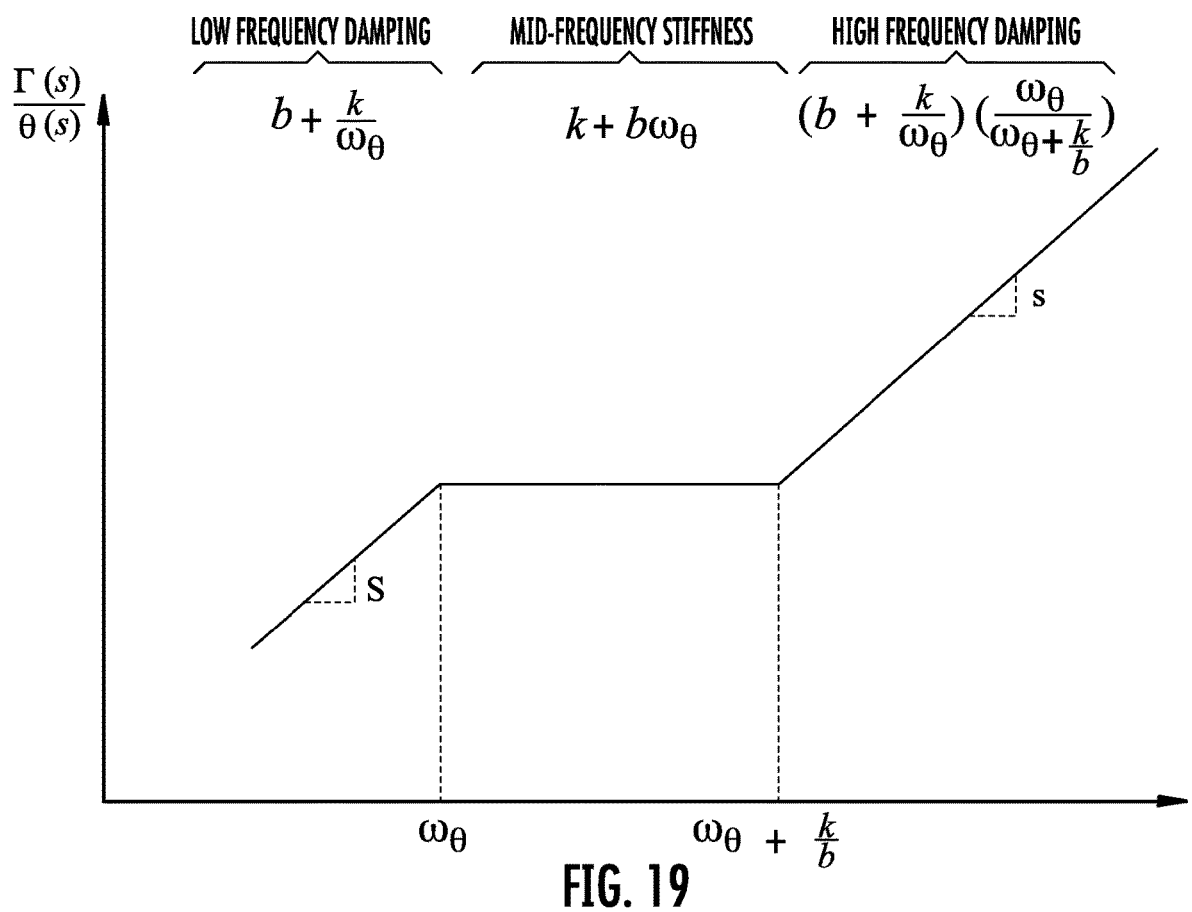
FIG. 19 illustrates the frequency response of a self-adjusting joint equilibrium impedance.

FIG. 19 illustrates the impedance transfer function, $$\frac{\Gamma(s)}{\theta(s)},$$

represented by Eq. 22.

The frequency response of this impedance law has interesting properties. At low frequencies, the impedance behaves as a damper with coefficient, b*=b+kτ. At medium frequencies, the impedance has stiffness properties with an equivalent stiffness of $$k^* = k + \frac{b}{\tau}.$$

And at high frequencies, the impedance behaves as a damper with equivalent damping of $$b^* = (b + k\tau) \left( \frac{\omega_\theta}{\omega_\theta + \frac{k}{b}} \right) \text{ where } \omega_\theta = \frac{1}{\tau}$$

is the transition frequency between the first damping and stiffness behaviors. Here, $\omega_0$ may rang from 0-13 rad/sec (0-2 Hz) providing a primarily damping response in that range. Between $\omega_{theta}$ and about 60 rad/sec (a preferred range between 5-20 Hz), a stiffness dominated response is applied. Above this latter frequency defined by $$\omega_\theta + \frac{k}{b},$$

a damping-dominated response is applied. Often wearers complain that it is hard to maintain balance when the leg joints are in a substantially lightly damped state. So by implementing this method, improved stability results because in the frequency range between 1-10 Hz a stiffness-dominated response is applied that serves to restore balance.

Blended Reflex

The following disclosure describes two blended reflex methods, each blending (interpolating) independently tuned responses—defined by torque gain ($P_{ff}$) and torque exponent (N), at a fast and a slow walk speed. At speeds below the "slow-walk" speed as determined by the wearer (e.g., less than 0.75 m/s), the reflex employs a slow-walk parameter set; at speeds greater than the fast-walk speed as determined by the wearer (e.g., greater than 1.75 m/s), the reflex employs the fast walk parameter set; and at speeds in between, the reflex adds the two responses together in accordance with a linear or non-linear interpolation based upon walking speed, a surrogate for walking speed (e.g., pitch rate in mid-stance), a kinetic (e.g., torque rate) or kinematic (e.g., joint angle rate). The term walking speed and operating speed below may loosely refer to the walking speed, surrogates of walking speed, a suitable kinetic rate or a suitable kinematic rate.

Other interpolations may be used, and more than two speed-registered responses may be blended through more complex interpolation, for example, based upon the "distance" between the operating speed and each of the tuned speeds. This approach may be advantageous over the existing methods in that both the gain and exponent can be independently controlled—that is, these reflex coefficients can be tuned independently of each other. For instance, a slow walk reflex response may require a lower exponent torque than that required by a fast walk reflex response, and vice-versa. With fixed N (the variable that controls timing), there is a tradeoff between slow-walk consistency and fast walk power and battery economy. By applying independent tuning, an optimum performance may be achieved at both ends of the walking speed spectrum, and overall wearer experience can be improved.

Method I blends two torque models—one defined at a slow speed and one at the fast speed, as determined by the wearer—with gain, $P_{ff}(\dot{s}_{slow})$, and exponent, $N(\dot{s}_{slow})$, for a first ("slow-walk") torque model; and gain, $P_{ff}(\dot{s}_{fast})$, and exponent, $N(\dot{s}_{fast})$, for a second ("fast-walk") torque model. Method II blends the gains and exponents into a single torque model—with gain, $\tilde{P}_{ff}(\dot{s})$ and exponent, $\tilde{N}(\dot{s})$, where the gain and exponent are speed interpolated (via linear or non-linear interpolation) across the speed domain, [$\dot{s}_{slow}$, $\dot{s}_{fast}$]. The blended torque models are expressed by suitable computations below.

Method I: Blended Torque Models $$\tau_{slow} = P_{ff_{slow}}\left(\frac{\Gamma_{ankle}}{\Gamma_0}\right)^{N_{slow}}$$

-continued $$\tau_{fast} = P_{ff_{fast}}\left(\frac{\Gamma_{ankle}}{\Gamma_0}\right)^{N_{fast}}$$

$$\tau_{motor} = c_1(\dot{s})\tau_{slow} + c_2(\dot{s})\tau_{fast}$$

$$c_2 = 1 - c_1$$

$$c_1(\dot{s}) = 1 \text{ for } \dot{s} \leq \dot{s}_{slow}$$

$$c_1(\dot{s}) = 0 \text{ for } \dot{s} \geq \dot{s}_{fast}$$

$$c_1(\dot{s}) = \frac{(\dot{s}_{fast} - \dot{s})}{(\dot{s}_{fast} - \dot{s}_{slow})} \text{ for } \dot{s}_{slow} < \dot{s} < \dot{s}_{fast}$$

Method II: Blended Coefficients $$\tau_{motor} = \tilde{P}_{ff}(\dot{s})\left(\frac{\Gamma_{ankle}}{\Gamma_0}\right)^{\tilde{N}(\dot{s})}$$

Where $$\tilde{P}_{ff}(\dot{s}) = c_1(\dot{s})P_{ff}(\dot{s}_{slow}) + c_2 P_{ff}(\dot{s}_{fast})$$

and $$\tilde{N}(\dot{s}) = c_1(\dot{s})N(\dot{s}_{slow}) + c_2 N(\dot{s}_{fast})$$

Where $c_1$ and $c_2$ are defined as in Method I.

Non-Linear Distance-Based (Quadratic Non-Linear Interpolation)

$$c_2 = 1 - c_1$$

$$c_1(\dot{s}) = 1 \text{ for } \dot{s} \leq \dot{s}_{slow}$$

$$c_1(\dot{s}) = 0 \text{ for } \dot{s} \geq \dot{s}_{fast}$$

$$c_1(\dot{s}) = \frac{(\dot{s}_{fast} - \dot{s})^2}{(\dot{s}_{fast} - \dot{s}_{slow})^2} \text{ for } \dot{s}_{slow} < \dot{s} < \dot{s}_{fast}$$

FIGS. 20-23 illustrate ankle data gathered from test subjects of walking information that are used as design parameters for the control of artificial leg devices in accordance with the present disclosure. Accordingly, embodiments provided herein may employ this data to create a dashboard of normative measures across walking speed that capture the kinetics and kinematics of natural limbs. In some embodiments of the control architecture described above, the kinetic and kinematic response of the bionic ankle joint is projected onto this dashboard of normative measures. The impedance, equilibrium and torque, including reflex, modulation may then be optimized to fit within the normative statistical range noted in the dashboard. Bionic restoration of ankle-foot function, as measured by the closeness of fit, is thereby achieved. And this projection of kinetic and kinematic measures onto the dashboard serves as a record that can be used by the clinician to prove the efficacy of the bionic limb as this might be needed for insurance reimbursement or other purposes.

Figure 20:
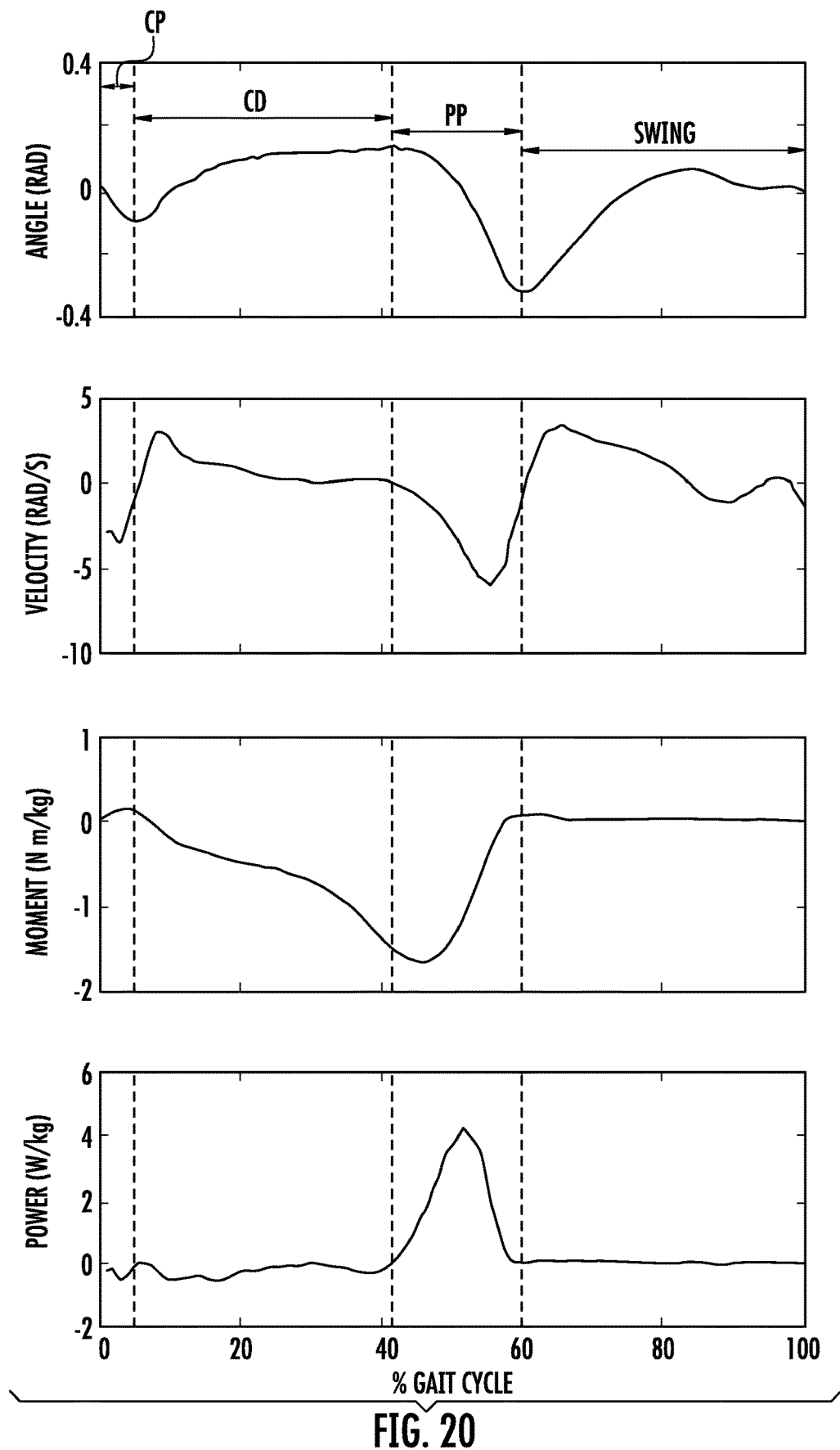
FIG. 20 shows normative ankle angle, angular velocity, moment, and power data plotted as a percentage of the gait cycle.

FIG. 20 shows graphs that depict ankle angle, angular velocity, moment, and power plotted as a percentage of the gait cycle. Plots are shown for the average of all subjects walking at their fast walking speed (e.g., between 1.5-2.5 m/s). As further shown, the stance phase is divided into three subphases controlled plantar flexion (CP), controlled dorsiflexion (CD) and powered plantarflexion (PP). Various embodiments of the present disclosure may employ principles described in the Masters Thesis by Gates, D. H, entitled "Characterizing Ankle Function During Stair Ascent, Descent, and Level Walking for Ankle Prosthesis and Orthosis Design," submitted in 2004, the disclosure of which is hereby incorporated herein by reference in its entirety.

Figure 21:
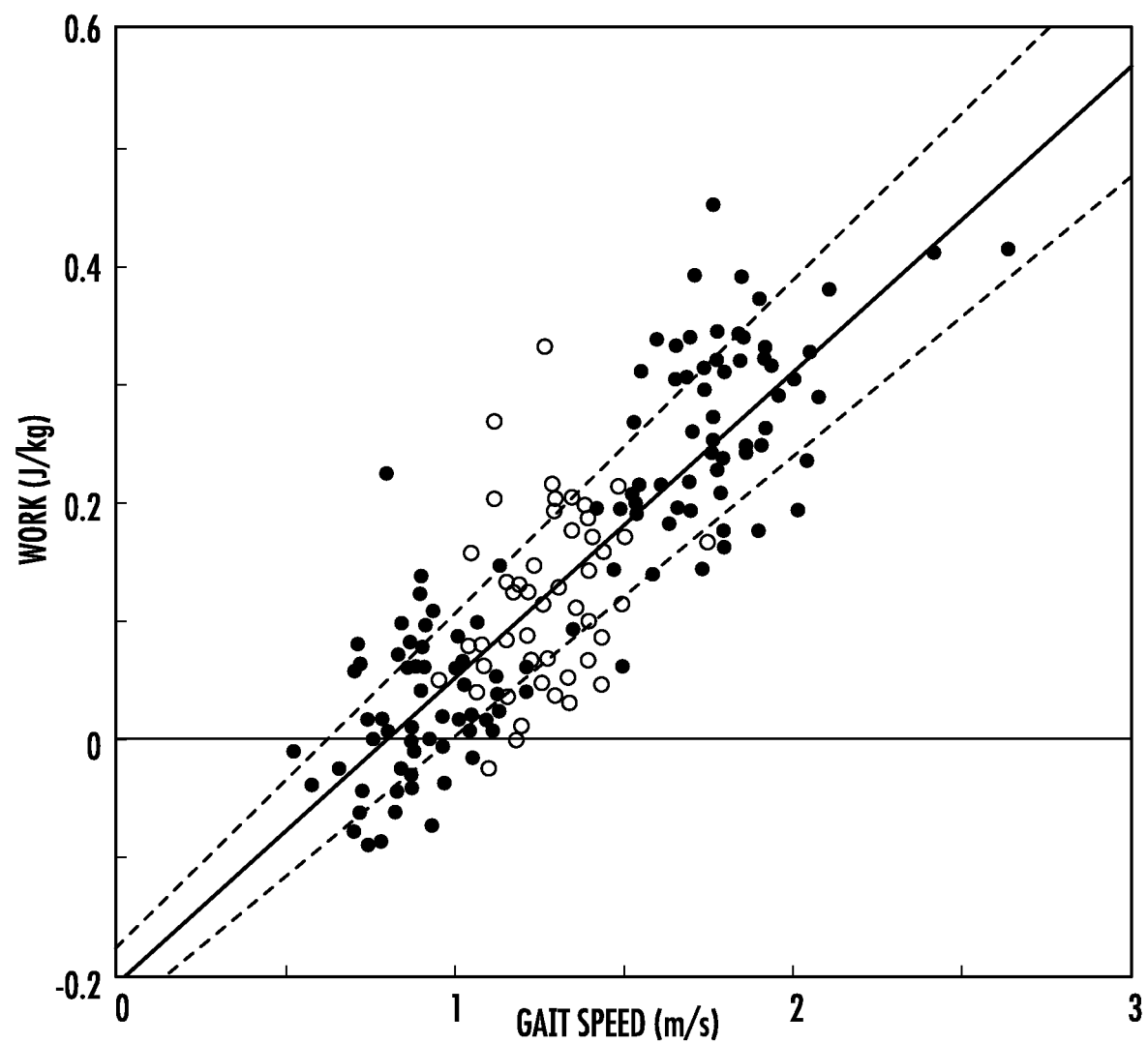
FIG. 21 depicts a relationship between net non-conservative ankle work and walking speed of walkers with intact limbs on level-ground.

FIG. 21 depicts a scatter plot graph of the net non-conservative ankle work ($W_{NET}=W_{PP}-(W_{CP}+W_{CD})$) on level-ground performed by walkers with an intact ankle (population N=70) during the stance phase of gait as a function of walking speed. Each point represents the average work done for all trials of a subject when asked to walk at a certain speed (fast, normal, slow). A linear regression was performed on the mean work for each subject walking at his or her mean speed. This line shows a significant increase in ankle work and linear correlation with gait speed. The rate-dependent, blended reflex disclosed above may be optimized to achieve a close fit to this linear net non-conservative ankle work vs. walking speed relationship.

Figure 22:
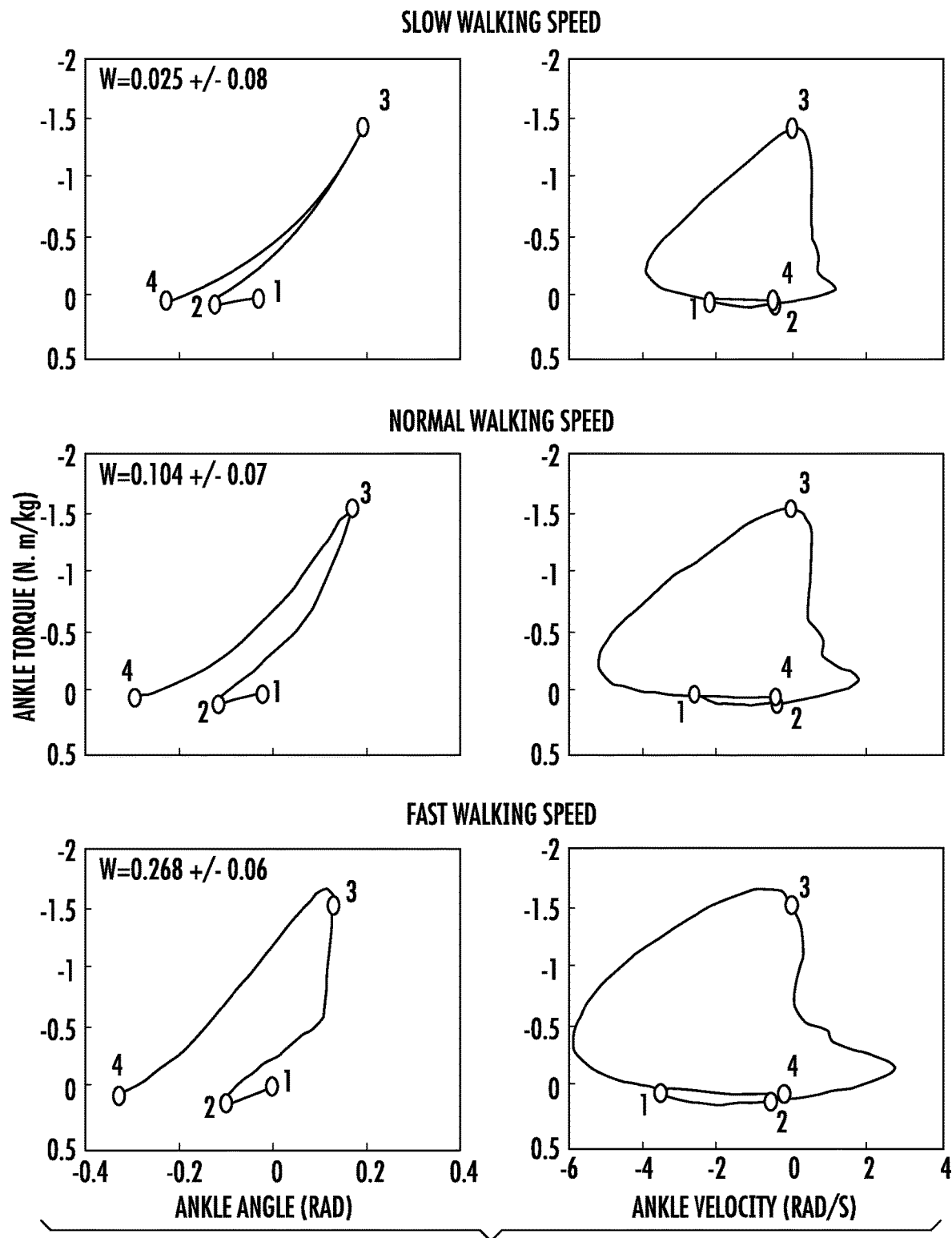
FIG. 22 shows normative ankle angle-torque and velocity-torque plots for the stance phase of a single gait cycle.

FIG. 22 illustrates the correlation between ankle torque and each of ankle angle and ankle velocity, during a single gait cycle. Data are shown for an average of all subjects walking at fast, normal, and slow speeds. Trials were normalized to 50 equally spaced data points, which was then averaged for each subject. Numbers mark the beginnings and ends of subphases of gait (CP: 1-2, CD: 2-3, PP: 3-4). As shown, at normal walking speeds, the ankle torque correlates strongly with ankle position during these subphases. As further shown, the faster the walking speed, the greater the net amount of work performed by the ankle (shown by the area under the curve for the ankle angle versus ankle torque graphs).

Figure 23:
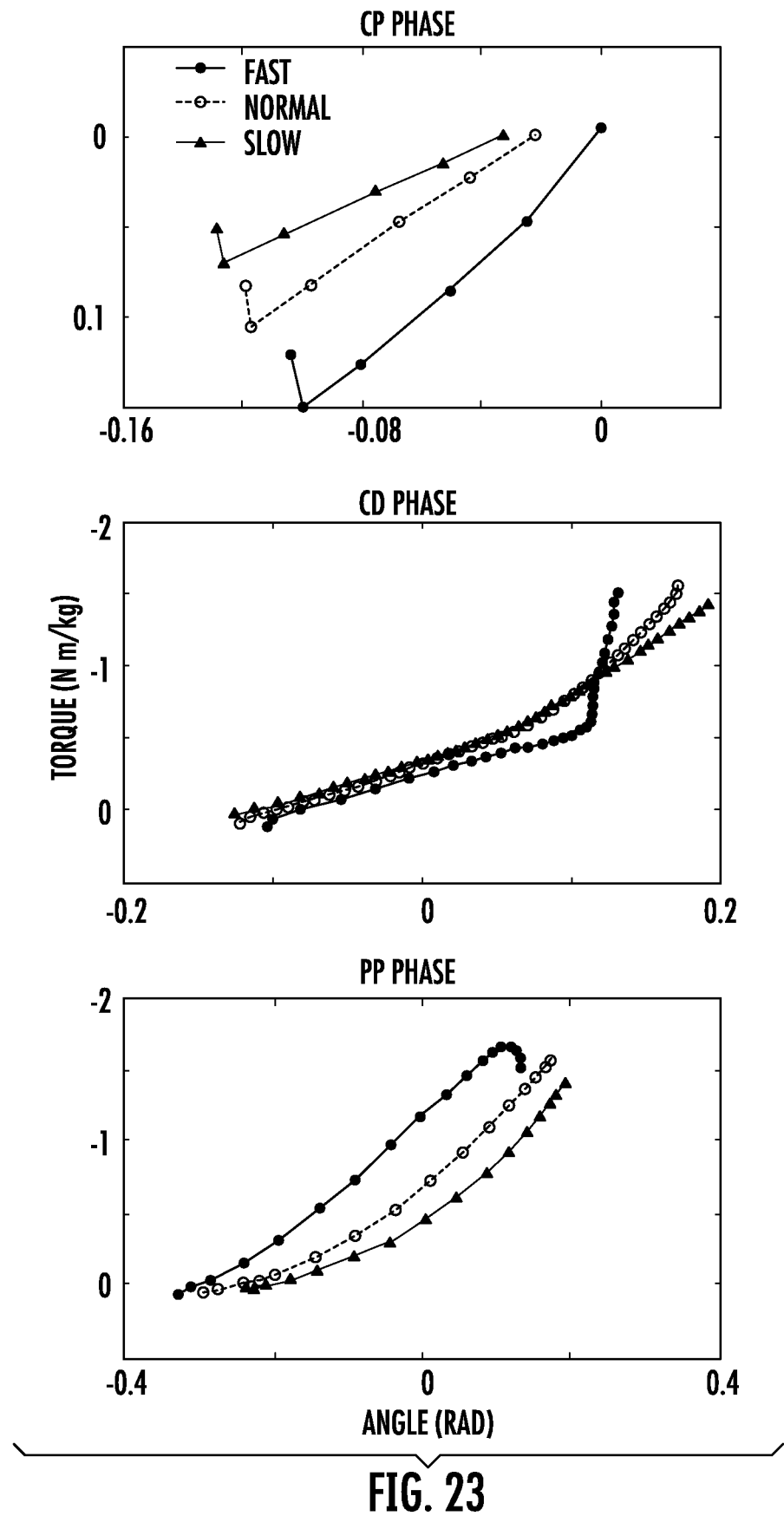
FIG. 23 depicts ankle torque versus ankle angle plotted for each subphase of a gait stance.

FIG. 23 shows graphs of ankle torque versus ankle angle plotted for each subphase of stance for walking subjects. Data are shown for the average of all subjects walking at their self-selected slow, normal and fast speeds. For the CP phase (top), there is a generally linear relationship at each walking speed. For the CD phase (middle), the relationship increases in non-linearity as speed increases. For the final phase, PP, the fitting is generally linear.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A prosthesis, orthosis or exoskeleton apparatus comprising:
   a proximal member;
   a distal member;
   a joint connecting the proximal and distal members, the joint adapted to permit flexion and extension between the proximal and distal members;
   a motorized actuator configured to apply a joint torque to the joint;
   a walking speed sensor configured to output a measurement from which a walking speed is derived; and
   a controller programmed with instructions that, when executed, cause the controller to modulate the joint torque applied by the motorized actuator, the modulation comprising:
      accessing a first torque response configured to be applied at a first walking speed;
      accessing a second torque response configured to be applied at a second walking speed, wherein the first walking speed is slower relative to the second walking speed;
      deriving the walking speed from the measurement of the walking speed sensor;
      blending the first torque response and the second torque response based on the derived walking speed to determine a blended torque response; and
      applying the blended torque response with the motorized actuator.

2. The apparatus of claim 1, wherein the first torque response and the second torque response are blended according to a linear interpolation based upon the derived walking speed.

3. The apparatus of claim 1, wherein the first torque response and the second torque response are blended according to a nonlinear interpolation based upon the derived walking speed.

4. The apparatus of claim 1, wherein the first torque response and the second torque response are blended according to a distance between the walking speed derived from the measurement of the walking speed sensor, the first walking speed, and the second walking speed.

5. The apparatus of claim 1, wherein the joint torque comprises a positive force-feedback component that comprises a gain and an exponent as applied to the joint torque.

6. The apparatus of claim 5, wherein the gain and the exponent take on values that are independent of each other.

7. The apparatus of claim 5, wherein the first torque response applies a slow-speed torque model that defines a slow-speed gain and a slow-speed exponent, and the second torque response applies a fast-speed torque model that applies a fast-speed gain and a fast-speed exponent.

8. The apparatus of claim 5, wherein the first torque response and the second torque response apply a single torque model with the gain and exponent being interpolated based on the walking speed derived from the measurement of the walking speed sensor.

9. The apparatus of claim 1, further comprising a phase sensor configured to detect at least one of a phase and a change in a phase of joint motion in a repetitive cycle, each occurrence of the cycle comprising a plurality of phases, wherein the motorized actuator is configured to apply the joint torque during a powered plantarflexion phase of locomotion.

10. The apparatus of claim 1, wherein the controller is further configured to access additional torque models and blend the additional torque models based on the walking speed derived from the measurement of the walking speed sensor.

11. A method applied to a prosthesis, orthosis or exoskeleton apparatus comprising a proximal member, a distal member, a joint connecting the proximal and distal members, the joint adapted to permit flexion and extension between the proximal and distal members, a motorized actuator configured to apply a joint torque to the joint, a walking speed sensor configured to output a measurement from which a walking speed is derived, and a controller, the method comprising:

accessing a first torque response configured to be applied at a first walking speed;

accessing a second torque response configured to be applied at a second walking speed, wherein the first walking speed is slower relative to the second walking speed;

deriving the walking speed from the measurement of the walking speed sensor;

blending the first torque response and the second torque response based on the derived walking speed to determine a blended torque response; and applying the blended torque response with the motorized actuator.

12. The method of claim 11, wherein the first torque response and the second torque response are blended according to a linear interpolation based upon the derived walking speed.

13. The method of claim 11, wherein the first torque response and the second torque response are blended according to a nonlinear interpolation based upon the derived walking speed.

14. The method of claim 11, wherein the first torque response and the second torque response are blended according to a distance between the walking speed derived from the measurement of the walking speed sensor, the first walking speed, and the second walking speed.

15. The method of claim 11, wherein the joint torque comprises a positive force-feedback component that comprises a gain and an exponent as applied to the joint torque.

16. The method of claim 15, wherein the gain and the exponent take on values that are independent of each other.

17. The method of claim 15, wherein the first torque response applies a slow-speed torque model that defines a slow-speed gain and a slow-speed exponent, and the second torque response applies a fast-speed torque model that applies a fast-speed gain and a fast-speed exponent.

18. The method of claim 15, wherein the first torque response and the second torque response apply a single torque model with the gain and exponent being interpolated based on the walking speed derived from the measurement of the walking speed sensor.

19. The method of claim 11, further comprising a phase sensor configured to detect at least one of a phase and a change in a phase of joint motion in a repetitive cycle, each occurrence of the cycle comprising a plurality of phases, wherein the motorized actuator is configured to apply the joint torque during a powered plantarflexion phase of locomotion.

20. The method of claim 11, wherein the controller is further configured to access additional torque models and blend the additional torque models based on the walking speed derived from the measurement of the walking speed sensor.

21. A non-transitory computer-readable storage medium, the computer-readable storage medium including instructions that when executed by a controller, cause the controller to modulate a torque applied to a prosthesis, orthosis or exoskeleton apparatus comprising a proximal member, a distal member, a joint connecting the proximal and distal members, the joint adapted to permit flexion and extension between the proximal and distal members, a motorized actuator configured to apply a joint torque to the joint, and a walking speed sensor configured to output a measurement from which a walking speed is derived, the instructions comprising instructions to:

access a first torque response configured to be applied at a first walking speed;

access a second torque response configured to be applied at a second walking speed wherein the first walking speed is slower relative to the second walking speed;

derive the walking speed from the measurement of the walking speed sensor;

blend the first torque response and the second torque response based on the derived walking speed to determine a blended torque response; and apply the blended torque response with the motorized actuator.

22. The computer-readable storage medium of claim 21, wherein the first torque response and the second torque response are blended according to a linear interpolation based upon the derived walking speed.

23. The computer-readable storage medium of claim 21, wherein the first torque response and the second torque response are blended according to a nonlinear interpolation based upon the derived walking speed.

24. The computer-readable storage medium of claim 21, wherein the first torque response and the second torque response are blended according to a distance between the walking speed derived from the measurement of the walking speed sensor, the first relatively slow walking speed, and the second walking speed.

25. The computer-readable storage medium of claim 21, wherein the joint torque comprises a positive force-feedback component that comprises a gain and an exponent as applied to the joint torque.

26. The computer-readable storage medium of claim 25, wherein the gain and the exponent take on values that are independent of each other.

27. The computer-readable storage medium of claim 25, wherein the first torque response applies a slow-speed torque model that defines a slow-speed gain and a slow-speed exponent, and the second torque response applies a fast-speed torque model that applies a fast-speed gain and a fast-speed exponent.

28. The computer-readable storage medium of claim 25, wherein the first torque response and the second torque response apply a single torque model with the gain and exponent being interpolated based on the walking speed derived from the measurement of the walking speed sensor.

29. The computer-readable storage medium of claim 21, wherein the instructions further configure the apparatus to detect at least one of a phase and a change in a phase of joint motion in a repetitive cycle, each occurrence of the cycle comprising a plurality of phases, and apply the joint torque during a powered plantarflexion phase of locomotion.

30. The computer-readable storage medium of claim 21, wherein the controller is further configured to access additional torque models and blend the additional torque models based on the walking speed derived from the measurement of the walking speed sensor.

* * * * *